(12) United States Patent  (10) Patent No.: US 7,704,745 B2
Baudenbacher et al.  (45) Date of Patent: Apr. 27, 2010

(54) APPARATUS AND METHODS FOR MONITORING THE STATUS OF A METABOLICALLY ACTIVE CELL

(75) Inventors: Franz Baudenbacher, Franklin, TN (US); John P. Wikswo, Brentwood, TN (US); R. Robert Balcarcel, Nashville, TN (US); David Cliffel, Nashville, TN (US); Sven Eklund, Antioch, TN (US); Jonathan Mark Gilligan, Nashville, TN (US); Owen McGuinness, Brentwood, TN (US); Todd Monroe, Baton Rouge, LA (US); Ales Prokop, Nashville, TN (US); Mark Andrew Stremler, Franklin, TN (US); Andreas Augustinus Werdich, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 781 days.

(21) Appl. No.: 10/213,049

(22) Filed: Aug. 6, 2002

(65) Prior Publication Data

US 2009/0305319 A1  Dec. 10, 2009

Related U.S. Application Data

(60) Provisional application No. 60/310,652, filed on Aug. 6, 2001.

(51) Int. Cl.
 *G01N 33/00* (2006.01)
(52) U.S. Cl. ............... 436/34; 435/1.1; 435/2; 435/3; 435/29; 435/366; 435/373; 435/374; 435/285.2; 435/286.1; 435/287.1; 436/2; 436/50; 436/62; 436/63; 436/68; 436/147; 436/149; 422/82.01; 422/90; 422/91; 422/92

(58) Field of Classification Search .......... 436/503, 436/517, 2, 18, 34, 55, 62, 63, 147, 148, 436/149, 163, 50, 68; 422/51, 63, 73, 79, 422/82.01, 82.12, 95, 98, 68.1, 80, 90, 91, 422/92; 435/1.1, 2, 3, 5, 7.2, 29, 30, 32, 435/40.5, 373, 374, 375, 379, 383, 384, 284.1, 435/285.2, 286.1, 286.4, 286.5, 287.1, 366, 435/289.1

See application file for complete search history.

(56) References Cited

U.S. PATENT DOCUMENTS 3,403,081 A  9/1968 Rohrback et al.

(Continued)

FOREIGN PATENT DOCUMENTS

DE  19512117 A1  10/1996

(Continued)

OTHER PUBLICATIONS

Hafner (Cytosensor Microphysiometer: technology and recent applications, Biosensors and Bioelectronics 15: 149-158 (Jul. 28, 2000)).—Date of publication provided by BIOSTIC.*

(Continued)

*Primary Examiner*—Gailene R Gabel
(74) *Attorney, Agent, or Firm*—Morris Manning & Martin; Tim Tingkang Xia, Esq.

(57) ABSTRACT

An apparatus and methods for monitoring the status of a cell that consumes oxygen. In one embodiment of the present invention, the method includes the steps of confining the cell in a sensing volume, measuring dynamically intracellular or extracellular signaling of the cell, and determining the status of the cell from the measured intracellular or extracellular signaling of the cell.

19 Claims, 41 Drawing Sheets

U.S. PATENT DOCUMENTS

| | | | |
|---|---|---|---|
| 4,015,135 A | 3/1977 | Tipton, Jr. | |
| 4,319,271 A | 3/1982 | Hurni et al. | 358/107 |
| 4,746,607 A | 5/1988 | Mura et al. | |
| 5,158,868 A * | 10/1992 | Bergkuist et al. | 435/4 |
| 5,278,048 A | 1/1994 | Parce et al. | 436/29 |
| 5,520,787 A * | 5/1996 | Hanagan et al. | 204/403.14 |
| 5,536,662 A | 7/1996 | Humphries et al. | 435/287.1 |
| 5,747,265 A | 5/1998 | Parsons et al. | |
| 5,888,825 A | 3/1999 | Carr et al. | 436/48 |
| 5,902,732 A | 5/1999 | Hochman | 435/29 |
| 6,051,422 A | 4/2000 | Kovacs et al. | |
| 6,096,510 A | 8/2000 | Hochman | 435/29 |
| 6,151,519 A | 11/2000 | Sugihara et al. | |
| 6,197,575 B1 | 3/2001 | Griffith et al. | 435/288.4 |
| 6,268,168 B1 | 7/2001 | Farb et al. | |
| 6,277,629 B1 | 8/2001 | Wolf et al. | 435/288.3 |
| 6,280,586 B1 | 8/2001 | Wolf et al. | 204/403 |
| 6,344,325 B1 | 2/2002 | Quake et al. | 435/6 |
| 2002/0106627 A1* | 8/2002 | Vandenburgh et al. | 435/4 |

FOREIGN PATENT DOCUMENTS

| | | |
|---|---|---|
| EP | 0881490 A2 | 12/1998 |
| FR | 2646510 A | 11/1990 |
| GB | 2029026 A | 3/1980 |
| JP | 03134527 A | 6/1991 |
| WO | 9610742 A | 4/1996 |
| WO | WO 99/31503 | 6/1999 |
| WO | 9960371 A | 11/1999 |
| WO | 0066266 A | 11/2000 |
| WO | 0150102 A1 | 7/2001 |

OTHER PUBLICATIONS

O'Riordan et al. (A Cell Viability Assay Based on Monitoring Respiration by Oxygen Sensing, Analytical Biochemistry 278:221-227 (2000)).*

Schon et al. (Microcalorimetric measurements on tissue cells attached to microcarriers in stirred suspension, Journal of Biochemical and Biophysical Methods 13: 135-143 (1986)).*

Bousse (Whole Cell Biosensors, Sensors and Actuators B 34 270-275 (1996)).*

Baumann et al. (Microelectronic Sensor System for Microphysiological Application on Living Cells, Sensors and Actuators B 55 77-89 (1999)).*

Hollis et al. (Design and Application of Biosensor for Monitoring Toxicity of Compounds of Eukaryotes, Applied and Environmental Microbiology 1676-1679 (Apr. 2000)).*

Adams, Scott V., et al., "Coupling in serotonin transporters: A simple channel model", Biophysical Journal, vol. 78, 291-POS (2000).

Adler, Stephen; et al., "Glomerular edothelial cell injury mediated by shiga-like toxin-l", Kidney Blood Press Res., vol. 21, pp. 13-21 (1998).

Aepfelbacher, Martin, et al., "Bacterial toxins block endothelial wound repair", Arterioscler Thromb Vasc. Biol., vol. 17, pp. 1623-1629 (1997).

Airoldi, Claudio, "O uso de calorimetria em ecologia", Quimica Nova, vol. 21, No. 5, pp. 635-641 (1998), Abstract.

Albers, Bert P., et al., "Flow-microcalorimetry measurements of aerobic and anaerobic soil microbial activity", Biol Fertil Soils, vol. 19, pp. 203-208 (1995).

Almagor, Miriam, et al., "Differential scanning calorimetry of nuclei as a test for the effects fo anticancer drugs on human chromatin", Cancer Research, vol. 49, pp. 5561-5566 (1989).

Amado, Rafael, G., et al., "Lentiviral vectors—the promise of gene therapy within reach", Science, vol. 285 pp. 674-676 (1999).

Bäckman, P., et al., "A system of microcalorimeters", Pure & Appl. Chem., vol. 66, No. 3, pp. 375-382 (1994).

Bäckman, P., et al., "Effects of pH-variations on the kinetics of growth and energy metabolism in cultured t-lymphoma cells: A microcalorimetric study", Journal of Cellular Physiology, vol. 150, pp. 99-103 (1992).

Bäckman, P., et al., "Cell growth experiments using a microcalorimetric vessel equipped with oxygen and pH electrodes", J. Biochem. and Biophys. Methods, vol. 23, pp. 283-293 (1991).

Bäckman, Per Ove Michael, "Heat production in cellular systems: a thermochemical and methodological study (Thermochemistry)", Abstract, DIA-C, vol. 53, No. 1, pp. 107-254 (1992).

Baller, M.K., et al., "A cantilever array-based artificial nose", Ultramicroscopy, vol. 82, pp. 1-9 (2000).

Bandmann, U., et al., "Microcalorimetric measurements of heat production in whole blood and blood cells of normal person", Scand. J. clin. Lab. Invest., vol. 35, pp. 121-127 (1975).

Barnes, J. R., "A femtojoule calorimeter using micromechanical sensor", Rev. Sci. Instrum., vol. 65, (seven•pages) (1994).

Barnes, J.R., et al., "Photothermal spectoroscopy with femtojoule sensitivity using a micromechnanical device", Nature, vol. 278, pp. 79-80 (1994).

Battley, Edwin H., The advantages and disadvantages of direct and indirect calorimetry, Thermochimica Acta, vol. 250, pp. 337-352 (1995).

Baumann, W.H., et al., "Microelectronic sensor system for microphysiological application on living cells", Sensors and Actuators B, vol. 55, pp. 77-89 (1999).

Bayram, Mustafa "Automatic analysis of the control of metabolic networks", Comput. Biol. Med., vol. 26, No. 5, pp. 401-408 (1996).

Béknert, C., et al., "Use of in vitro (Ames and Mutatox Tests) and in vivo (Amphibian Micronucles Test) assays to assess the genotoxicity of leachates from a contaminated soil", Organic Geochemistry, vol. 30, pp. 953-962 (1999).

Blakely, R. D., et al., "Regulation of neurotransmiiter transporters through kinase-mediated trafficking", W-PM-P2 (Abstract), Biophysical Journal, vol. 74, No. 2, A252, 42nd Annual Meeting, (1998).

Bonnet, Grégoire, et al., "Thermodynamic basis of the enhanced specificity of structured DNA probes ", Proc. Natl. Acad. Sci., vol. 96, pp. 6171-6176 (1999).

Böttcher, H., et al., "Microcalorimetric and biochemical investigations of thermogenesis and metabolic pathways in human white adipocytes", International Journal of Obesity, vol. 20, pp. 874-881 (1996).

Böttcher, H., et al., "Direct microcalorimetry as a technique in cell cultures", Baillière's Clinical Endocrinology and Metabolism, vol. 11, No. 4, pp. 739-752 (1997).

Brennan, John D., et al., "A novel biochemical sensor", Chemtech., vol. 22, pp. 227-235 (1992).

Bratten, Craig, D.T., et al., "Micromachining sensors for electrochemical measurement in subnanoliter volumes", Anal. Chem., vol. 69, No. 2, pp. 253-258 (Jan. 15, 1997).

Bratten, Craig, D.T., et al., "Single-cell measurements of purine release using a micromachined electroanalytical sensor", Anal. Chem., vol. 70, No. 6, pp. 1164-1170 (Mar. 15, 1998).

Bratten, Craig, D.T., et al., "Enzyme assay using ultra-low volume surface micromachined sensors", Chem. Commun., pp. 471-472 (1998).

Bryzek, Janusz, et al., "Micromachines on the march", IEEE Spectrum, pp. 20-31 (1994).

Buck, L. T., "Microcalorimetric measurement of reversible metabolic supression induced by anoxia in isolated hepatocytes", Am. J. Physiol. 265 (Regulartory Integrative Comp. Physiol. vol. 34), pp. R1014-R1019 (1993).

Buntine Wray, et al., "Knowledge-based artificial intelligence systems in aerospace and industry", SPIE Proceedings Series, vol. 2244, pp. 249-260 (1994).

Cao, C. J., et al., "Cytotoxicity of organophosphate anticholinesterases", In Vitro Cell. Dev. Biol. Anim., vol. 35, pp. 493-500 (1999).

Certa, Ulrich, et al., "Biosensors in biomedical research: Development and applications of gene chips", Chimia, vol. 53, No. 3, pp. 57-61 (1999).

Chang-Li, Xie, et al., "Microcalorimetric studies on tetrahymena pyriformis Part I. Growth metabolic power and thermal equations", Thermochimica Acta, vol. 183, pp. 117-123 (1991).

Clark, Rose A., et al., "Electrochemical analysis in picoliter microvials", Anal. Chem., vol. 69, No. 2, pp. 258-263 (Jan. 15, 1997).

Cleland, A. N., et al., "*A Nanometr-scale mechanical electrometer*", Nature, vol. 392, pp. 160-162 (1998).

Codina, J. C., et al., "*Detection of heavy metal toxicity and genotoxicity in wastewaters by microbial assay*", Wat. Sci. Tech., vol. 30, No. 10, pp. 145-151 (1994).

Cooper, Jonathan M., "*Towards electronic petri dishes and picolitre-scale single-cell technologies*", Tibtech, vol. 17, pp. 226-230 (Jun. 1999).

Criddle, R.S., et al., "*Simultaneous measurement of metabolic heat rate, $CO_2$ production, and $O_2$ consumption by microcalorimetry*", Analytical Biochemistry, vol. 194, pp. 413-417 (1991).

Culic Ognjen, et al., "*Energy turnover of vascular endothelial cells*", Am. J. Physiol, vol. 273 (Cell Physiol, vol. 42), pp. C205-C213 (1997).

Davies, Kelvin J. A., "*The broad spectrum of responses to oxidants in proliferating cells: A New Paradigm for Oxidative Stress*", IUBMB Life, vol. 48, pp. 41-47 (1999).

DeFelice, Louis J., "*Information isn't everything*", Science, vol. 284, pp. 1935 (1999).

Delseny, Michel, "*La génomique: méthodes et premiers résultats*", OCL, vol. 6, No. 2, pp. 136-143 (1999), Abstract.

Denlinger, D.W., et al., "*Thin film microcalorimeter for heat capacity measurements from 1.5 to 800k*", Rev. Sci. Instrum., vol. 65, No. 4, pp. 946-959 (1994).

Dereniak, Eustace, L., et al., "*Infrared Detector and focal Plane Arrays V*", SPIE, vol. 3379, pp. 193-197 (1998).

di Toppi, L. Sanità, et al., "*Response to cadmium in higher plants*", Environmental and Experimental Botany, vol. 41, pp. 105-130 (1999).

Dunn, Michael J., "*Studying heart disease using the proteomic apparoach*", Drug Discovery Today, vol. 5, No. 2, pp. 76-84 (2000).

Dupin, Hubert J. et al., "*Mesoscale and microscale observations of biological growth in a silicon pore imaginary element*", Environ. Sci. Technol., vol. 33, No. 8, pp. 1230-1236 (1999).

Dupin, Hubert J. et al., "*Impact of colony morphologies and disinfection N on biological clogging in porus media*", Environ. Sci. Technol., vol. 34, No. 8, pp. 1513-1520 (2000).

Eberwine, James, et al., "*Analysis of gene expression in single live neurons*", Proc. Natl. Acad. Sci., vol. 89, pp. 30103014 (1992).

Ehret, R., et al., "*On-line control of cellular adhesion with impedance measurements using interdigitated electrode structures*", Medical & Biological Engineering & Computing, vol. 36, pp. 365-370 (1998).

Engström, Iva, et al., "*Dissipation of the calcium gradient in human erythrocytes results in increased heat production*", Clinica Chimica Acta, vol. 219, pp. 113-122 (1993).

Eray, Mete, et al., "*A highly stable and selective biosensor using modified nicotinic acetylcholine receptor (nAChR)*", Biosystems, vol. 35, pp. 183-186 (1995).

Eray, Mete, et al., "*Highly stable bilayer lipid membranes (BLMs) formed on microfabricated polyimide apertures*", Biosensors & Bioelectronics, vol. 9, pp. 343-351 (1994).

Essler, Markus, et al., "*Pasteurella multocida toxin increases endothelial permeability via rho kinase and myosin light chain phosphatase*", The Journal of Immunology, vol. 161, pp. 56405646 (1998).

Eyer, Kurt, et al., "*On-line estimation of viable cells in a hybridoma culture at various DO levels using atp balancing and redox potential measurment*", Biotechnology and Bioengineering, vol. 49, pp. 277-283 (1996).

Fagher, Birger, et al., "*Thermogenesis in human skeletal muscle as measured by direct microcalorimetry and muscle contractile performance during β-adrenoceptor blockade*", Clinical Science, vol. 70, pp. 435-441 (1986).

Fagher, Birger, et al., "*Increased myocardial oxygen consumption and resting heat production, as measured by microcalorimetry, after propranolol and carvedilol teatment: Is there a partial agonistic effect in the rat?*", Thermochimica Acta, vol. 298, pp. 75-80 (1997).

Fields, Stanley, et al., "*Functional genomics*", Proc Natl. Acad. Sci., vol. 96, pp. 88258826 (1999).

Figeys, D., et al., "*Microfabricated modules for sample handling, sample concentration and flow mixing: application to protein analysis by tandem mass spectrometry*", Journal of Biomenchanical Engineering, vol. 121, pp. 7-12 (1999).

Flavahan, N.A., et al., "*G-Proteins and endothelial responses*", Blood Vessels, vol. 27, pp. 218-229 (1990).

Foote, Marc C., et al., "*High performance micromachined thermopile linear arrays*", SPIE, vol. 3379, pp. 192-197 (1998).

Forst, Christian, V., et al., "*Evolution of metabolisms: A new method for the comparison of metabolic pathways using genomics information*", Journal of Computational Biology, vol. 6, Nos. 3/4, pp. 343360 (1999).

Freire, Ernesto, et al., "*Isothermal titration on calorimetry*", Analytical Chemistry, Vo. 62, No. 18., pp. 950A-959A (1990).

Galli, Aurelio, et al., "*Patch-clamp and amperometric recordings from norepinephrine transporters: channel activity and voltage-dependent uptake*", Proc. Natl. Acad. Sci., vol. 95, pp. 13260-13265 (1998).

Galli, A., et al., "*Steady-state currents and fluctuation analysis in proline transporters*", Biophysical Journal, vol. 72, TH-120 (1997).

Garfield, R. E., et al., "*Are gap junctions necessary for cell-to-cell coupling of smooth muscle?: an update[1]*", Can. J. Physiol. Pharmacol., vol. 70, pp. 481-490 (1992).

Gebreselassie, D., et al., "*Energetic study human lymphocytes and the metabollic response to antigenic stimulation*", Thermochimica Acta, Vo. 251, pp. 177-182 (1995).

Giebisch, G., "*Membrane transport in biology*", Concepts & Models, Preface, vol. 1, pp. v & vi (1978).

Godovac-Zimmermann, Jasminka, et al., "*Functional proteomics of signal transduction by membrane receptors*", Electrophoresis, vol. 20, pp. 952-961 (1999).

González, C., "*Fluidic interconnects for modular assembly of chemical microsystems*", Sensors and Actuators B, vol. 49, pp. 40-45 (1998).

Grieme, L.E., et al., "*Method for use of a differential scanning calorimeter for determination of bacterial thermal death times*", Journal of Food Protection, vol. 46, No. 9, pp. 797-801 (1983).

Gritsch, Stefan, et al., "*Impedance spectroscopy of porin and gramicidin pores reconstituted into supported lipid bilayers on indium-tin-oxide electrodes*", Langmuir, vol. 14, pp. 3118-3125 (1998).

Gruwel, Marco L. H., et al., "*Na'-K'-ATPase in endothelial cell energetics:[23]Na nuclear magnetic resonance and calorimetry study*", Am. J. Physiol., vol. 268 (Heart Circ. Physiol. vol. 37), pp. H351-H358 (1995).

Guadaño, Ana, et al., "*Development of a new bioluminescent mutagenicity assay based on the ames test*", Mutagenesis, vol. 14, No. 4, pp. 411-415 (1999).

Guan, Yue, et al., "*Specific heat flow rate: an on-line monitor and potential control variable of specific metabolic rate in animal cell culture that combines microcalorimetry with dielectric spectroscopy*", Biotechnology and Bioengineering, vol. 58, No. 5, pp. 464-476 (1998).

Hafner, Frank, "*Cytosensor® Microphysiometer: Technology and Recent Applications*", Biosensors & Bioelectronics, vol. 15, pp. 149-158 (2000).

Hartmund, T., et al., "*Acidosis. glycolysis and energy state in anaerobic heart tissue from rainbow trout*", J. Comp. Phys. B, vol. 165, pp. 219-229 (1995).

Hatzimanikotis, Vassily, et al., "*Proteomics: theoretical and experimental considerations*", Biotechnol. Prog., vol. 15, pp. 312-318 (1999).

Hediger, S., et al., "*Fabrication of a novel microsystem for the electrical characterization of cell arrays*", Sensors and Actuators B, vol. 56, pp. 175-180 (1999).

Higareda, Ana E., et al., "*The use of culture redox potential and oxygen uptake rate for assessing glucose and glutamine depletion in hybridoma cultures*" Biotechnol. Bioeng, vol. 56, pp. 555-563 (1997).

Hua, Qiang, et al., "*Effect of dissolved oxygen concentration on the intracellular flux distribution for pyruvate fermentation*", Journal of Biotechnology, vol. 68, pp. 135-147 (1999).

Humphery-Smith, Ian, et al., "*Proteome analysis: genomics via the output rather than the input code*", Journal of Protein Chemistry, vol. 16, No. 5, pp. 537-544 (1997).

Inskeep, Philip B., et al., "Alterations in motility and metabolism associated with sperm interaction with accessory sex gland fluids[1]", Archives of Biochemistry and Biophysics, vol. 241, No. 1, pp. 1-9 (1985).

Issautier, Thierry, et al., "Modulation defect of sodium pump evidenced in diabetic patients by a microcalorimetric study", Clinica Chimica Acta, vol. 228, pp. 161-170 (1994).

Kane, Ravi S., et al., "Patterning proteins and cells using soft lithography", Biomaterials, vol. 20, pp. 2363-2376 (1999).

Kauffman, Frederick C., et al., "Activation of glycogen phosphorylase in rat pheochromocytoma PC12 cells and isolated hepatocytes by organophosphates"Biochemical Pharmacology, vol. 39, No. 2., pp. 347-354 (1990).

Kemp, R. B., et al., "An enthalpy balance approach to the study of metabolic activity in mammalian cells", Journal of Thermal Analysis, vol. 49, pp. 755-770 (1997).

Kemp, R. B., et al., "Heat flux and the calorimetric-respirometric ratio as measures of catabolic flux in mammalian cells", Thermochimica Acta, vol. 300, pp. 199-211 (1997).

Kemp, R. B., et al., "The calorimetric-respirometric ratio: Its potentioal as a cytotoxicity test", Atla, vol. 22, pp. 364-376 (1994).

Kinsella, J. L., et al., "Protein kinase C regulates endothelial cell tube formation on basement membrane matrix, matrigel", Experimental Cell Research, vol. 199, pp. 56-62 (1992).

Koenigbauer, Michael J., "Pharmaceutical applications of microcalorimetry", Pharmaceutical Research, vol. 11, No. 6, pp. 777-783 (1994).

Krüll, Matthias, et al., "Escherichia coli hemolysin and staphylococcus aureus α-toxin potently induce neutrophil adhesion to cultured human endothelial cells", Journal of Immunology, vol. 157, pp. 41334140 (1996).

Lampugnani, Maria Grazia, et al., "The molecular organization of endothelial cell to cell junctions: Differential association of plakoglobin, β-catenin, and α-catenin with vascular endothelial cadherin (VE-cadherin)", The Journal of Cell Biology, vol. 129, No. 1, pp. 203-217 (1995).

Legrand et al., U.S. Publication No. 2002/0024728, Publication date Feb. 28, 2002, U.S. Appl No. 09/927,290, filed Aug. 10, 2001, "Solid Immersion Lens Structures and Methods for Producing Solid Immersion Lens Structures".

Lönnbro, Per, et al., "the effect of temperature on metabolism in 3T3 cells and SV40-transformed 3T3 cells as measured by microcalorimetry", Thermochimica Acta, vol. 172, pp. 75-80 (1990).

Loseva, N.L., et al., "Aspects of the energetic balance of plant cells under different salt conditions",Thermochimica Acta, vol. 251, pp. 357-362 (1995).

Luque, Irene, et al., "Structure-based thermodynamic scale of α-helix propensities in amino acids", Biochemistry, vol. 35, 13681-13688 (1996).

Mabrouk, Gehan M., et al., "Cell signalling and the hormonal stimulation of the hepatic glycine cleavage enzyme system by glucagon", Biochem. J., vol. 330, pp. 759-763 (1998).

Majumdar, A., "Scanning thermal microscopy", Annu. Rev. Mater. Sci., vol. 29, pp. 505-585 (1999).

Manzano, Anna, et al., "Effects of taxol on isolated rat hepatocyte metabolism", Am. J. Physiol., vol. 271 (Cell Physiol. vol. 40), pp. C1957-C1962 (1996).

Matsuo, Toshihiko, "In situ visualization of messenger RNA for basic fibroblast growth factor in living cells", Biochimica et Biophysica Acta, vol. 1379, pp. 178-184 (1998).

Mizutani, Fumio, "Application of enzyme-modified electrodes to biosensors (Review)", Bunseki Kagaku, vol. 48, No. 9, pp. 809-822 (1999), Abstract.

Monti, M., et al., "Medical application of microcalorimetry in human toxicology. A study of blood compatibility of hemodialysis membranes", Pure & Appl. Chem,. vol. 65, No. 9, pp. 1979-1981 (1993).

Monti, M., et al., "In vitro thermal studies of blood cells", Thermal and Energetic Studies of Cellular Biological Systems, Chapter 6, pp. 131-145 (1987).

Motterlini, Roberto, et al., "Depression of endothelial and smooth muscle cell oxygen consumption by endotoxin", Am. J. Physiol., 275 (Heart Circ. Physiol. 44), pp. H776-H782 (1998).

Moulin, A. M., et al., "Micromechanical thermal sensors: comparison of experimental results and simulations", J. Vac. Sci. Technol. B. vol. 15, No. 3, pp. 590-596 (1997).

Murphy, Kenneth P., et al., "Thermodynamics of structural stability and cooperative folding behavior in proteins", Advances in Protein Chemistry, vol. 43, pp. 313-361 (1992).

Murphy, Kenneth P., et al., "Configurational effects in antibody-antigen interactions studied by microcalorimetry", Proteins: Structure, Function, and Genetics, vol. 21, pp. 83-90 (1995).

Nässberger, Lennart, et al., "Microcalorimetric investigation of metabolism in rat hepatocytes cultured on microplates and in cell suspensions", Biochimica et Biophysica Acta, vol. 882, pp. 353-358 (1986).

Newman, Albert, B., "The drying of porous solids: Diffusion and surface emission equations", Am. Inst. of Chem. Engineers, pp. 203-220 (1931).

Neykov, A., et al., "Mathematical modeling of the biosensor systems", Biotechnol. & Biotechnol. Eq., vol. 12, pp. 100-109 (1998).

Nicosia, Roberto F., et al., "Modulation of microvascular growth and morphogenesis by reconstituted basement membrane gel in three-dimensional cultures of rat aorta: A comparative study of angiogenesis in matrigel, collagen, fibrin, and plasma clot", In Vitro Cell. Dev. Biol., vol. 26, pp. 119-128 (1990).

Nilsson-Ehle, P., et al., "Microcalorimetric studies on the total metabolic activity of fat cells", International Journal of Obesity, vol. 9, Suppl. 1, pp. 169-172 (1985).

Nittinger, Jüurgen, et al., "Microcalorimetric Investigations on human leukemia cells -Molt 4", Biol. Cell, vol. 70, pp. 139-142 (1990).

Nordmark, Görman, M., et al., "Design and testing of a new microcalorimetric vessel for use with living cellular systems and in titration experiments", Journal of Biochemicla and Biophysical Methods, vol. 10, pp. 187-202 (1984).

O' Riordan, Tomás C., et al., "A cell viability assay based on monitoring respiration by optical oxygen sensing", Analytical Biochemistry, vol. 278, pp. 221-227 (2000).

Oden, P. I., et al., "Uncooled thermal imaging using a piezoresistive microcantilever", Appl. Phys. Letter., vol. 69, No. 21, pp. 3277-3279 (1996).

Okamoto, Masahiro, et al., "Biochemical neuron: hardware implementation of functional devices by mimicking the natural intelligence such as metabolic control systems", Computers and Electrical Engineering, vol. 25, pp. 421-438 (1999).

Oldshue, James Y., Ph.D., "Fluid mixing technology", Chemical Engineering (McGraw-Hill Publications), Preface pp. v-vi.

Osterman, D.P., et al., "An x-ray microcalorimeter with kinetic inductance thermometer and dc SQUID read-out", Journal of Low Temperature Physics, vol. 93 Nos. 3/4, (1993).

Osterman, D.P., et al., "Antenna-coupled bolometer with a micromachined-beam thermal ink", Appl. Phys. Lett., vol. 71, No. 16, pp. 2361-2363 (1997).

Osterman, D.P., et al., "Uncooled micromachined thermopile arrays and read-out circuits", SPIE, vol. 3698, pp. 376-386 (1999).

Owicki, John C., et al., "Continuous monitoring of receptor-mediated changes in the metabolic rates of living cells", Proc. Natl. Acad. Sci., vol. 87, pp. 4007-4011 (1990).

Owicki, John C., et al., "Biosensors based on the energy metabolism of living cells: the physical chemistry and cell biology of extracellular acidification", Biosensors & Bioelectronics, vol. 7, pp. 255-272 (1992).

Owicki, J. C., "Probing receptor pharmacology and cell metabolism with a microphysiometer", Abstracts of papers of the American Chemistry Society, vol. 213, 9-SCHB (1997), Abstract.

Padalkar, S., et al., "Real-time fault diagnostics", IEEE Expert Intelligent Systems & Their Applications, vol. 6, pp. 75-85, (1991).

Patterson, C.E., et al., "Regulation of thrombin-induced endothelial cell activation by bacterial toxins", Blood Coagulation and Fibrinolysis, vol. 5, pp. 63-72 (1994).

Pelz, Oliver, et al., "Towards Elucidation of microbial community metabolic pathways: Unravelling the network of carbon sharing in a pollutant-degrading bacterial consortium by immunocapture and isotopic ratio mass spectrometry", Environmental Microbiology, vol. 1, No. 2, pp. 167-174 (1999).

Pizziconi, Vincent B., et al., "*A Cell-based immunobiosensor with engineered molecular recognition—Part I: design feasibility*" Biosensors & Bioelectronics, vol. 12, No. 4, pp. 287-299 (1997).

Prado, Alexandre G.S., et al., "*The influence of moisture on microbial activity of soils*", Thermochimica Acta, vol. 332, pp. 71-74 (1999).

Prokop, Aleš, "*Systems analysis and synthesis in biology and biotechnology*", Int. J. General Systems, vol. 8, pp. 7-31 (1982).

Prokop, Aleš, et al., "*Water soluble polymers for immunoisolation I: Complex coacervation and cytotoxicity*", Advances in Polymer Science, vol. 136 pp 1-51 (1998).

Prokop, Aleš, et al., "*Water soluble polymers for immunoisolation II: Evaluation of multicomponent microencupsulation systems*", Advances in Polymer Science, vol. 136 pp. 54-73 (1998).

Prokop, Aleš, Proposal submitted to National Institutes of Health, "*NanoBioReactor for monitoring small Cell Poulations*", NanoDelivery, Inc., dated Jul. 31, 2000.

Putley, E.H., "*Thermal detectors*", pp. 71-79.

Quake et al., U.S. Publication No. 2002/0012926, Publication date Jan. 31, 2002, U.S. Appl. No. 09/800,435, filed Mar. 5, 2001, "Combinatorial Array for Nucleic Acid Analysis".

Quake et al., U.S. Publication No. 2002/0034748, Publication date Mar. 21, 2002, U.S. Appl. No. 09/826,373, filed Apr. 4, 2001, "Methods and Systems for Molecular Fingerprinting".

Quake et al., U.S. Publication No. 2002/0037499, Publication date Mar. 28, 2002, U.S. Appl. No. 09/875,438, filed Jun. 5, 2001, "Integrated Active Flux Microfluidic Devices and Methods".

Quake et al., U.S. Publication No. 2002/0053532, Publication date May 9, 2002. U.S. Appl. No. 10/021,850, filed Dec. 13, 2001, "Method and Apparatus for Analysis and Sorting of Polynucleotides based on Size".

Quake et al., U.S. Publication No. 2002/0058332, Publication date May 16, 2002, U.S. Appl. No. 09/953,103, filed Sep. 14, 2001, "Microfabricated Crossflow Devices and Methods".

Reichert, U., et al., "*Heat evolution of cultured human keratinocytes*", Experientia, vol. 42, pp. 173-174 (1986).

Robinson, John M., et al., "*Production of active oxygen species by phagocytic leukocytes*", Immunol. Ser., vol. 60, pp. 159-178 (1994).

Roig, Teresa, et al., "*Microcalorimetric evaluation of the effect of combined chemotherapeutic drugs*", Biochimca et Biophysica Acta, vol. 1244, pp. 283290 (1995).

Rucktäschel, Anne K., et al., *Regulation by glucagon (cAMP) and insulin of the promoter of the human phosphoenolpyruvate carboxykinase gene (cytosolic) in cultured rat hepatocytes and in human hepatoblastoma cell's* Biochem. J., vol. 352, pp. 211-217 (2000).

Russell, S., "*A review of the applications of the thermal activity monitor (TMA) in metabolism, growth and the effects of stimulants and inhibitors on biological systems*", ThermoMetric, Application Note 22020 (1993).

Rustin, P., et al., "*Biochemical and molecular investigations in respiratory chain deficiencies*", Clinical Chimica Acta, vol. 228, pp. 35-51 (1994).

Saaski, Elric W., et al., "*Advanced flow immunoassay techniques*", Abstracts of Papers, Part 2, 213th ACS National Meeting: 0-8412-3500-7, American Chemical Society, San Francisco, CA (Apr. 13-17, 1997).

Schmidt, Christian, et al., "*A chip-based biosensor for the functional analysis of single ion channels*", Angew. Chem. Int. Ed., vol. 39, No. 17 pp. 3137-3140 (2000).

Schneider, Ilene, "*Preparing for a genomic world*", The Scientist, vol. 13, No. 4, pp. 6 (1999).

Schön, A., et al. "*The Use of microcalorimetry in studies of mammalian cells*", J. Thermal Anal., vol. 33, pp. 4750 (1988).

Schön, A., et al. "*Microcalorimetric measurement on tissue cells attached to microcarriers in stirred suspension*", J. Biochem and Biophys Methods, vol. 13, pp. 135-143 (1986).

Spence et al., U.S. Publication No. 2002/0005354, Publication date Jan. 17, 2002, U.S. Appl. No. 09/928,590, filed Aug. 13, 2001, "Microfabricated Cell Sorter".

Srinivas, U., et al., "*Staphylococcal enterotoxini-A-induced In-Vitro adhesion of HL-60 cells to endothelial cells involves both selecin and integrin families of cell adhesion molecules*", Scand. J. Immunol., vol. 48, pp. 127-135 (1998).

Steel, Karen P., "*The benefits of recycling*", Science, vol. 285, pp. 1363-1364 (1999).

Stephanopoulos, Gregory N., "*Metabolic engineering—principles and methodologies*", Academic Press, pp. 1-20 (Book).

Sturtevant, Julian M., "*Biochemical applications of differential scanning calorimetry*" Ann. Rev. Phys. Chem., vol. 38, pp. 463-488 (1987).

Tan, An-Min, et al., "*Microcalorimetric study of antiviral effect of drug*", J. Biochem. Biophys. Methods, vol. 38, pp. 225-228, (1999).

Tao, Han, et al., "*Functional genomics: Expression analysis of Escherichia coli growing on minimal and rich media*", J. Bacteriology, vol. 181, No. 20, pp. 64256440 (1999).

Teeling, H., "*Microbial degradation of tetraethyl lead in soil monitored by microcalorimetry*", Appl. Microbiol. Biotechnol., vol. 48, pp. 275-279 (1997).

Tessier, Philippe A., et al., "*Induction of acute inflammation in vivo by staphylococcal superantigens. II. Critical role for chemokines, ICAM-1, and TNF-α*", Journal of Immunology, vol. 161, pp. 1204-1211 (1998).

Thiellement, Hervé, "*Proteomics for genetic and physiological studies in plants*", Electrophoresis, vol. 20, pp. 20132026 (1999).

Thorén, Sven A., "*Calorimetry: A new quantitative in vitro method in cell toxicology. A dose/effect study of alveolar macrophages exposed to particles*", Journal of Toxicology and Environment Health, vol. 36, pp. 307-318 (1992).

Thorén, Sven A., et al., "*Microcalorimetric measurements of heat-production in rabbit alveolar macrophages*", Thermochimica Acta, vol. 72, pp. 117-122 (1984).

Thorén, Sven A., "*Operation of a multichannel microcalorimetry system in the micro-submicrowatt region: Some methodological aspects*", Journal of Biochemical and Biophysical Methods, vol. 18, pp. 149-156 (1989).

Tien, H. Ti, et al., "*Lipid bilayer-based sensors and biomolecular electronics*", Critical Reviews in Biomedical Engineering, vol. 18, No. 5, pp. 323-340 (1991).

Tolbert, William R. et al., "*Perfusion culture systems for production of mammalian cell biomolecules*", Monsanto Company, pp. 97-123, (Book).

Tomita, Masaru, et al., "*The E-CELL Project: Towards integrative simulation of cellular process*", New Generation Computing, vol. 18, pp. 1-12, (2000).

Tyagi, Sanjay, et al., "*Molecular beacons: probes that fluoresce upon hybridization*", Nat Biotechnol., vol 14, pp. 303-308 (1995).

Unger et al., U.S. Publication No. 2001/0029983, Publication date Oct. 18, 2001, U.S. Appl. No. 09/796,666, filed Feb. 28, 2001, "Microfabricated Elastomeric Valve and Pump Systems".

Unger et al., U.S. Publication No. 2001/0033796, Publication date Oct. 25, 2001, U.S. Appl. No. 09/796,871, filed Feb. 28, 2001, "Microfabricated Elastomeric Valve and Pump Systems".

Unger et al., U.S. Publication No. 2001/0054778, Publication date Dec. 27, 2001, U.S. Appl. No. 09/796,378, filed Feb. 28, 2001, "Microfabricated Elastomeric Valve and Pump Systems".

Unger et al., U.S. Publication No. 2002/0029814, Publication date Mar. 14, 2002, U.S. Appl. No. 09/826,583, filed Apr. 6, 2001, "Microfabricated Elastomeric Valve and Pump Systems".

Ussing, H. H., "*Membrane transport in biology*", Concepts and Models, Chapter 1, pp. 1-3 (1978).

Valdemarsson, Stig, et al., "*Increased ratio between anaerobic and aerobic metabolism in lymphocytes from hyperthyroid patients*", Eur. J. Endocrinol., vol. 130, pp. 267-280 (1994).

Valdemarsson, S., et al., "*Microcalorimetric study of myocardial tissue metabolism in heart failure after experimental myocardial infarction in rats*", Thermochimica Acta, vol. 286, pp. 131-137 (1996).

Valdemarsson, Stig, et al., "*Thyroid hormones and thermogenesis: a microcalorimetric study of overall cell metabolism in lympohcytes from patients with different degrees of thyroid dysfunction*", Acta Endocrinologica, vol. 123, pp. 155-160 (1990).

Verhaegen, Katarina, et al., "*A high-throughput silicon microphysiometer*", Sensors and Actuators, vol. 82, pp. 186-190 (2000).

Villani, Gaetano, et al., "*Low reserve of cytochrome c oxidase capacity in vivo in the respiratory chain of a variety of human cell types*", J. of Biol. Chem., vol. 273, No. 48, pp. 31829-31836 (1998).

Wadsö, I., "*On the accuracy of results from microcalorimetric measurements on cellular systems*", Thermochimica Acta, vol. 219, pp. 1-15 (1993).

Wadsö, Ingemar, "*Isothermal microcalorimetry for the characterization of interactions between drugs and biological materials*", Thermochimica Acta, vol. 267, pp. 45-59 (1995).

Wadsö, Ingemar, "*Microcalorimetric techniques for characterization of living cellular systems. Will there be any important practical application?*", Thermochimica Acta, vol. 269/270, pp. 337-350 (1995).

Wagner, M., et al., "*Induction of stress proteins in human endothelial cells by heavy metal ions and heat shock*", Am. J. Physiol., vol. 227 (Lung Cell. Mol. Physiol. vol. 21), pp. L1026-L1033 (1999).

Wallén-Öhman, Marie, et al., "*Antibody-induced apoptosis in a human leukemia cell line is energy dependent: thermochemical analysis of cellular metabolism*", Cancer Letters, vol. 75, pp. 103-109 (1993).

Wang, Taylor, et al., "*An encapsulation system for the immunoisolation of pancreatic islets*", Nature Biotechnology, vol. 15, pp. 358-362 (1997).

Westfall, Michael V., et al., "*Ultrastructure and cell-cell coupling of cardiac myocytes differentiating in embryonic stem cell culture*", Cell Motility and the Cytoskeleton, vol. 36, pp. 43-54 (1997).

Weygand, Markus, et al., "*Coupling of protein sheet crystals (S-layers) to phospholipid monolayers*", J. Mater. Chem., vol. 10, pp. 141-148 (2000).

Wieczorek, L., et al., "*A computer model of 2- and 3-dimensional kinetic process for a synthetic gated ion channel in tethered bilayer*", TH-Pos290, 41st Annual Meeting, Part 2 of 2, vol. 72, No. 2. (1997).

Wiley Carmen, et al., "*Continuous measurement of glucose utilization in heart myoblasis*", Anal. Biochem., vol. 304, pp. 139 146 (2002).

Wrontnowski, Cort, "*Conservative markets, radical technologies*" Industrial Biosensors, International Biotechnology Meeting & Exhibition, Article, (2000).

Zajtchuk, R., "*New Technologies in medicine: biotechnology and nanotechnology*", Disease-a-Month, vol. 45, pp. 453-495 (1999).

Zemel, Jay N., "*Future directions for thermal information sensors*", Sensors and Actuators A, vol. 56, pp. 57-62 (1996).

Zhang, Ping, et al., "*Serine/thereonine Phosphorylation in cellular signaling for alveolar macrophage phagocytic responseo endotoxin*", Shock, vol. 13, No. 1, pp. 34-40 (2000).

Bailey, James, E., "*Lessons from metabolic engineering for functiional genomics and drug discovery*", Nature Biotechnology, vol. 17, pp. 616-618 (1999).

Bailey, James E., "*Reflections on the scope and the future of metabolic engineering and its connections to functional genomics and drug discovery*", Metabolic Engineering, vol. 3, pp. 111-114 (2001).

Balcarcel, R. Robert, et al., "*Rapamycin reduces hybridoma cell death and enhances monoclonal antibody protection*", Biotechnology & Bioengineering, vol. 76, No. 1, pp. 1-10 (2001).

Bonarius, Hendrik, P., et al., "*Metabolic flux analysis of hybridoma cells in different culture media using mass balances*", Biotechnology & Bioengineering, vol. 50, No. 3, pp. 299-318 (1996).

Bonarius, Hendrik, P. J., et al., "*Metabolic-flux analysis hybridoma cells under oxidative and reductive stree using mass balances*", Cytotechnology, vol. 32, pp. 97-107 (2000).

Bonarius, Hendrik P. J., et al., "*Metabolic-flux analysis of continuously cultured hybridoma cells using $^{13}CO_2$ mass spectrometry in combination with $^{13}C$-Lactate nuclear magnetic resonance spectroscopy and metabolite balancing*" Biotechnology & Bioengineering, vol. 74, No. 6, pp. 528-538 (2001).

Bousse, Luc, "*Whole cell biosensors*", Sensors and Actuators B., vol. 34, pp. 270-275, (1996).

Campanella, L., et al., "*Further developments in toxicity cell biosensors*", Sensors and Actuators B, vol. 44, pp. 279-285 (1997).

Cao, C. J., et al., "*Validation of the cytosensor for in vitro cytotoxicity studies*", Toxicology in Vitro, vol. 11, pp. 285-293 (1997).

Cao, C. J., et al., "*Cytotoxicity of organophosphate anticholinesterases*", In Vitro Cell. Dev. Biol.—Animal, vol. 35, pp. 493-500 (1999).

Cao, C. J., et al., "*Toxicity of sea nettle toxin to human hepatocytes and the protective effects of phosphorylating and alkylating agents*", Toxicon, vol. 36, No. 2, pp. 269-281 (1998).

Connolly, Daniel T., et al., "*Determination of the number of endothelial cells in culture using an acid phosphatase assay*", Analytical Biochemistry, vol. 152, pp. 136-140 (1986).

Cornish-Bowden, Athel, et al., "*From genome to cellular phenotype—a role for metabolic flux analysis?*", Nature Biotechnology, vol. 18, pp. 267-268 (2000).

Cruz, Helder J., et al., "*Metabolic shifts by nutrient manipulation in continuous cultures of BHK cells*", Biotechnology and Bioengineering, vol. 66, No. 2, pp. 104-113 (1999).

D' Souza, S. F., "*Microbial biosensors*", Biosensors & Bioelectronics, vol. 16, pp. 337-353 (2001).

deZengotita, Vivian M., et al., "*Effects of $CO_2$ and osmolality on hybridoma cells: growth, metabolism and monoclonal antibody production*", Cytotechnology, vol. 28, pp. 213-227 (1998).

Dotsika, Eleni N., et al., "*A fluorometric assay for determining cell growth in lymphocyte proliferation and lymphokine assays*", Journal of Immunological Methods, vol. 105, pp. 55-62 (1987).

Drews, Jürgen, "*Drug Discovery: A historical perspective*", Science, vol. 287, pp. 1960-1964 (2000).

Edwards, Jeremy S., et al., "*How will bioinformatics influence metabolic engineering?*", Biotechnology & Bioengineering, vol. 58, Nos. 2/3, pp. 162-169(1998).

Europa, Anna F., "*Multiple steady states with distinct cellular metabolism in continuous culture of mammalian cells*", Biotechnology & Bioengineering, vol. 67, No. 1, pp. 25-34 (2000).

Follstad, Brian D., et al., "*Metabolic flux analysis of hybridoma continuous culture steady state multiplicity*", Biotechnology & Bioengineering, vol. 63, No. 6, pp. 675-683 (1999).

Gil, Geun Cheol, et al., "*A biosensor for the detection of gas toxicity using a recombinant bioluminescent bacterium*", Biosensors & Bioelectronics, vol. 15, pp. 23-30 (2000).

Gil, Geun Cheol, et al., "*Enhancement in the sensitivity of a gas biosensor by using an advanced immobilization of a recombinant bioluminescent bacterium*", Biosensors & Bioelectronics, vol. 17, pp. 427-432 (2002).

Girard, P., et al., "*Small-scale bioreactor system for process development and optimization*", Biochemical Enegineering Journal, vol. 7, pp. 117-119 (2001).

Glacken, M. W., et al., "*Reduction of waste product excretion via nutrient control: Possible strategies for maximizing product and cell yields on serum in cultures of mammalian cells*", Biotechnology & Bioengineering, vol. 28, pp. 1376 1389 (1986).

Gombert, Andreas Karoly, et al., "*Mathematical modelling of metabolism*", Current Opinion in Biotechnology, vol. 11, pp. 180-186 (2000).

Gross, Guenter W., et al., "*Odor, drug and toxin analysis with neuronal networks in vitro: Extracellular array recording of network responses*", Biosensors & Bioelectronics, vol. 12, No. 5, pp. 373-393 (1997).

Guardia, Maria Jesus, et al., "*Cybernetic modeling and regulations of metabolic pathways in multiple steady states of hybridoma cells*", Biotechnol. Prog., vol. 16, pp. 847-853 (2000).

Hirano, Seishiro, et al., "*Apoptotic cell death following exposure to fluoride in rat alveolar macrophages*", Arch Toxicol, vol. 70, pp. 249-251 (1996).

Hollis, R. P., et al., "*Design and application of a biosensor for monitoring toxicity of compounds to eukaryotes*", Applied & Environmental Microbiology, vol. 66, No. 4, pp. 1676-1679 (2000).

Hunt, L., et al., "*GFP-expressing mammalian cells for fast, sensitive, noninvasive cell growth assessment in a kinetic mode*", Biotechnology & Bioengineering, vol. 65, No. 2, pp. 201-205 (1999).

Janes, Lana E., et al., "*Quantitative screening of hydrolase libraries using pH indicators: Identifying active and enantioselective hydrolases*", Chem. Eur. J., vol. 4, No. 11 pp. 2324-2331 (1998).

Jauregui, Hugo, O., et al., "*Trypan blue dye uptake and lactate dehydrogenase in adult rat hepatocytes—freshly isolated cells, cell suspensions, and primary monolayer cultures*", In Vitro, vol. 17, No. 12, pp. 1100-1110 (1981).

Jeng, J.H., "*Cytotoxicity of sodium fluoride on human oral muscosal fibroblasts and its mechanisms*", Cell Biology & Toxicology, vol. 14, pp. 383-389 (1998).

John, Gernot Thomas, et al., "*Quantitative screening method for hydrolases in microplates using pH indicators: Determination of kinetic parameters by dynamic pH monitoring*", Biotechnology & Bioengineering, vol. 72, No. 6, pp. 620-627 (2001).

Jones, Laurie J., et al., "*Sensitive determination of cell number using the CyQUANT® cell proliferation assay*", J. Immunological Methods, vol. 254, pp. 85-98 (2001).

Kilburn, D. G., et al., "*The energetics of mammalian cell growth*", J. Cell Sci., vol. 4, pp. 645-654 (1969).

Koffas, M., et al., "*Metabolic engineering*", Annu. Rev. Biomed. Eng., vol. 1, pp. 535-557 (1999).

Korke, Rashmi, et al., "*Genomic and proteomic perspectives in cell culture engineering*", Journal of Biotechnology, vol. 94, pp. 73-92 (2002).

Kostov, Yordan, et al., "*Low-cost microbioreactor for high-throughput bioprocessing*", Biotechnology & Bioengineering, vol. 72, No. 3, pp. 346-352 (2001).

Lin, Jianqiang, et al., "*Metabolic flux change in hybridoma cells under high osmotic pressure*", Journal of Bioscience and Bioengineering, vol. 87, No. 2, pp. 255-257(1999).

Mattinelle, Kristina, et al., "*Elevated glutamate dehydrogenase flux in glucose-deprived hybridoma and myeloma cell: Evidence form $^1H/^{15}N\ NMR$*", Biotechnology and Bioengineering, vol. 60, No. 4, pp. 508-517 (1998).

Marty, J.-L., "*Biosensors for the detection of pesticides*", Analusis Magazine, vol. 26, No. 6, pp. M 144-M 149 (1998).

Moris-Varas, Francisco, "*Visualization of enzyme-catalyzed reactions using pH indicators: Rapid screening of hydrolase libraries and estimation of the enantioselectivity*", Bioorganic & Medicinal Chemistry, vol. 7, pp. 2183-2188 (1999).

Nadeau, I., et al., "*293SF metabolic flux analysis during cell growth and infection iwht an adenoviral vector*", Biotechnol. Prog., vol. 16, pp. 872-884 (2000).

Naessens, Martine, et al., "*Whole-cell biosensor for determination of volatile organic compounds in the form of aerosols*", Analytica Chimica Acta, vol. 364, pp. 153-158 (1998).

Naessens, Martine et al., "*Whole-cell biosensor for direct determination of solvent vapours*", Biosensors & Bioelectronics, vol. 13, Nos. 3/4, pp. 341-346 (1998).

Noiri, Eisei, et al., "*Permissive role of nitric oxide in endothelin-induced migration of endothelial cells*", The Journal of Biological Chemistry, vol. 272, No. 3, pp. 1747-1752 (1997).

Nyberg, Gregg, B., et al., "*Metabolism of peptide amino acids by chinese hamster ovary cells grown in a complex medium*", Biotechnology & Bioengineering, vol. 62, No. 3, pp. 324-335.

Owicki, J.C., et al., "*Biosensors based on the energy-metabolism of living cells—the physical—chemistry and cell biology of extracellular acidifcation*", Biosensor & Bioelectronics, vol. 7, No. 4, pp. 255-272 (1992) Abstract.

Paddle, Brian M., "*Biosensors for chemical and biological agents of defence interest*", Biosensors & Bioelectronics, vol. 11, No. 11, pp. 1079-1113 (1996).

Pancrazio, Joe, "*Preface*", Biosensors & Bioelectronics, vol. 16, pp. 427-428 (2001).

Pancrazio, J. J., et al., "*Development and application of cell-based biosensors*", Annals of Biomedical Engineering, vol. 27, pp. 697-711 (1999).

Pelster, B., et al., "*pH-dependent proton secretion in cultured swim bladder gas gland cells*", Am. J. Physiol., vol. 27 (Regulatory Integrative Comp. Physiol. vol. 42)pp. R1719-R1725 (1997).

Rudolph, Alan S., et al., "*Cell and tissue based technologies for environmental detection and medical dianostics*", Biosensors & Bioelectronics, vol. 16, pp. 429-431 (2001).

Sanders, Charlene A., et al., "*Stand-off tissue-based biosensors for the detection of chemical warfare agents using photosynthetic fluorescence induction*", Biosensors & Bioelectronics, vol. 16, pp. 439-446 (2001).

Sanfeliu, Anna, et al., "*Effect of glutamine limitation on the death of attached chinese hamster overy cells*", Biotechnology & Bioengineering, vol. 64, No. 1, pp. 46-53 (1999).

Sanfeliu, Anna, et al., "*Effect of insulin stimulation on the proliferation and death of chinese hamster ovary cells*", Biotechnology & Bioengineering, vol. 70, No. 4, pp. 421-427 (2000).

Savinell, Joanne, M., "*Network analysis of intermediary metabolism using linear optimization. I. Development of mathematical formalism*", J. Theor. Biol., vol. 154, pp. 421-454 (1992).

Schilling, Christophe, H., "*Metabolic pathway analysis: Basic concepts and scientific applications in the post-genomic era*", Biotechnol. Prog., vol. 15, pp. 296-303 (1999).

Shoji, R., et al., "*Development of a rapid and sensitive bioassy device husing human cells immobilized in macroporous microcarriers for the on-site evaluation of environmental waters*", Appl. Microbiol Biotechnol., vol. 54, pp. 432-438 (2000).

Shoji, Ryo, et al., "*Rapid bioassy of toxicity in environmental water by LDL-uptaking activity of human cell*", Wat. Sci. Tech., vol. 38, No. 7 pp. 271-278 (1998).

Shoji, Ryo., et al., "*A new assay for evaluating hepatotoxicity using LDL-uptake activity of liver cells*", Journal of Health Science, vol. 46, No. 6, pp. 493-502 (2000).

Stephanopoulos, Gregory, et al., "*After a decade of progress, an expanded role for metabolic engineering*", Advances in Biochemical Engineering/Biotechnology, vol. 73, pp. 1-8 (2001).

Stratowa, Christian, et al., "*A comparative cell-based high throughput screening strategy for the discovery of selective tyrosince kinase inhibitiors with anticancer activity*", Anti-Cancer Durg Design, vol. 14, pp. 393-402 (1999).

Taylor, D. Lansing, et al., "*Real-time molecular and cellular analysis: the new frontier of drug discovery*", Current Opinion in Biotechnology, vol. 12, pp. 75-81 (2001).

Vriezne, Nienke, et al., "*Fluxes and enzyme activities in central metabolism of myeloma cells grown in chemostat culture*", Biotechnology & Bioengineering, vol. 59, No. 1, pp. 28-39 (1998).

Wan, Chop P., et al., "*A simple fluorometric assay for the determination of cell numbers*", Journal of Immunological Methods, vol. 173, pp. 265-272 (1994).

Xie, Liangzhi, et al., "*Applications of improved stoichiometric model in medium design and fed-batch cultivation of animal cells in bioreactor*", Cytotechnology, vol. 15, pp. 17-29 (1994).

Xie, Liangzhi, et al., "*Energy metabolizm and ATP balance in animal cell cultivation using a stoichiometrically based reaction network*", Biotechnology & Bioengineering, vol. 52, pp. 591-601 (1996).

Yang, Te-Tuan, et al., "*An acid phosphatase assay for quantifying the growth of adherent and nonadherent cells*", Analytical Biochemistry, vol. 241, pp. 103-108 (1996).

Zupke, Craig et al., "*Intracellular flux analysis in hybridomas using mass balances and in vitro 13C NMR*", Biotechnology & Bioengineering, vol. 45, pp. 292-303 (1995).

Carslaw, H. S., et al., "*Conduction of heat in solids*", Second Edition (Book Prefaces and Contents) (1989).

Crosby E. J., et al., "*Experiments in transport phenomena*", Dept. of Chemical Engineering, The University of Wisconsin, John Wiley & Sons, Inc. (Book Prefaces and Contents) (1966).

Freshney, R. Ian, "*Culture of animal cells (A manual of basic technique)*", Wiley-Liss (Book Prefaces and Contents) (2000).

* cited by examiner

900

| | Device | Meas | Agents | | |
|---|---|---|---|---|---|
| | | | Ricin | VX | Unknown |
| Neuron | PicoCalorimeter | Temp | Levl + 5%, SNR 20 | Levl - 10%, SNR 3 | |
| Neuron | NanoBioReactor | pO2 | | Levl 10%, SNR 2 | Levl 10%, SNR 2 |
| Neuron | NanoBioReactor | Redox | Slope>10 SNR 20 | Slope>20 SNR 5 | Slope <0 SNR 2 |
| Neuron | NanoBioReactor | pH | Lev + 25%, SNR 4 | Lev + 25%, SNR 4 | Lev + 25%, SNR 4 |
| Neuron | AutoPatchClamp | Na+ | Lev + 10 SNR 3 | Lev - 10 SNR 3 | Lev + 10 SNR 3 |
| Neuron | AutoPatchClamp | K+ | Lev + 15 SNR 3 | Lev + 5 SNR 3 | Lev - 15 SNR 3 |
| Neuron | AutoPatchClamp | Ca++ | Lev + 8 SNR 2 | Lev + 8 SNR 2 | Lev + 8 SNR 2 |
| Neuron | Optical Tags | GFP & | Int + SNR 2 | Int + SNR 2 | Int - SNR 2 |
| Neuron | Optical Tags | FP | Int - SNR 4 | Int + SNR 4 | Int - SNR 2 |
| Neuron | Optical Tags | DNA | Pos SNR 7 | Pos SNR 7 | Pos SNR 2 |
| Neuron | Optical Tags | RNA | Neg SNR 2 | Neg SNR 2 | Neg SNR 2 |
| MyoCyte | | | Lev- SNR 4 | Lev- SNR 4 | Lev- SNR 4 |
| MyoCyte | | | Lev- SNR 2 | Lev- SNR 2 | Lev- SNR 2 |
| MyoCyte | | | Lev- SNR 4 | Lev- SNR 4 | Lev- SNR 4 |
| MyoCyte | | | Lev- SNR 6 | Lev- SNR 6 | Lev- SNR 6 |
| MyoCyte | | | Lev. SNR 4 | Lev. SNR 4 | Lev. SNR 4 |
| MyoCyte | | | Lev. SNR 2 | Lev. SNR 2 | Lev. SNR 2 |
| MyoCyte | | | Lev. SNR 6 | Lev. SNR 6 | Lev. SNR 6 |
| MyoCyte | | | Lev. SNR 4 | Lev. SNR 4 | Lev. SNR 4 |

APPARATUS AND METHODS FOR MONITORING THE STATUS OF A METABOLICALLY ACTIVE CELL

CROSS-REFERENCE TO RELATED APPLICATION

This application claims priority to U.S. Provisional Application Ser. No. 60/310,652, which was filed on Aug. 6, 2001, in the United States Patent and Trademark Office, and is incorporated herein by reference in its entirety.

This application is related to the following five U.S. patent applications with Ser. No. 10/212,918, filed Aug. 6, 2002, by Wikswo et al., which status is pending; Ser. No. 10/755,639, filed Jan. 12, 2004, by Wikswo et al., which is now issued as U.S. Pat. No. 7,435,578; Ser. No. 10/483,466, filed Sep. 7, 2004, by Cliffel et al., which status is pending; Ser. No. 10/483,461, filed Mar. 3, 2005, by Wikswo et al., which status is pending; and Ser. No. 10/510,500, Mar. 7, 2005, by Wikswo et al., which status is pending, respectively. All the above-identified applications were filed with the same assignee as that of this application, and claimed priority to U.S. Provisional Application Ser. No. 60/310,652, filed Aug. 6, 2001, by Wikswo et al. The disclosures of the above identified applications are incorporated herein by reference in their entireties.

The present invention was made with Government support under Grant No. N66001-01-C-8064 awarded by the Defense Advanced Research Projects Administration. The United States Government may have certain rights to this invention pursuant to these grants.

Some references, which may include patents, patent applications and various publications, are cited and discussed in the description of this invention. The citaion and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

FIELD OF THE INVENTION

The present invention generally relates to an apparatus and methods for using biological material to discriminate an agent. More particularly, the present invention relates to an apparatus and methods that utilize a matrix of biological signatures. In one embodiment, the matrix has a plurality of elements and a dimension of N×M, where N is the total number of the plurality of cells and M is the total number of the plurality of measurable quantities. Thus, the matrix has in total N×M elements, where each element represents a biological signature of one of a plurality of cells in response to an agent, and each biological signature is one of a plurality of measurable quantities. The present invention comprises a method that includes the steps of constructing such a matrix of biological signatures, exposing at least one of the plurality of cells to an agent, measuring the measurable quantities of the at least one of the plurality of cells responsive to the agent, comparing the measured measurable quantities of the at least one of the plurality of cells responsive to the agent with the corresponding biological signatures of the matrix of biological signatures, and identifying the agent from the comparison. The measured measurable quantities can be stored for further processing, analyzing, feed-backing, or the like.

The invention also relates to an apparatus for using biological material to discriminate an agent. In one embodiment, the apparatus includes means for constructing a matrix of biological signatures having a plurality of elements, wherein each element represents a biological signature of one of a plurality of cells in response to an agent, each biological signature being one of a plurality of measurable quantities, and wherein the matrix has a dimension of N×M, N being the total number of the plurality of cells and M being the total number of the plurality of measurable quantities; means for exposing at least one of the plurality of cells to an agent. The apparatus further includes means for measuring the measurable quantities of the at least one of the plurality of cells responsive to the agent, means for comparing the measured measurable quantities of the at least one of the plurality of cells responsive to the agent with the corresponding biological signatures of the matrix of biological signatures, and means for identifying the agent from the comparison.

Certain embodiments of the present invention comprise apparatus and methods for monitoring the status of a cell that is metabolically active, wherein each metabolic activity of the cell is characterized by a characterization time. More particularly, the apparatus and methods comprise means and the step for measuring at least one metabolic activity of the cell at a time period shorter than a characterization time corresponding to the measured metabolic activity of the cell, respectively.

Certain other embodiments of the present invention comprise devices and methods for detecting the response of a plurality of cells to at least one analyte of interest. More particularly, the devices and methods comprise means and the steps for contacting the plurality of cells with a plurality of analytes of interest and simultaneously detecting the response of the plurality of cells to the plurality of analytes of interest, respectively.

Certain further embodiments of the present invention comprise devices and methods for device for monitoring status of at least one cell, wherein the cell has a membrane forming a substantially enclosed structure and defining an intracellular space therein. More particularly, the devices and methods comprise means and the steps for providing a medium into the intracellular space of the cell and measuring the response of the cell to the medium, respectively.

Certain other embodiments of the present invention comprise devices and methods for measuring response of at least one cell to a medium, the response of at least one cell to a medium being characterized by a reaction time. More particularly, a device of the present invention comprises a sensor that measures the response of the cell to the medium at a time period shorter than the reaction time.

Certain additional embodiments of the present invention comprise devices and methods for discriminating an agent. More particularly, the devices and methods comprise means and the steps for constructing a decision tree having a plurality of branches, each branch corresponding to at least one defined action, wherein each branch comprises a plurality of successive branches, each successive branch corresponding to at least one defined action, providing a conditioned environment sensitive to the agent, obtaining data from response of the agent to the conditioned environment, extracting features from the obtained data, selecting a branch from the decision tree corresponding to the features, performing on the features at least one defined action corresponding to the branch, producing a classification of the agent, and iteratively repeating any or all steps until the agent is discriminated, respectively.

Certain further embodiments of the present invention comprise devices and methods for discriminating an agent. More particularly, the devices and methods comprise means and the steps of providing a plurality of L parameters, L being an integer, each parameter being related to the status of the agent, fitting the plurality of L parameters into a set of ith order differential equations, i=1, . . . , N, N being an integer, obtaining a plurality of L features corresponding to L parameters, respectively, from the set of ith order differential equations, separating the L features into a plurality of classes with a corresponding confidence level, providing a plurality of L+1 parameters, each parameter being related to the status of the agent, fitting the plurality of L+1 parameters into a set of ith+1 order differential equations, obtaining a plurality of L+1 features corresponding to L+1 parameters, respectively, from the set of ith+1 order differential equations, separating the L+1 features into a plurality of classes with a corresponding confidence level, and iteratively repeating any or all steps until a plurality of classes for the agent is separated with a desired corresponding confidence level, respectively.

Certain other embodiments of the present invention comprise devices and methods for discriminating an agent. More particularly, the devices and methods comprise means and the steps for providing a broad spectrum assay having a plurality of L cell lines, L being an integer, each cell line being able to respond to the agent, measuring responses of cell line i, i=1, . . . , L, to the agent, separating the responses into class m, m=1, . . . , O, O being an integer and the total number of available classes, with a corresponding robustness factor, selecting cell line j, j=1, . . . , L but≠i, from the knowledge of class m, measuring responses of cell line j, j=1, . . . , L but≠i, to the agent, defining a set of feature extraction algorithms from the measured response of cell line j, j=1, . . . , L but ≠i, selecting cell line k, k=1, . . . , L but ≠i and ≠j, measuring responses of cell line k, k=1, . . . , L but ≠i and ≠j, to the agent, separating the responses into class n, n=1, . . . , O, O being an integer and the total number of available classes, with a corresponding robustness factor, and iteratively repeating any or all steps until a class for the agent with a desired robustness factor is obtained, respectively.

BACKGROUND OF THE INVENTION

The biological cell may act as a parallel processing, non-linear, multistate, analog computer. This analog computer can occupy a volume of less than $10^{-16}$ m$^3$ and is primarily powered only by sugars, fats, and oxygen. The complexity of these computers is evidenced by the attempts in the art to model ongoing biochemical processes based on *Mycoplasma genitalium*, a microbe with the smallest known gene set of any self-replicating organism. However, even this simplest model requires hundreds of variables and reaction rules, and a complete model even for a mammalian cell would be much more complex, requiring in excess of $10^5$ variables and equations.

Because the cell behaves as an analog computer, it can be programmed. Historically, a limited set of interventions has allowed physiologists and engineers to study living cells and characterize the feedback control systems that govern cell function. With the advent of genetic engineering, it is now possible to reprogram the genetic machinery of a cell, for example to turn a particular gene on or off, or to produce large quantities of a particular biochemical. However, there has been little efforts and progress for inserting man-made devices into the control system of a single living cell so as to convert the cell into a programmable computational engine.

Therefore, among other things, there is a need ID merge cellular biophysics, microcircuits and microfluidics, and information technology to create, among other things, programmable Microsystems that can be used for sensing, feedback, control and analysis of a single cell and/or an array of interconnected and instrumented living cells.

Additionally, current bio-sensors use biological molecules for specific agent detection via specific binding reactions. However, wide-spectrum detection is expensive, requiring a priori threat knowledge and a large quantity of specific cells. Assays are susceptible to overload from multiple threats and false detection and from non-pathogenic “spoof” organisms. Furthermore, addressing new threats involves a lengthy, costly design process. In addition, conventional assayslack cellular machinery to increase sensitivity.

Therefore, among other things, there is also a need to develop new systems and methods that are capable of providing a complete bio-functional signature of a CBW agent, environmental contaminant, unknown drug, or other threats for better, fast, sensitive accurate and efficient detection.

SUMMARY OF THE INVENTION

In one aspect, the present invention relates to a method for monitoring the status of a cell that consumes oxygen. In one embodiment, the method includes the steps of confining the cell in a sensing volume, measuring dynamically oxygen consumption of the cell, and determining the status of the cell from the measured oxygen consumption of the cell.

The oxygen consumption of the cell may change when an agent interacts with the cell, and the determining step of the method further includes the step of discriminating the agent from the response of the cell.

The oxygen consumption of the cell may change with time until the cell dies, and the determining step of the method further includes the step of deciding a metabolically inactive status corresponding to the death of the cell.

Moreover, the method further includes the step of maintaining the cell in a conditioned environment. The maintaining step includes the step of keeping the cell in a solution of media. The maintaining step further includes the step of providing the solution of media to the sensing volume.

In another aspect, the present invention relates to an apparatus for monitoring the status of a cell that consumes oxygen. In one embodiment, the apparatus includes means for confining the cell in a sensing volume, means for measuring dynamically oxygen consumption of the cell, and means for determining the status of the cell from the measured oxygen consumption of the cell.

The oxygen consumption of the cell may change when an agent interacts with the cell, and the determining means includes means for discriminating the agent from the response of the cell.

In one embodiment, the confining means includes a channel, a first valve and a second valve located apart from each other along the channel, each of the first valve and the second valve being independently actuatable to at least partially at least partially block the channel, and wherein when the first valve and the second valve are both actuated, the portion of the channel therebetween the first valve and the second valve forms the sensing volume. The first valve and the second valve each is pneumatically or electrically actuatable. Plenty of choices are available for each actuation mechanism. For examples, valves can be pneumatically actuatable through one or more peristaltic pumps, and valves can be electrically actuatable through one or more piezo bimorphs.

In another embodiment, the measuring means includes a first electrode having a detecting end and a base, the detecting end of the first electrode positioned proximate to the sensing volume for generating signals responsive to the oxygen consumption of the cell, a second electrode having a detecting end and a base, the detecting end of the second electrode positioned proximate to the sensing volume for generating signals responsive to the oxygen consumption of the cell, and a meter for measuring electric signals, the meter coupled electrically to the first electrode and the second electrode, wherein when a voltage is applied to the base of the first electrode and base of the second electrode, electric signals are detectable at the meter as a function of the concentration of oxygen in the sensing volume. The meter can be a potentiostat, and when a voltage is applied to the base of the first electrode and base of the second electrode, the voltage between the two electrodes detectable at the potentiostat is a function of the concentration of oxygen in the sensing volume. Alternatively, the apparatus further includes a reference electrode, and the meter can be an amperemeter, wherein when a voltage is applied to the base of the first electrode and base of the second electrode, a current is detectable at the amperemeter, the strength of the current being a function of the concentration of oxygen in the sensing volume.

In yet another embodiment, the determining means includes a computer coupled to the measuring means. The computer can have a controller or processor independently performing desired tasks. Additionally, the computer may communicate to a network.

In another aspect, the present invention relates to a method for monitoring the status of a cell. In one embodiment, the method includes the steps of confining the cell in a sensing volume, measuring dynamically intracellular or extracellular signaling of the cell, and determining the status of the cell from the measured intracellular or extracellular signaling of the cell.

In yet another aspect, the present invention relates to an apparatus for monitoring the status of a cell that consumes oxygen. In one embodiment, the apparatus includes means for confining the cell in a sensing volume, means for measuring dynamically intracellular or extracellular signaling of the cell, and means for determining the status of the cell from the measured intracellular or extracellular signaling of the cell. In one embodiment, means for measuring dynamically intracellular or extracellular signaling of the cell includes an optical detector.

In a further aspect, the present invention relates to a method for monitoring the status of a cell that consumes or produces energy. In one embodiment, the method includes the steps of confining the cell in a sensing volume, measuring dynamically energy consumption or production of the cell, and determining the status of the cell from the measured energy consumption or production of the cell.

The energy consumption or production of the cell may change when an agent interacts with the cell, and the determining step of the method in this embodiment includes the step of discriminating the agent from the response of the cell.

The energy consumption or production of the cell changes with time until the cell dies, and the determining step of the method in this embodiment includes the step of deciding a metabolically inactive status corresponding to the death of the cell.

Moreover, the method further includes the step of maintaining the cell in a conditioned environment. The maintaining step may include the step of keeping the cell in a solution of media. The maintaining step may further include the step of providing the solution of media to the sensing volume.

The energy consumption or production of the cell includes consumption or secretion of a chemical component by the cell that relates to the metabolic status of the cell, wherein the chemical component includes at least one selected from the group consisting of pH, K (potassium), oxygen, lactate, glucose, ascorbate, serotonin, dopamine, ammonia, glutamate, purine, calcium, and sodium.

In yet another aspect, the present invention relates to an apparatus for monitoring the status of a cell that consumes or produces energy. In one embodiment, the apparatus includes means for confining the cell in a sensing volume, means for measuring dynamically energy consumption or production of the cell, and means for determining the status of the cell from the measured energy consumption or production of the cell.

The energy consumption or production of the cell may change when an agent interacts with the cell, and the determining means of the present invention includes means for discriminating the agent from the response of the cell.

In one embodiment, the confining means of the present invention includes a channel, a first valve and a second valve located apart from each other along the channel, each of the first valve and the second valve being independently actuatable to at least partially at least partially block the channel, and wherein when the first valve and the second valve are both actuated, the portion of the channel therebetween the first valve and the second valve forms the sensing volume. The first valve and the second valve each is pneumatically or electrically actuatable.

In another embodiment, the measuring means of the present invention includes a first electrode having a detecting end and a base, the detecting end of the first electrode being positioned proximate to the sensing volume for generating signals responsive to the energy consumption or production of the cell, a second electrode having a detecting end and a base, the detecting end of the second electrode being positioned proximate to the sensing volume for generating signals responsive to the energy consumption or production of the cell, and a meter for measuring electric signals, the meter coupled electrically to the first electrode and the second electrode, wherein when a voltage is applied to the base of the first electrode and base of the second electrode, electric signals are detectable at the meter as a function of the energy consumption or production in the sensing volume. The meter can be a potentiostat, and when a voltage is applied to the base of the first electrode and base of the second electrode, the voltage between the two electrodes detectable at the potentiostat is a function of the energy consumption or production in the sensing volume. Alternatively, the apparatus further includes a reference electrode, and the meter can be an amperemeter, wherein when a voltage is applied to the base of the first electrode and base of the second electrode, a current is detectable at the amperemeter, the strength of the current being a function of the energy consumption or production in the sensing volume.

In yet another embodiment, the determining means includes a computer coupled to the measuring means. The computer can have a controller or processor independently performing desired tasks. Additionally, the computer may communicate to a network.

In yet a further aspect, the present invention relates to a method for monitoring the status of a cell that is metabolically active, wherein each metabolic activity of the cell is characterized by a characterization time. In one embodiment, the method includes the steps of confining the cell in a sensing volume, measuring at least one metabolic activity of the cell at a time period shorter than a characterization time corresponding to the measured metabolic activity of the cell, and determining the status of the cell from the measured metabolic activity of the cell.

The metabolic activity of the cell may change when at least one agent interacts with the cell, and the determining step includes the step of discriminating the at least one agent from the measured metabolic activity of the cell. The metabolic activity of the cell may comprise a temporal response and the temporal response of the cell is measured in at least two measurements, wherein the time between the measurements is shorter than the reaction time corresponding to the temporal response of the cell. Additionally, the determining step further includes the step of quantifying the agent from the measured metabolic activity of the cell.

The metabolic activity of the cell changes with time until the cell dies, and the determining step includes the step of deciding a metabolically inactive status corresponding to the death of the cell. The method further includes the step of maintaining the cell in a conditioned environment, wherein the maintaining step includes the step of keeping the cell in a solution of media. The maintaining step further includes the step of providing the solution of media to the sensing volume.

The metabolic activities of the cell include consumption or secretion of a chemical component by the cell that relates to the metabolic status of the cell, wherein the chemical component includes at least one selected from the group consisting of pH, K, oxygen, lactate, glucose, ascorbate, serotonin, dopamine, ammonia, glutamate, purine, calcium, and sodium.

In another aspect, the present invention relates to an apparatus for monitoring the status of a cell that is metabolically active, wherein each metabolic activity of the cell is characterized by a characterization time. In one embodiment, the apparatus includes means for confining the cell in a sensing volume, means for measuring at least one metabolic activity of the cell at a time period shorter than a characterization time corresponding to the measured metabolic activity of the cell, and means for determining the status of the cell from the measured metabolic activity of the cell.

The metabolic activity of the cell may change when an agent interacts with the cell, and the determining means includes means for discriminating the agent from the measured metabolic activity of the cell. The determining means may further include means for discriminating the agents from the measured metabolic activities of the cell. Additionally, the determining means may further include means for quantifying the agent from the measured metabolic activity of the cell.

Moreover, the apparatus further includes means for maintaining the cell in a conditioned environment, wherein the maintaining means includes means for keeping the cell in a solution of media. Furthermore, the maintaining means may include means for providing the solution of media to the sensing volume.

In yet another aspect, the present invention relates to a device for growing at least one cell, wherein each of cellular physiological activities of the cell is characterized by a reaction time. In one embodiment, the device includes a first substrate having side portions and a bottom portion to define a volume for receiving the cell, wherein the bottom portion comprising a membrane that has a first surface, an opposite second surface and a thickness and is flexible, a second substrate positioned opposite to the first substrate to define a first channel therebetween, wherein the first channel is in fluid communication with the volume, a sensor positioned underneath the second substrate for measuring at least one of cellular physiological activities of the cell, and a second channel defined in the first substrate and positioned underneath the volume, wherein the second channel is in fluid communication with a supply of fluid. When a fluid such as pressured air from an air pump in the second channel causes the membrane to be deflected, the motion of the membrane causes the cell to respond and the sensor measures the response of the cell. The device may further have a biocompatible coating layer applied to the first surface of the membrane. The cell can be attached to the membrane for growing.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

FIG. 9 shows a bio-functional signature matrix according to one embodiment of the present invention.

DETAILED DESCRIPTION OF THE INVENTION

Figure 1:
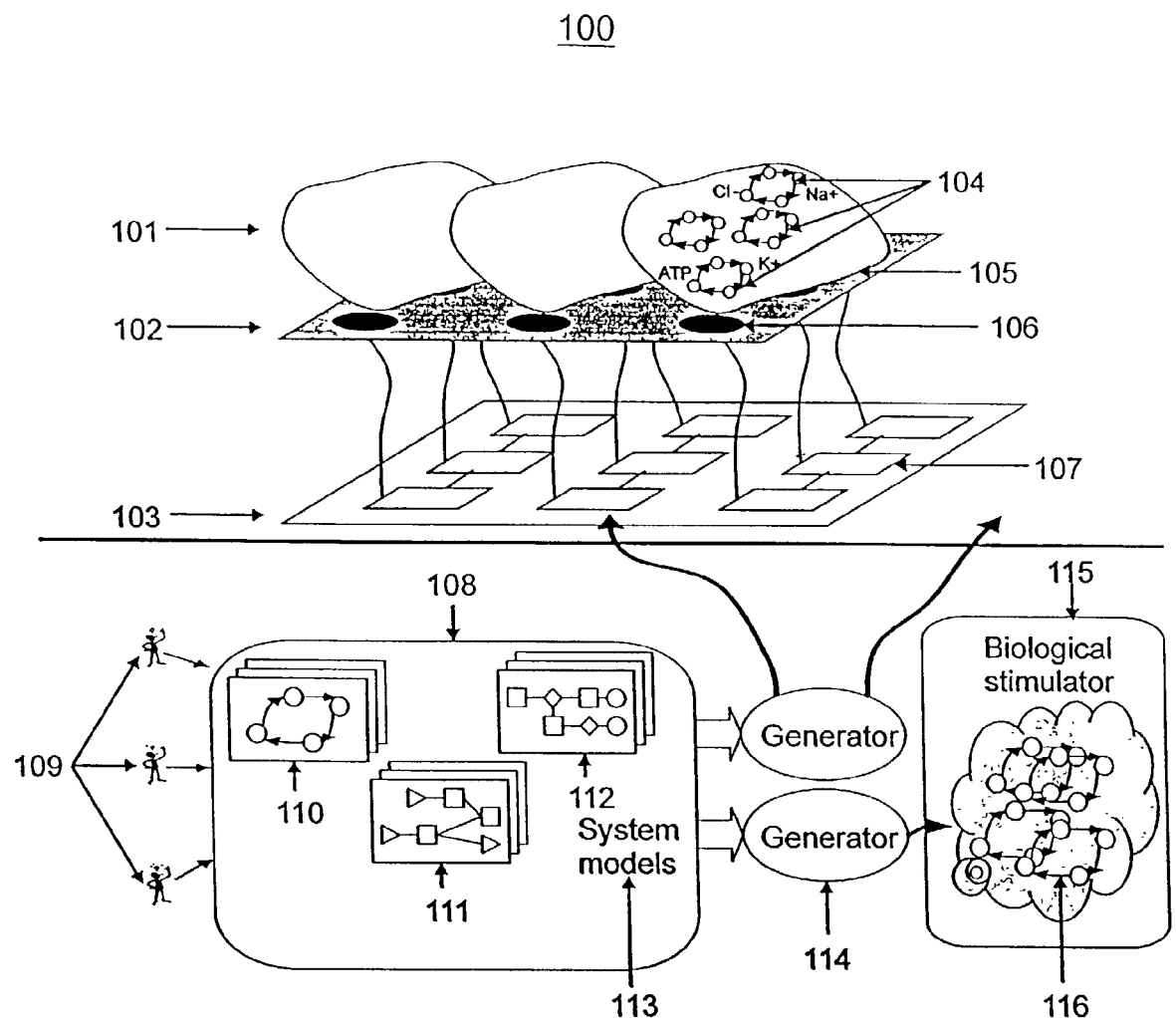
FIG. 1 schematically shows a multicellular bio-silicon hybrid microsystem according to one embodiment of the present invention.

Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

Definitions

The terms used in this specification generally have their ordinary meanings in the art, within the context of the invention, and in the specific context where each term is used. For example, conventional techniques of molecular biology, microbiology and recombinant DNA techniques may be employed in accordance with the present invention. Such techniques and the meanings of terms associated therewith are explained fully in the literature. See, for example, Sambrook, Fitsch & Maniatis. Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994). See also, PCR Protocols: A Guide to Methods and Applications, Innis et al., eds., Academic Press, Inc., New York (1990); Saiki et al., Science 1988, 239:487; and PCR Technology: Principles and Applications for DNA Amplification, H. Erlich, Ed., Stockton Press.

Certain terms that are used to describe the invention are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "about" or "approximately" shall generally mean within 20 percent, preferably within 10 percent, and more preferably within 5 percent of a given value or range.

Numerical quantities given herein are approximate, meaning that the term "about" or "approximately" can be inferred if not expressly stated.

The term "agent" is broadly defined as anything that may have an impact on any living system such as a cell. For examples, the agent can be a chemical agent. The chemical agent may comprise a toxin. The agent can also be a biological agent. Moreover, the agent may comprise at least one unknown component, which may be identified by practicing the present invention. Additionally, the agent may comprise at least one known component, whose interaction with cells or other components of an environment may be detected by practicing the present invention. The agent can also be a physical agent. Other examples of agent include biological warfare agents, chemical warfare agents, bacterial agents, viral agents, other pathogenic microorganisms, emerging or engineered threat agents, acutely toxic industrial chemicals ("TICS"), toxic industrial materials ("TIMS") and the like. Examples of chemical agents that may be related to practicing the present invention include Mustard (that may be simulated with chloroethyl ethyl sulphide (endothelia cells in PC)), GB Sarin (that may be simulated with Disopropylfluorophosphate (DFP)), VX (that may be simulated with Malathion) or the like. Examples of viral agents (and their simulants) that may be related to practicing the present invention include MS2, Hepatitus or simulant or attenuated virus, Retroviruses alphaviruses or the like. Examples of bacterial agents (and their simulants) that may be related to practicing the present invention include *Bacillus globigii* or *Bacillus subtilis* as spore formers similar to anthrax, *Erwinia herbicola* as a simulant for vegetative bacteria (not sporagenic), *E. coli* or the like. Additional examples of agents can also be found in the following exemplary list of agents:

Botulinum Toxin (seven immunological types: A, B, C1, C2, D, E, F, G)
  *Staphylococcus* enterotoxin B
  Saxitoxin
  Ricin (*Ricinus communis*)
  Epsilon toxin of *Clostridium perfringens*
  Mycotoxins
  Aflatoxins that inhibit DNA and RNA synthesis
  Anatoxin A
  Microcystins
  Cholera Toxin
  Tetrodotoxin
  Substance P
  *Bacillus anthracis* (Anthrax)
*Yersinia Pestis*, (gram-negative coccobacillus causing the zoonotic infection Plague)
*Clostridium botulinum*
*Francisella tularensis* (a gram-negative, facultative intracellular bacterium that causes the zoonosis Tularemia)
*Brucella* spp (spp=several different species?)
*Burkholderia mallei* (Glanders)
*Burkholderia pseudomallei*
*Chlamydia psittaci*
*Shigella dysenteriae*
*Salmonella* spp
*Vibrio cholerae*
*Cryptosporidium parvum*
*Clostridium perfringens*
Hepatitis C
Variola major (smallpox)
Filoviruses/Arenaviruses
Alphaviruses
Cephalomyelitis Viruses
Nipah Virus (a new paramyxovirus)
Hantavirus
Tick-borne hemorrhagic fevers
Dengue (Breakbone or Dandy Fever) fever virus
Enteric Viruses
Hepatcytes and Hepatitis A
Lymphocytes
Erythrocytes
Endothelial cells
HL1 (Cardiac)
Secretory cell (depolarize and it secretes things) Beta=insulin
PC12 neural cells
HELA (Helen Lane)
HEK293 Human Epithial Kidney cells
*Coxiella burnetti*
*Ricksettia prowazekii*
VX, V-gas
G-series (GF-cyclohexyl sarin, GD-Soman, GB-Sarin, GA-Tabun)
Mustard Agents
HN-1-Nitrogen Mustard
HN-2-Nitrogen Mustard (N-Oxide Hydrochloride)
Sulfar Mustard
Adamsite
Arsines
Lewisite
Hydrogen Cyanide
Cyanogen Chloride
BZ (Benzphetamine)
LSD (Lysergic Acid Diethylamide) (enable comment for this)
Chlorine
Phosgene
CN (2-Chloroacetophenone)
Fuel & Combustion Products (Jet Fuels)
JP-4
JP-8
TMPP
Herbicides/Pesticides
Methyl Parathion (an organophosphorus insecticide)
Volatile Organic Carbons (VOC)
Benzene
Toluene (methylbenzene)
Xylene
Heavy Metals
Lead
Chromium
Mercury
Halogens
Fluorine
Bromine
Cyanides
Isocyanates
cyanides (as CN)
Hydrogen Chloride
Sulfur Dioxide
Oxides of Nitrogen (NOx)
Vinyl Chloride
Barium Nitrate
Hydrazine
DBNP-di-tris-butyl-nitrophenol.

The term "toxin" is broadly defined as any agent that may have a harmful effect or harmful effects on any living system such as a cell. Examples of toxins that may be related to practicing the present invention include cyanide, endotoxin, okadaic acid, Phorbol Myristate Acetate ("PMA"), microcystin, Dinitrophenol ("DNP"), Botulinum toxin (a common threat agent; inhibit transmitter release, whole cell MB), *Staphylococcus* enterotoxin B, ricin (inhibits protein synthesis and ribosmone, OT), mycotoxins, aflatoxins, cholera toxin (activates Cl pump, vesicle MB, NBR), Saxatoxin or tetrodotoxin (Na channel blocker, vesicle MB), Microcystins (hepatocyte metabolism in PC) and organophosphates. Other examples of toxins may be also discussed somewhere else in the specification. Additional examples of toxins can also be found in the market. For example, the following is an exemplary list of toxins with their corresponding product number that are readily available from a commercial source.

| PRODUCT DESCRIPTION | PRODUCT NUMBER |
|---|---|
| Adenylate Cyclase Toxin from *Bordetella pertussis* | 188 |
| Alpha Toxin from *Staphylococcus aureus* | 120 |
| Anthrax Lethal Factor (LF), Recombinant from *Bacillus anthracis* | 171 |
| Anthrax Protective Antigen (PA), Recombinant from *Bacillus anthracis* | 172 |
| Anti-Choleragenoid, Goat Antibody for Cholera Toxin B Subunit | 703 |
| Anti-Exotoxin A, Goat Antibody for Exotoxin A from *Pseudomonas aeruginosa* | 760 |
| Anti-Toxin A, Goat Antibody for Toxin A from *Clostridium difficile* | 752 |
| Anti-VACh Transporter Saporin Conjugate | 770 |
| Biotin, Cholera Toxin B Subunit Conjugated | 112 |
| *Bordetella pertussis*, Adenylate Cyclase Toxin | 188 |
| *Bordetella pertussis*, Filamentous Hemagglutinin | 170 |
| *Bordetella pertussis*, Pertussis Toxin, Liquid in Glycerol Buffer | 179A |
| *Bordetella pertussis*, Pertussis Toxin, Lyophilized in Buffer | 180 |
| *Bordetella pertussis*, Pertussis Toxin, Lyophilized, Salt Free | 181 |
| *Bordetella pertussis*, Pertussis Toxin A Protomer | 182 |
| *Bordetella pertussis*, Pertussis Toxin B Oligomer | 183 |
| Botulinum Neurotoxin Type A from *Clostridium botulinum* | 130A |
| Botulinum Neurotoxin Type A Heavy Chain | 132 |
| Botulinum Neurotoxin Type A Light Chain | 131 |
| Botulinum Neurotoxin Type A Toxoid | 133 |
| Botulinum Neurotoxin Type B from *Clostridium botulinum* | 136A |
| Botulinum Neurotoxin Type B Heavy Chain | 138 |
| Botulinum Neurotoxin Type B Light Chain | 137 |
| Botulinum Neurotoxin Type B Toxoid | 139 |
| Cholera Toxin, Azide Free | 100 |
| Cholera Toxin from *Vibrio cholerae* | 101 |
| Cholera Toxin A Subunit | 102 |
| Cholera Toxin B Subunit | 103 |
| Cholera Toxin B Subunit, Low Salt | 104 |
| Cholera Toxin B Subunit Conjugated to Fluorescein Isothiocyanate | 106 |
| Cholera Toxin B Subunit Conjugated to Horseradish Peroxidase | 105 |
| Cholera Toxin B Subunit Conjugated to Tetramethylrhodamine B Isothiocyanate | 107 |
| Cholera Toxin B Subunit Conjugated to Phycoerythrin | 109 |
| Cholera Toxin B Subunit Conjugated to Biotin | 112 |
| Cholera Toxin B Subunit, Recombinant | 114 |
| *Clostridium botulinum*, Botulinum Neurotoxin Type A | 130A |
| *Clostridium botulinum*, Botulinum Neurotoxin Type A Heavy Chain | 132 |
| *Clostridium botulinum*, Botulinum Neurotoxin Type A Light Chain | 131 |
| *Clostridium botulinum*, Botulinum Neurotoxin Type A Toxoid | 133 |
| *Clostridium botulinum*, Botulinum Neurotoxin Type B | 136A |
| *Clostridium botulinum*, Botulinum Neurotoxin Type B Heavy Chain | 138 |
| *Clostridium botulinum*, Botulinum Neurotoxin Type B Light Chain | 137 |
| *Clostridium botulinum*, Botulinum Neurotoxin Type B Toxoid | 139 |
| *Clostridium botulinum*, Exoenzyme C3 | 143 |
| *Clostridium difficile*, Anti-Toxin A, Goat Antibody for Toxin A from *Clostridium difficile* | 752 |
| *Clostridium difficile*, Toxin A | 152 |
| *Clostridium difficile*, Toxin A Toxoid | 153 |
| *Clostridium difficile*, Toxin B | 155 |
| *Clostridium tetani*, Tetanolysin | 199 |
| *Clostridium tetani*, Tetanus Toxin | 190 |
| *Clostridium tetani*, Tetanus Toxin C-Fragment | 193 |
| *Clostridium tetani*, Tetanus Toxoid | 191 |
| *Corynebacterium diphtheriae*, Diphtheria Toxin CRM Mutant | 149 |
| *Corynebacterium diphtheriae*, Diphtheria Toxin, Unnicked | 150 |
| *Corynebacterium diphtheriae*, Diphtheria Toxoid | 151 |
| Diphtheria Toxin CRM Mutant | 149 |
| Diphtheria Toxin, Unnicked, from *Corynebacterium diphtheriae* | 150 |
| Diphtheria Toxoid | 151 |
| Enterotoxin Type B from *Staphylococcus aureus* | 122 |
| *Escherichia coli* J5 (Rc), Lipopolysaccharide | 301 |
| *Escherichia coli* K12, D31m4, Primarily Diphosphoryl Lipid A | 402 |
| *Escherichia coli* K12, D31m4 (Re), Lipopolysaccharide | 302 |
| *Escherichia coli* K12 strain LCD25, [$^3$H]Lipopolysaccharide | 510 |
| *Escherichia coli* K12 strain LCD25, Lipopolysaccharide | 314 |
| *Escherichia coli* O111:B4, Lipopolysaccharide | 201 |
| *Escherichia coli* O55:B5, Lipopolysaccharide | 203 |
| *Escherichia coli*, Stable Toxin | 118 |

-continued

| PRODUCT DESCRIPTION | PRODUCT NUMBER |
| --- | --- |
| Exoenzyme C3 from *Clostridium botulinum* | 143 |
| Exotoxin A from *Pseudomonas aeruginosa* | 160 |
| Filamentous Hemagglutinin from *Bordetella pertussis* | 170 |
| Fluorescein Isothiocyanate, Cholera Toxin B Subunit Conjugated | 106 |
| Fluorescein Isothiocyanate, Tetanus Toxin C-Fragment Conjugated | 196 |
| Horseradish Peroxidase, Cholera Toxin B Subunit Conjugated | 105 |
| Horseradish Peroxidase, Tetanus Toxin C-Fragment Conjugated | 195 |
| Lipid A from *Escherichia coli* K12, D31m4, Primarily Diphosphoryl | 402 |
| Lipid A from *Salmonella minnesota* R595, Primarily Monophosphoryl | 401 |
| [$^3$H]Lipopolysaccharide from *Escherichia coli* K12 strain LCD25 | 510 |
| Lipopolysaccharide from *Escherichia coli* J5 (Rc) | 301 |
| Lipopolysaccharide from *Escherichia coli* K12, D31m4 (Re) | 302 |
| Lipopolysaccharide from *Escherichia coli* K12 strain LCD25 | 314 |
| Lipopolysaccharide from *Escherichia coli* O111:B4 | 201 |
| Lipopolysaccharide from *Escherichia coli* O55:B5 | 203 |
| Lipopolysaccharide from *Salmonella minnesota* R595 (Re) | 304 |
| Lipopolysaccharide from *Salmonella typhimurium* | 225 |
| Lipopolysaccharide, Ultra Pure from *Salmonella minnesota* R595 (Re) | 434 |
| Neuraminidase from *V. cholerae* | 600 |
| Pasteurella Multocida Toxin | 156 |
| Pertussis Toxin, Liquid in Glycerol Buffer from *Bordetella pertussis* | 179A |
| Pertussis Toxin, Lyophilized in Buffer | 180 |
| Pertussis Toxin, Lyophilized, Salt Free | 181 |
| Pertussis Toxin A Protomer | 182 |
| Pertussis Toxin B Oligomer | 183 |
| *Pseudomonas aeruginosa*, Anti-Exotoxin A, Goat Antibody for Exotoxin A from *Pseudomonas aeruginosa* | 760 |
| *Pseudomonas aeruginosa*, Exotoxin A | 160 |
| Recombinant Adenylate Cyclase Toxin from *Bordetella pertussis* | 188 |
| Recombinant Cholera Toxin B Subunit | 114 |
| Recombinant protective antigen (PA) from *Bacillus anthracis* | 171 |
| Recombinant lethal factor (LF) from *Bacillus anthracis* | 172 |
| *Salmonella minnesota* R595, Primarily Monophosphoryl, Lipid A | 401 |
| *Salmonella minnesota* R595 (Re), Lipopolysaccharide | 304 |
| *Salmonella typhimurium*, Lipopolysaccharide | 225 |
| Shiga Like Toxin 1 (Verotoxin 1) | 163 |
| Shiga Like Toxin 2 (Verotoxin 2) | 164 |
| SNAPtide ™ Peptide Substrate for *C. botulinum* | 134 |
| Stable Toxin from *Escherichia coli* | 118 |
| *Staphylococcus aureus*, Alpha Toxin | 120 |
| *Staphylococcus aureus*, Enterotoxin Type B | 122 |
| Tetanolysin from *Clostridium tetani* | 199 |
| Tetanus Toxin from *Clostridium tetani* | 190 |
| Tetanus Toxin C-Fragment | 193 |
| Tetanus Toxin C-Fragment Conjugated to Fluorescein | 196 |
| Tetanus Toxin C-Fragment Conjugated to Horseradish Peroxidase | 195 |
| Tetanus Toxoid from *Clostridium tetani* | 191 |
| Tetramethylrhodamine B Isothiocyanate, Cholera Toxin B Subunit Conjugated | 107 |
| Toxin A from *Clostridium difficile* | 152 |
| Toxin A Toxoid from *Clostridium difficile* | 153 |
| Toxin B from *Clostridium difficile* | 155 |
| Tritiated Lipopolysaccharide from *Escherichia coli* K12 strain LCD25 | 510 |
| Verotoxin 1 (Shiga Like Toxin 1) | 163 |
| Verotoxin 2 (Shiga Like Toxin 2) | 164 |
| *Vibrio cholerae*, Anti-Choleragenoid, Goat Antibody for Cholera Toxin B Subunit | 703 |
| *Vibrio cholerae*, Cholera Toxin | 101 |
| *Vibrio cholerae*, Cholera Toxin, Azide Free | 100 |
| *Vibrio cholerae*, Cholera Toxin A Subunit | 102 |
| *Vibrio cholerae*, Cholera Toxin B Subunit | 103 |
| *Vibrio cholerae*, Cholera Toxin B Subunit, Low Salt Recommended for Tract Tracing | 104 |

It will be appreciated that all these toxins, in addition to other toxins given in the specification, are given as specific examples of toxins that may be related to practicing the present invention. Other known or unknown toxins can also be related to or used and may be preferred for certain, particular applications.

The term “molecule” means any distinct or distinguishable structural unit of matter comprising one or more atoms, and includes for example polypeptides and polynucleotides.

“DNA” (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. “RNA” (ribonucleic acid) means any chain or sequence of the chemical building blocks adenine (A), guanine (G), cytosine (C) and uracil (U), called nucleotide bases, that are linked together on a ribose sugar backbone. RNA typically has one strand of nucleotide bases.

As used herein, “cell” means any cell or cells, as well as viruses or any other particles having a microscopic size, e.g. a size that is similar to that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. As used herein, a cell is generally living unless otherwise indicated. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate). Cell or a plurality of cells can also comprise cell lines. Example of cell lines include liver cell, macrophage cell, neuroblastoma cell, endothelial cell, intestine cell, hybridoma, CHO, fibroblast cell lines, red blood cells, electrically excitable cells, e.g. Cardiac cell, myocytes (AT1 cells), cells grown in co-culture, NG108-15 cells (a widely used neuroblastoma X glioma hybrid cell line, ATCC# HB-12317), primary neurons, a primary cardiac myocyte isolated from either the ventricles or atria of an animal neonate, an AT-1 atrial tumor cardiac cell, Liver cells are also known as Hepatocytes, Secretory cell (depolarize and it secretes things) pancreatic beta cells secrete insulin, HELA cells (Helen Lane), HEK293 Human Epithial Kidney c, Erythrocytes (primary red blood cells), Lymphocytes and the like. Each cell line may include one or more cells, same or different. For examples, the liver cell comprises at least one of Human hepatocellular carcinoma ("HEPG2") cell, CCL-13 cell, and H4IIE cell, the macrophage cells comprises at least one of peripheral blood mononuclear cells ("PBMC"), and skin fibroblast cells, the neuroblastoma cell comprises a U937 cell, the endothelial cell comprises a human umbilical vein-endothelial cell ("Huv-ec-c"), and the intestine cell comprises a CCL-6 cell.

A "reporter" is any molecule, or a portion thereof, that is detectable, or measurable, for example, by optical detection. In addition, the reporter associates with a molecule or cell or with a particular marker or characteristic of the molecule or cell, or is itself detectable, to permit identification of the molecule or cell, or the presence or absence of a characteristic of the molecule or cell. In the case of molecules such as polynucleotides such characteristics include size, molecular weight, the presence or absence of particular constituents or moieties (such as particular nucleotide sequences or restrictions sites). The term "label" can be used interchangeably with "reporter". The reporter is typically a dye, fluorescent, ultraviolet, or chemiluminescent agent, chromophore, or radio-label, any of which may be detected with or without some kind of stimulatory event, e.g., fluoresce with or without a reagent Typical reporters for molecular fingerprinting include without limitation fluorescently-labeled single nucleotides such as fluorescein-dNTP, rhodamine-dNTP, Cy3-dNTP, Cy5-dNTP, where dNTP represents DATP, dTTP, dUTP or dCTP. The reporter can also be chemically-modified single nucleotides, such as biotin-dNTP. Alternatively, chemicals can be used that react with an attached functional group such as biotin.

A "marker" is a characteristic of a molecule or cell that is detectable or is made detectable by a reporter, or which may be coexpressed with a reporter. For molecules, a marker can be particular constituents or moieties, such as restrictions sites or particular nucleic acid sequences in the case of polynucleotides. The marker may be directly or indirectly associated with the reporter or can itself be a reporter. Thus, a marker is generally a distinguishing feature of a molecule, and a reporter is generally an agent which directly or indirectly identifies or permits measurement of a marker. These terms may, however, be used interchangeably.

A "measurable quantity" is a physical quantity that is measurable by a device, or obtainable by simulations. For examples, a measurable quantity can comprise a physical quantity related to cellular physiological activities of a cell exposed to an agent. Because cellular physiological activities of a cell involve a lot of activities across a wide spectrum, the plurality of physical quantities related to the impact of the agent on the cell physiology of the cell exposed to the agent are numerous such as heat production, oxygen consumption, uncoupling ratio between heat production and oxygen consumption, free radical synthesis, fraction of oxygen diverted to free radical synthesis, reduced nicotinamide adenine dinucleotide phosphate ("NAD(P)H"), acid production, glucose uptake, lactate release, gluconeogenesis, transmembrane potential, intracellular messengers, membrane conductance, transmembrane pump and transporter rates, messenger RNA expression, neurotransmitter secretion, intracellular glycolytic stores, transmembrane action potential amplitude and firing rate, heat-shock protein expression, intracellular calcium, calcium spark rate and the like.

The term "channel" is broadly defined as any ionic pathway that is associated with cellular physiological activities of a cell. There are various types of channels. For examples, a channel can be a Voltage-gated channel, a Ligand-gated channel, Resting K+ channels (that are inwardly rectifying K, leak channels), Stretch activated channels, Volume-regulated channels and the like. Examples of Voltage-gated channel include K, Na, Ca and Cl. Examples of Ligand-gated channel include Neurotranmitter (glutamate {NMDA, AMPA, KAINATE}, GABA, ACH (nicotinic), 5HT, glycine, histamine, Cyclic nucleotide-gated (cAMP, cGMP from inside of cell), some K-selective, some non-specific cation channels, G-protein activated (mostly potassium; pertussis toxin-inhibited), Calcium-activated (K channels activated by voltage and Ca) and the like.

A "sensor" is broadly defined as any device that can measure a measurable quantity. For examples, a sensor can be a thermal detector, an electrical detector, a chemical detector, an optical detector, an ion detector, a biological detector, a radioisotope detector, an electrochemical detector, a radiation detector, an acoustic detector, a magnetic detector, a capacitive detector, a pressure detector, an ultrasonic detector, an infrared detector, a microwave motion detector, a radar detector, an electric eye, an image sensor, any combination of them and the like. A variety of sensors can be chosen to practice the present invention.

A "controller" is broadly defined as any device that can receive, process and present information. For examples, a controller can be one microprocessor, several microprocessors coupled together, a computer, several computers coupled together, and the like.

The term "biosignature" means a marker for a particular signaling or metabolic pathway affected by an agent.

The term "analyte" means a material that can be consumed or produced by a cell. Examples of analyte of interest include pH, K, oxygen, lactate, glucose, ascorbate, serotonin, dopamine, ammonia, glutamate, purine, calcium, sodium, NADH (nicotinamide adenine dinucleotide), protons, insulin, NO (nitric oxide) and the derivatives of them.

The term "flow" means any movement of fluid such as a liquid or solid through a device or in a method of the invention, and encompasses without limitation any fluid stream, and any material moving with, within or against the stream, whether or not the material is carried by the stream. For example, the movement of molecules or cells through a device or in a method of the invention, e.g. through channels of a microfluidic chip of the invention, comprises a flow. This is so, according to the invention, whether or not the molecules or cells are carried by a stream of fluid also comprising a flow, or whether the molecules or cells are caused to move by some other direct or indirect force or motivation, and whether or not the nature of any motivating force is known or understood. The application of any force may be used to provide a flow, including without limitation, pressure, capillary action, electroosmosis, electrophoresis, dielectrophoresis, optical tweezers, and combinations thereof, without regard for any particular theory or mechanism of action, so long as molecules or cells are directed for detection, measurement or sorting according to the invention.

A "medium" is a fluid that may contain one or more agents, one or more analytes, or any combination of them. A medium can be provided with one or more analytes to be consumed by one or more cells. A medium can have one or more analytes generated by one or more cells. A medium can also have at the same time one or more analytes to be consumed by one or more cells and one or more analytes generated by one or more cells.

An "inlet region" is an area of a microfabricated chip that receives molecules or cells for detection measurement. The inlet region may contain an inlet channel, a well or reservoir, an opening, and other features which facilitate the entry of molecules or cells into the device. A chip may contain more than one inlet region if desired. The inlet region is in fluid communication with the main channel and is upstream therefrom.

An "outlet region" is an area of a microfabricated chip that collects or dispenses molecules or cells after detection, measurement. An outlet region is downstream from a discrimination region, and may contain branch channels or outlet channels. A chip may contain more than one outlet region if desired.

An "analysis unit" is a microfabricated substrate, e.g., a microfabricated chip, having at least one inlet region, at least one main channel, at least one detection region and at least one outlet region. A device of the invention may comprise a plurality of analysis units.

A "main channel" is a channel of the chip of the invention which permits the flow of molecules or cells past a detection region for detection (identification), or measurement. The detection and discrimination regions can be placed or fabricated into the main channel. The main channel is typically in fluid communication with an inlet channel or inlet region, which permit the flow of molecules or cells into the main channel. The main channel is also typically in fluid communication with an outlet region and optionally with branch channels, each of which may have an outlet channel or waste channel. These channels permit the flow of molecules or cells out of the main channel.

A "detection region" or "sensing volume" or "chamber" is a location within the chip, typically in or coincident with the main channel (or a portion thereof) and/or in or coincident with a detection loop, where molecules or cells to be identified, characterized, hybridized, measured, analyzed or maintained (etc.), are examined on the basis of a predetermined characteristic. In one embodiment, molecules or cells are examined one at a time. In other embodiments, molecules, cells or samples are examined together, for example in groups, in arrays, in rapid, simultaneous or contemporaneous serial or parallel arrangements, or by affinity chromatography.

A "branch channel" is a channel which is in communication with a discrimination region and a main channel. Typically, a branch channel receives molecules or cells depending on the molecule or cell characteristic of interest as detected by the detection region and sorted at the discrimination region. A branch channel may be in communication with other channels to permit additional sorting. Alternatively, a branch channel may also have an outlet region and/or terminate with a well or reservoir to allow collection or disposal of the molecules or cells.

A "gene" is a sequence of nucleotides which code for a functional polypeptide. For the purposes of the invention a gene includes an mRNA sequence which may be found in the cell. For example, measuring gene expression levels according to the invention may correspond to measuring mRNA levels. "Genomic sequences" are the total set of genes in a organism. The term "genome" denotes the coding sequences of the total genome.

"Preconditioning" is the process by which the physiological state of a cell or cells is adjusted by application of a known drug, toxin, analyte, or other chemical or physiological stimulus for the purpose of adjusting the response of the cell to a subsequently applied toxin. For example, if a cell is in a resting state, an agent that decreases metabolic level may not alter the cell's metabolism below the already-low resting state. But if the cell is preconditioned to be in a level of high metabolic activity, the subsequent application of that same agent would produce a much larger signal.

"Feedback" refers to the process by which a measured signal is amplified and transformed in a manner that it can be used to control or alter the property of the system in a manner that in turn affects the measured variable. Negative feedback would be feedback applied in a manner to reduce the amplitude of the measured variable. Positive feedback would be feedback applied in a manner to increase the amplitude of the measured variable.

"Actuator" is a device that can, under electrical, mechanical, or chemical control, or the like, perform an action in such a manner as to effect a change to a system. For example, a valve is an actuator that can control the release of an analyte.

"Feedback Control" is the process by which sensors and actuators are used to control the state of a system by means of positive or negative feedback, or both, such that the state of the system either remains constant in time or changes in accord with a desired sequence of changes. For example, the sensing of intracellular pH could be used to increase the flow of fluidic media into a cell to wash away the protons that are acidifying the sensing volume as a result of cell metabolism. As another example, a glucose sensor that detects a decrease in the glucose level in the sensing volume could use an actuator to increase the inflow of glucose into the sensing volume to stabilize the glucose levels to which the cell is exposed despite metabolic changes that affect the cell's utilization of glucose. The feedback signal can in turn provide direct information about, for example, the glucose consumption of the cell.

"Reaction time" is the time that a system of interest requires to respond to a change. For example, the reaction time of a cell is the time required for at least one of the physiological processes of a cell to adapt or respond to the application of an agent. The reaction time of a sensor is the time required for the sensor to respond to a change in the quantity that it is sensing. For example, the reaction time of an electrochemical sensor is set by the size of the sensor and the thickness and nature of protective coatings on the activated surfaces of the sensor. The reaction time of a microfluidic system is determined by the reaction time of the cell to changes in the environment, the time required for chemical species to diffuse throughout the sensing volume, the reaction time of the sensor(s), the reaction time of the actuators and the diffusion time of the analyte being controlled by the actuators. It follows that stable feedback control of a physiological parameter requires that the diffusion, sensor and actuator reaction times are less than the reaction time of the cell.

Overview of the Invention

In one aspect, the present invention relates to a system and methods for using biological material to discriminate an agent. In one embodiment as shown in FIG. 1, a system 100 according to the present invention includes a plurality of cells 105, where each cell has multiple metabolic pathways 104 for metabolic events. The system 100 further includes a first structure 101 for receiving the plurality of cells to form a biolayer, where the first structure 101 has a plurality of sensing volumes, and each sensing volume is in a conditioned environment capable of receiving and maintaining at least one cell. As such formed, cells 105 may be coupled together and communicate to each other.

The system 100 additionally includes an array 102 of sensors 106 positioned underneath the biolayer 101 for simultaneously monitoring of multiple metabolic pathways 104 for each of the plurality of cells, where each metabolic pathway may be disturbed in the presence of an agent (not shown). The system 100 further includes at least one controller 107 coupled to each sensor 106 of the array 102. When an agent invades the conditioned environment, the array of the sensors 102 detects the changes of metabolic events for at least one of the cells and generates at least one signal in response, and the controller 107 receives the signal from the array of sensors 102 and identifies the agent from the signal. The controller 107 further includes means for quantifying the agent from the measured response. Thus, among other things, contrary to traditional approaches to discriminate an agent from testing the agent, one aspect of the present invention is to discriminate, and quantify, an agent from the response of a living cell to the agent.

Moreover, because a living cell behaves as an analog computer, it can be programmed. However, the cell controls its physiological status through an internal cellular control mechanism. Therefore, in order to program the cell, i.e. direct the cell to do what it is taught to do, the internal cellular control mechanism of the cell has to be overridden. Historically, a limited set of interventions has allowed physiologists and engineers to study living cells and characterize the feedback control systems that govern cell function. With the advent of genetic engineering, it is now possible to reprogram the genetic machinery of a cell, for example to turn a particular gene on or off, or to produce large quantities of a particular biochemical. However, as yet there has been little work on inserting man-made devices into the control system of a single living cell so as to convert the cell into a programmable computational engine. The present invention merges cellular biophysics, microcircuits and microfluidics, and information technology to create programmable Multicellular Bio-Silicon Hybrid Microsystems such as system 100 as shown in FIG. 1, which serve as biological computing engines having an array of interconnected and instrumented living cells with associated control and modeling software; and a biophysical infospace design environment required to program and analyze output from these Microsystems.

Thus, as shown in FIG. 1, in addition to sensors 106, the physical layer 102 may further include microbottles, picocalorimeters, microfluidics, and controllers, some of them according to the present invention are discussed in more detail below. Additionally, the system 100 has infolayer 102 that may have reconfigurable digital and analog software, programmable digital signal processors (DSPs) and at least one controller 107 (which may itself be a DSP), which provides an integrated computational structure to receive measurements and compute signal identification procedures to detect and identify agents including toxins, and control cellular actuators. Sensors 106 can be multispectral sensors that measure and transduce multiple cell parameters and control cell environmental parameters via actuators and effectors. The system 100 may further have a biophysical infospace design environment 108 that includes software CAD/CASE tools that allow user(s) 109 to design algorithms for the computational structure 113 which supports multiple customized interfaces for the users 109 who, for examples, may include microbiologists, hardware/sensor engineers, diagnostic experts and the like. The computational structure 113 includes system models such as cellular metabolic processes and modeling 110, physical sensor and effectors on the sensor system 111, and identification and diagnosis procedures and decision models 112. Software generators 114, which may be embedded in one or more computers such as a network, automatically convert models 110, 111, and/or 112 into executable code(s) to program the infolayer 103 including controller 107, which in turn communicates and controls with the biolayer 101 through the physical layer 102, and to drive biological simulators 115, whose output 116 can be used to verify algorithms and procedures defined in generators 114 prior to implementation in the biolayer 101, the physical layer 102, and the infolayer 103.

Accordingly, the system 100 provides a programmable cellular microsystem that has a true bi-directional, bioionic-silicon interface. Development of the system 100 and related devices involves not only the building of cell-based biosensors, but also the creation of biological and solid-state processes needed to form a functioning assembly of sensors and actuators. One challenge is to identify the computations or tasks for which this technology is best suited. Nevertheless, the present invention provides multiple biosilicon microsystems that can be combined to form larger analog biomicrocomputers capable of solving particular classes of problems with higher speed and lower power consumption than could be implemented in silicon and software.

In one application, the system 100 can be utilized to discriminate an agent. In one embodiment, at least one cell 105 is provided and is exposed to the agent, which may be contained in a medium, the response of the cell to the agent is measured in terms of a physical quantity related to at least one of the cellular physiological activities of the cell, and from the measured response the agent can be identified. Furthermore, the agent (such as its concentration in the medium) can be quantified from the measured response. When cell(s) are used as a canary to detect an agent, the present invention has the tremendous advantage of non-specificity, in that it reveals information only about overall cellular metabolic activity and hence it is not necessary to develop a particular sensor for each anticipated agent such as toxin.

In another embodiment, at least one cell is provided and is exposed to the agent, which may be contained in a medium, the response of the cell to the agent is measured, where the response of the cell to the agent is characterized by a reaction time, at a time period shorter than the reaction time, and from the measured response the agent can be identified. Furthermore, the agent (such as its concentration in the medium) can be quantified from the measured response. The response can take various forms including a temporal response of the cell to the agent, which is measured in at least two measurements. The time between the measurements is shorter than the reaction time corresponding to the temporal response of the cell. Indeed, as discussed below, among other things, one aspect of the present invention is that it provides devices and methods in which the diffusion time from the cell to the sensor is comparable to the response time of the sensor such that the response of the cell to the agent can be measured faster and better than what prior art could offer.

Exemplary devices and methods according to the embodiments of the present invention are given below. Note that titles or subtitles may be used in the examples for convenience of a reader, which in no way should limit the scope of the invention.

EXAMPLES

Example 1

Biosignatures Matrix

In one aspect of the present invention, a wide-spectrum, activity-detection technology is developed that employs several novel cell and membrane-based sensing technologies, in order to provide a complete bio-functional signature of a CBW agent, unknown drug, or other threat. The bio-functional signatures can be used with advanced algorithms to discriminate between different agents. The system and devices are extraordinarily versatile and general; because one unique feature of the present invention, among other things, is that the biological impact of the toxins is detected and measured, rather than the toxins themselves.

Today, biosensors use biological molecules (antibodies, enzymes, nucleic acids, etc.) for specific agent detection via specific binding reactions. Wide-spectrum detection is expensive, requiring a priori threat knowledge and a large quantity of specific cells. Assays are susceptible to overload from multiple threats and false detection and from non-pathogenic 'spoof' organisms. Furthermore, addressing new threats involves a lengthy, costly design process. In addition, conventional assays do not employ cellular machinery to increase sensitivity.

An alternative is to monitor the state of a set of optimized biological systems so that a departure from normal homeostasis sounds an alert of a possible CB attack. A broad set of physiological tests on a combination of receptor, ion-channel, cell, and tissue-based biosensors can provide a rapid, sensitive, and accurate differential diagnosis of cellular pathophysiology. One challenge is to develop sound methods for achieving clear signatures of the patho-physiological effects of CBW agents. This approach discerns both the identities of known CBW agents, and the mechanism of action for unknown agents. Such information will help guide countermeasures.

Accordingly, a spectrum of on-line biosensors for physiological responses in model systems or living cells are developed, in order to obtain and discriminate bio-functional signatures of CBW agents. These biosensors can measure heat generation, metabolic products, ion-channel conductance, transmembrane potential, intracellular conductance, the expression of optically tagged proteins for cardiac myocytes, neurons, and endothelial cells, and intracellular and intercellular signaling, which includes the secretion of neurotransmitters, hormones, and growth factors. These modalities are chosen to span the broad range of physiological mechanisms affected by the spectrum of possible CBW agents. The multiphasic measurements can be used to track toxin-induced, temporal responses, and test hypotheses regarding prophylactic or therapeutic measures in support of a differential diagnosis.

Referring now to FIG. 9, in one embodiment, the present invention relates to a method for using biological material to discriminate an agent. A matrix of biological signatures 900 constructed according to one embodiment of the present invention is shown in FIG. 9. Matrix 900 conceptually represents a hypothetical table or process used to specify cell species, measurement methods, and expected/measured responses for definition of identification algorithms related to the discrimination of agents. As shown in FIG. 9, column 901 represents cell species, i.e., cells, which are utilized to discriminate an agent. Column 902 represents devices that are used to make corresponding measurements, where each measurement measures a biological signature of one of a plurality of cells in response to an agent. Note that while some of devices given in column 902 are examples according to embodiments of the present invention, which are disclosed in this specification, other devices and even some existing technologies can be utilized to practice the present invention. Column 903 represents measurable quantities or attribute/product to be measured. Column 904 represents outputs of the measurements, i.e., the expected or measured response of the cell/attribute for each of the agents of interest, including the change from nominal/steady state for a cell and the signal-to-noise of the measurement. Furthermore, the matrix 900 is an open-ended, i.e., it can be expanded to include specifications for additional cell types 905 as well as identification for additional agents 906. In other words, the total number of elements for column 902 (number of cells), N, the total number of elements for column 903 (number of measurable quantities) and even total number of elements for agents 906 (number of agents) are adjustable. It means that, for example, it does not require the development of specific assays to new agents such as known or unknown toxin threats. This generality arises because the present invention allows one to measure the biological impact of toxins rather than the toxins themselves.

Figure 9A:
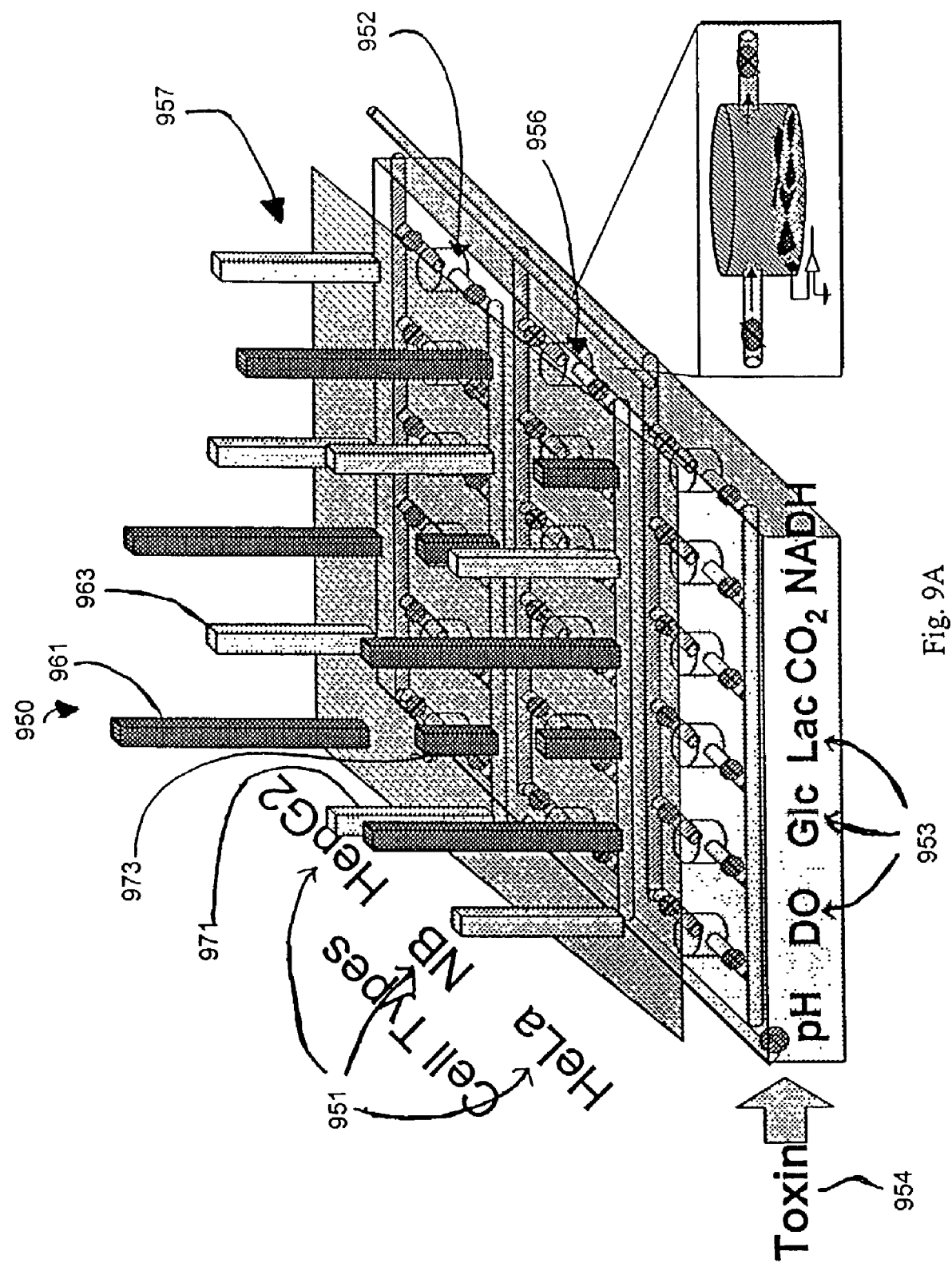
FIG. 9A schematically shows a bio-functional signature matrix of FIG. 9 in another form according to one embodiment of the present invention.

FIG. 9A shows a matrix of biological signatures 950 constructed according to another embodiment of the present invention. As shown in FIG. 9A, matrix 950 has a dimension of N×M, where N represents cell species or cell lines such as HeLa, NB, and HepG2. Each cell line may have a number of cells participating. Thus, N may also reflect the total number of cells that are utilized to discriminate an agent. M represents the total number of the plurality of measurable quantities such as pH, DO, Glucose, Lac, $CO_2$, NADH as shown in FIG. 9A. When the one or more cells 951 are exposed to an agent such as a toxin, one or more measurable quantities 953 of the one or more cells responsive to the agent are measured, generating a plurality of outputs 957. Each of the outputs 957 is an element of the matrix 950 that represents a biological signature corresponding to a particular cell responsive to the agent. For examples, element 961 represents the measurement of analyte pH for an HepG2 cell responsive to toxin 954, element 963 represents the measurement of analyte DO for an HepG2 cell responsive to toxin 954, etc. The measured measurable quantities of the plurality of cells 951 responsive to the toxin 954, i.e., outputs 957, can then be compared with the corresponding biological signatures of the matrix 950, which can be obtained through calibrating the matrix from a plurality of chemical agents once the matrix is formed and stored in a model data base. From the comparison, the toxin can be identified. Note that each output 957 has amplitude, from which the toxin can be quantified through the comparison, which is another unique feature of the present invention over the existing technologies. The measured measurable quantities, outputs 957, can be stored in a database associated with a memory device (not shown) for further processing, analyzing, feedbacking, or the like.

Outputs 957 can be obtained in several ways. In one embodiment, for example, one can start to measure element 961 in the first row, then element 963, until all elements in the first row of the matrix 950 have been measured. Then, one can continue to measure element 971 in the second row, then element 973, until all elements in the second row of the matrix 950 have been measured. This process is repeated for the rest rows of the matrix 950 until all biology signatures corresponding to the elements in all N rows of the matrix have been measured. This process of measurements may be termed as an orthogonal measurement. Note that the elements in all N rows of the matrix can be measured simultaneously. Alternatively, the elements in all N rows of the matrix can be measured in sequence, or any way one chooses to proceed. It will be appreciated that the method described above is just one of many ways to get the elements of the matrix measured. For example, one is free to pick any element of the matrix as a starting point to measure. Alternatively, one can pick several (up to all) elements of the matrix to be measured simultaneously.

Calibration(s) may be performed before the measurements. Moreover, before the measurements, preconditioning agents may be applied to the cells 951 to place the cells in a desired physiological state. Cells 951 can be placed in one or more chambers 958. Each chamber 958 may receive one or more cells. Additionally, during the measurements, a medium containing analytes may be supplied to cells in each chamber so as to maintain a preconditioned environment to keep the cells of interest alive. Different chambers may receive different mediums in term of content through proper fluid control. Moreover, the exposure of the cells to the agent needs to be kept under a threshold of exposure for irreversible cell damage or cell death to keep the cells of interest alive. The exposure of the cells to the agent can be adjusted according to the measured measurable quantities. Some or all of the activities discussed above can be coordinated, performed, or processed by a computer or a computer associated with a network.

Outputs 957 can be obtained through various apparatus. In one embodiment as shown in FIG. 9A, a sensor array 952 is utilized to measure the measurable quantities of at least one of the plurality of cells responsive to the agent. Sensor array 952 includes a plurality of sensors, which may be same or different. Some or all of them may be devices provided by the present invention such as sensor 956, which is a NanoPhysiometer as discussed in more detail below. Sensor array 952 may be considered as a matrix of sensors corresponding to the matrix of biological signatures 900.

Figure 10:
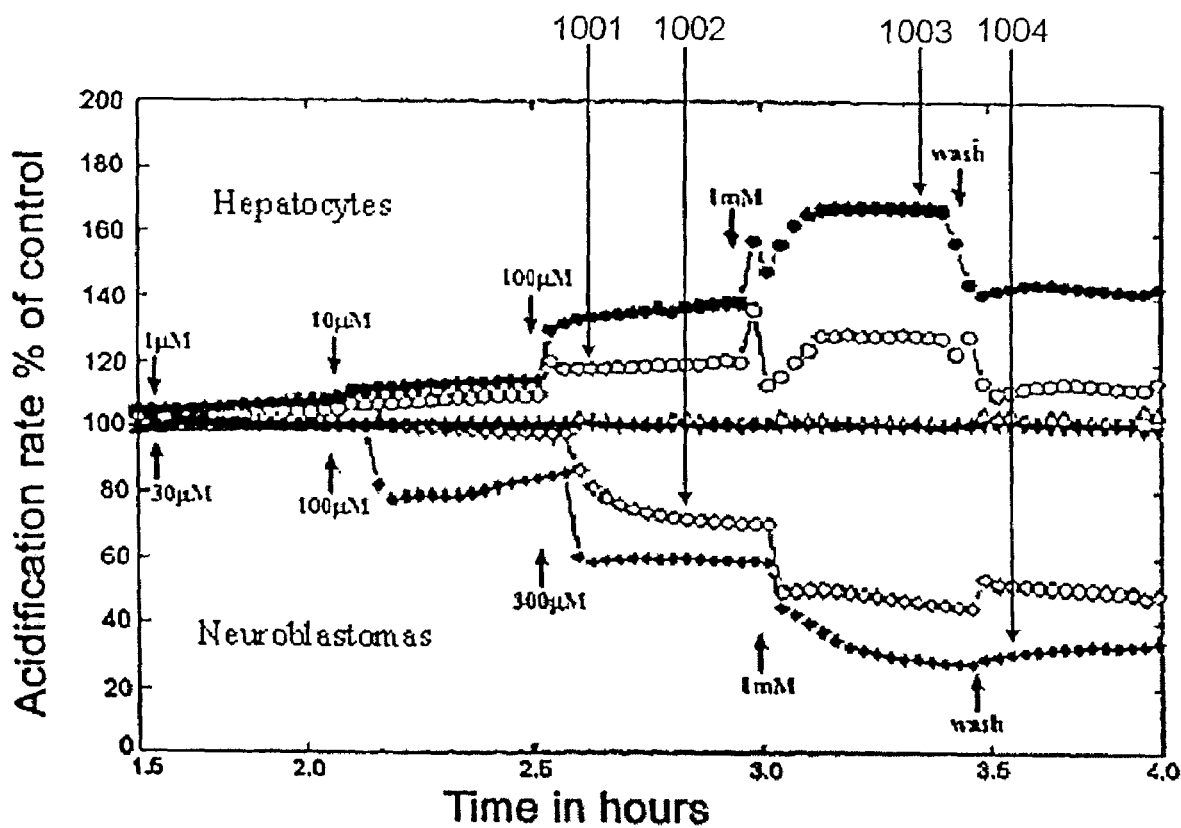
FIG. 10 shows data of parathion (open symbols) and paraoxon (filled symbols) on metabolic activity of human hepatocyte and neuroblastoma cells according to one embodiment of the present invention.

Referring now to FIG. 10, response of cells to certain toxin is shown. In FIG. 10, measured acidification rate of cultured cells, when exposed to a stepped increase in a toxin, followed by washout. Line 1001 represents acidification response of hepatocytes to parathion. Line 1002 represents response of hepatocytes to paroxon. Line 1003 represents response of neuroblastomas to parathion. And line 1004 represents response of neuroblastomas to paroxon. FIG. 10 shows the dose response of a change in pH induced by agents in cell cultures of μL volumes. FIG. 10 uses published data of parathion (open symbols) and paraoxon (filled symbols) on metabolic activity of human hepatocyte and neuroblastoma cells obtained with a commercially available CytoSensor™ instrument, which also shows that commercially available instruments may be modified and utilized to practice the present invention.

Figure 15:
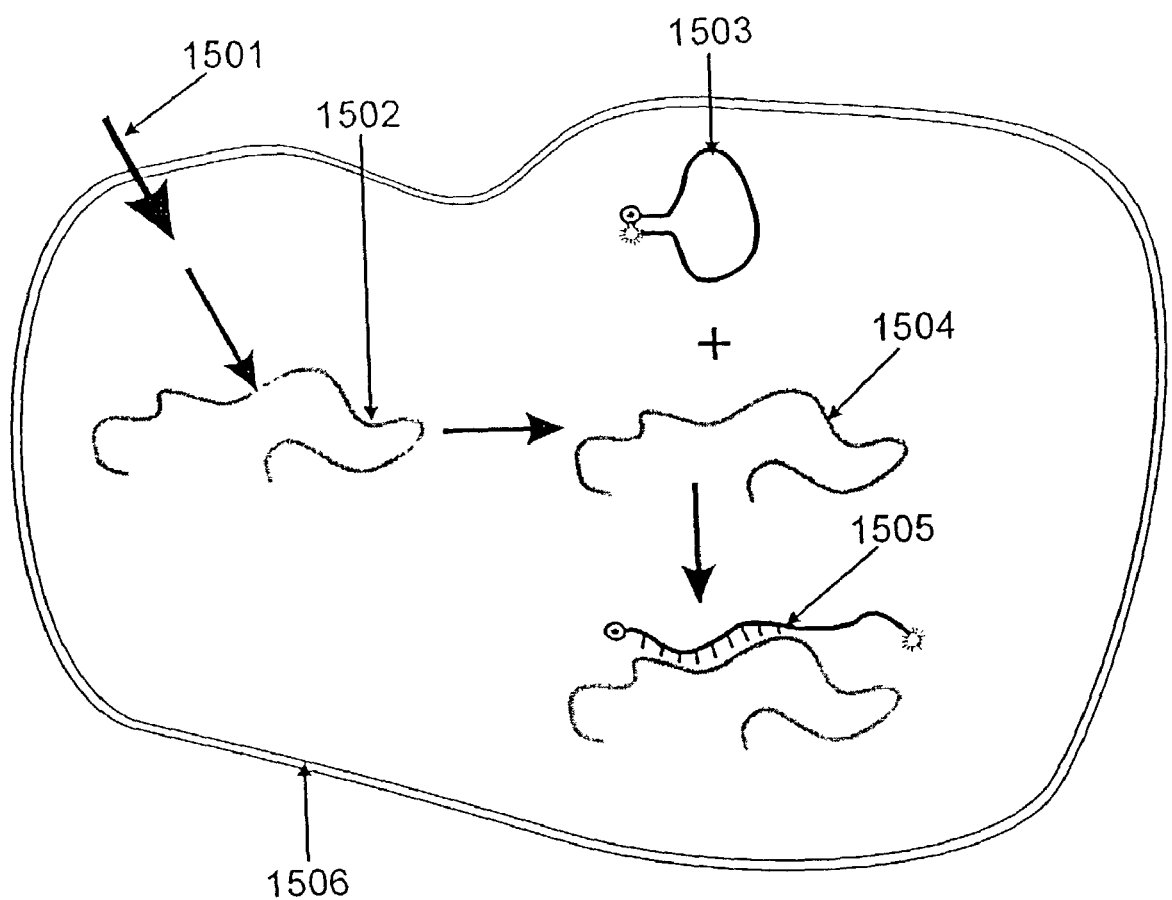
FIG. 15 schematically shows response of optical beacons to a binding event as a means to identify the expression of particular mRNA in response to toxins and agents according to one embodiment of the present invention.
Figure 16:
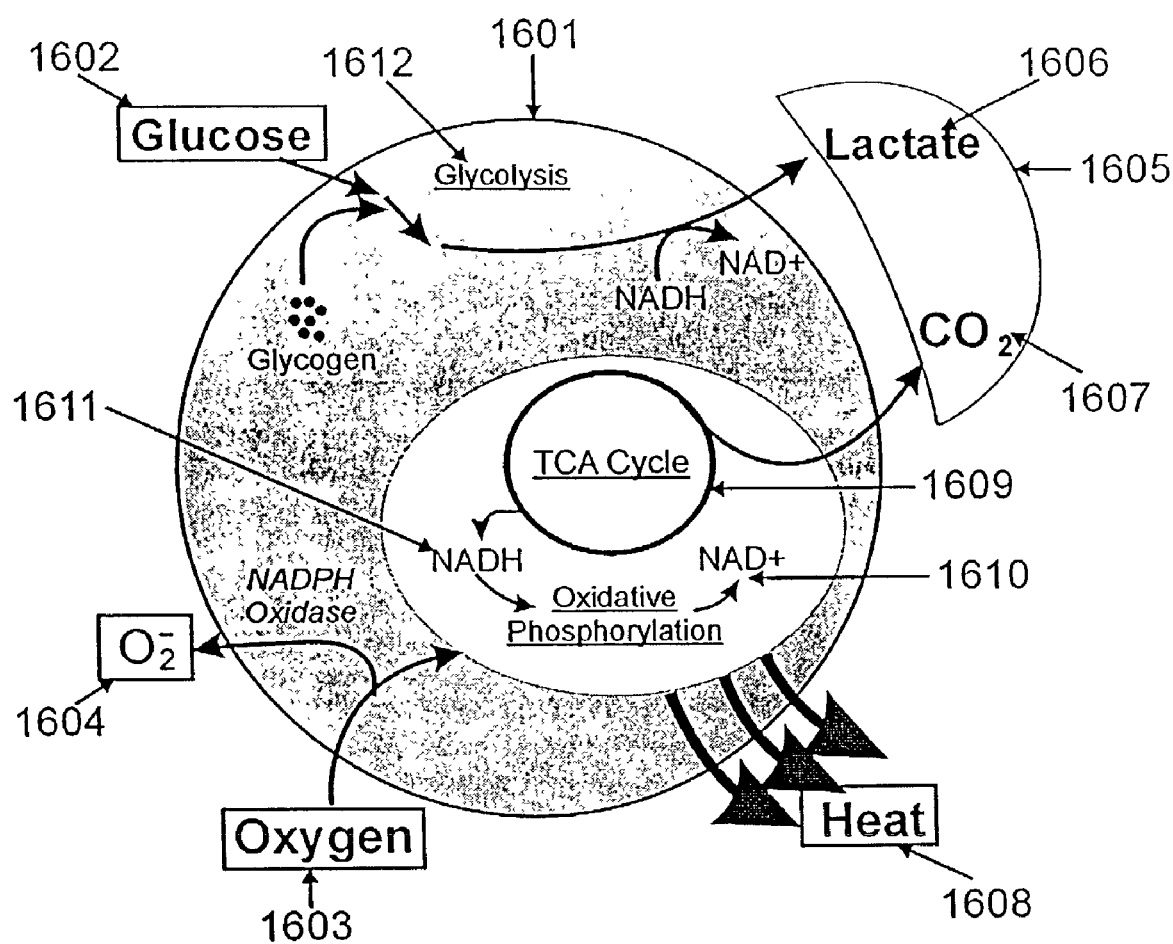
FIG. 16 illustrates an example of cellular pathways that can be monitored according to one embodiment of the invention.

FIG. 15 shows the response of optical beacons to a binding event as a means to identify the expression of particular mRNA in response to toxins and agents. Upon exposure to Interferon-Y at 1501, synthesis of mRNA is triggered at 1502. The resulting mRNA 1504 then binds with a molecular beacon 1503 in a manner that the ends of the molecular beacon are no longer in close proximity, so that the resulting beacon-mRNA complex fluoresces 1505. FIG. 16 schematically indicates that when hybridized with a complementary oligonucleotide, the hairpin structure linearizes, distancing the fluorophore and quencher to yield fluorescence. In other words, existing optical molecular beacon technology can also be utilized practice the present invention.

An example of cellular pathways can be monitored with discrimination matrix 950 and sensor array 957 of the present invention. Cellular processes are metabolically-driven, energy-requiring events. The basal energy requirements are derived from the oxidation of metabolic substrates, e.g., glucose 1602, either by oxidative phosphoralation 1611 involving the aerobic TCA or Kreb's cycle 1609 or anerobic glycolysis 1602. When glycolysis is the major source of energy, the metabolic activity of cells can be estimated by monitoring the rate at which the cells excrete acidic products of metabolism 1605, e.g., lactate 1606 and $CO_2$ 1607. In the case of aerobic metabolism, the consumption of extracellular oxygen 1603 and the production of oxidative free radicals 1604 are reflective of the energy requirements of the cell. Intracellular oxidation-reduction potential can be measured by autofluorescent measurement of the NADH 1611 and $NAD^+$ 1610 ratio. The amount of energy, e.g., heat 1608, released by the cell is derived from analytical values for substances produced and/or consumed during metabolism which under normal settings can be predicted from the amount of oxygen consumed (4.82 kcal/l $O_2$). The coupling between heat production and oxygen utilization can be disturbed by toxins. Direct microcalorimetry measures the temperature rise of a thermally isolated sample. Thus when combined with measurements of oxygen consumption calorimetry can used to detect the uncoupling activity of toxins. The devices disclosed in this specification are designed to measure, among other things, the following variables: glucose 1602, lactate 1606, $CO_2$ 1607, NADH 1611 and $NAD^+$ 1610 ratio, heat 1608, $O_2$ consumption 1603, and free-radical production 1604. Some metabolic activities of cells of interest are listed in the following Table 1.1.

TABLE 1.1

| | |
|---|---|
| Glucose + 2 ADP + 2 $NAD^+$ | → 2 Pyruvate + 2 ATP + 2 NADH |
| Pyruvate + NADH | → Lactate + $NAD^+$ |
| Pyruvate + CoA + FAD + GDP + 3 $NAD^+$ + $NAD(P)^+$ | → 3$CO_2$ + FADH2 + GTP + 3 NADH + NAD(P)H |
| 0.5 $O_2$ + 3 ADP + NADH | → 3 ATP + $NAD^+$ |
| 0.5 $O_2$ + 2 ADP + $FADH_2$ | → 2 ATP + FAD |

The energy requiring events within the cells are sensitive to the availability of energy in the form of ATPase and NADH (NADPH) to sustain the activity. Those energy-consuming events include maintenance of the membrane potential, intracellular pH, and osmotic balance. Moreover, many of the cell signaling events that control cell growth, programmed cell death (apoptosis), cellular cytoskeleton and cell specific function (e.g., immune response of macrophages and gluconeogenesis and albumin synthesis by hepatocytes) are very sensitive to metabolic stress. Thus, one aspect of the present invention is to take advantage of the unique characteristics of cells to develop signatures that will allow for discrimination. For example, the sodium potassium ATPase, which is the major consumer of ATPase in the resting cell, is reliant on adequate cellular ATPase availability to maintain a transmembrane potential. Without this potential, cell viability is dramatically compromised. Toxins that target the pump or the cellular ATPase levels will produce identifiable and measurable signatures.

The approach to monitor specific metabolic pathways has the tremendous advantage of non-specificity, in that it reveals information about overall cellular metabolic activity and hence it is not necessary to develop a particular sensor for each anticipated toxin. Yet by monitoring specific features of the metabolic response in multiple cells types, we can define the discrimination algorithm. Clearly the response to a toxin can be cell specific. For example, the ECBC laboratory demonstrated that parathion and paraoxon have opposite effects on hepatocyte and neuroblastoma cell metabolism. The cell lines utilized in the present invention include, for examples, macrophages (PBMC, U937), liver (HEPG2,CCL-13, H4IIE), neural (HTB-11) and endothelial (HUV-ECC-C), and intestinal (CCL-6) cells. They represent cells that are derived from organs, which are targets of biotoxins. The liver is a major target of toxins (aflotoxin, organophosphates, viral hepatitis) both because of its anatomical location, (i.e., is exposed to all toxins absorbed via the alimentary tract) and because it is metabolically active and plays such a central role in biodetoxification in the organism. The intestine is directly exposed to toxins (e.g., bacteria, virus, enterotoxin) entering via the oral route. Neuronal cells are targets of a number of toxins (organophosphates) that alter ion channel function.

Macrophages serve as one of the most important sentinels for the presence of many biotoxins. They are ideally located at the major routes of potential toxin entry: respiratory airways, intestine, liver and skin. The alveolar macrophage (AM) lives on the mammalian bronchial surfaces and is exposed to inhaled polluted air. Acting as a scavenger, it protects the pulmonary tissue from invading microorganisms and inhaled particles and hence is an ideal sentinel for air quality. Macrophages upon stimulation have a characteristic "respiratory burst". This is a manifest as a large increase in oxygen consumption and oxygen free radical production. The free radicals inactivate toxins such as viruses and bacteria. Given their robustness and the rapidity of the "respiratory burst" responses to toxins, macrophages can serve as early responders in the discrimination matrix 950.

Figure 17A:
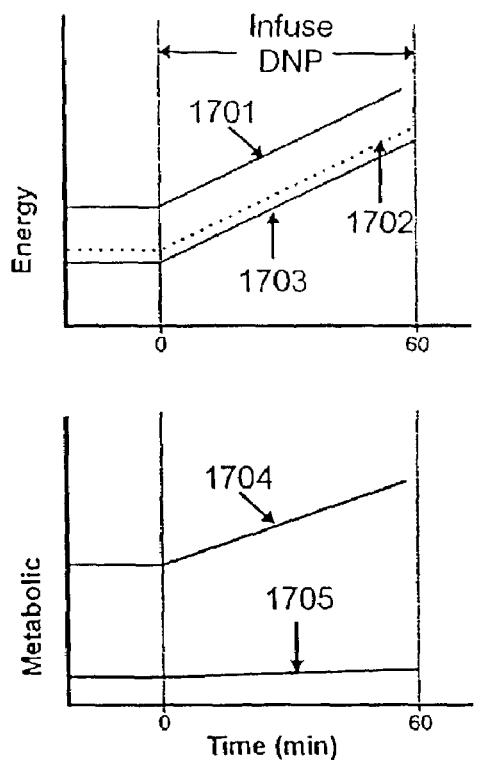
FIG. 17 illustrates an example of toxin discrimination by simultaneous monitoring of multiple metabolic signals following the exposure of cells to some toxins according to one embodiment of the invention: A. to DNP; and B. to Cyanide.
Figure 17B:
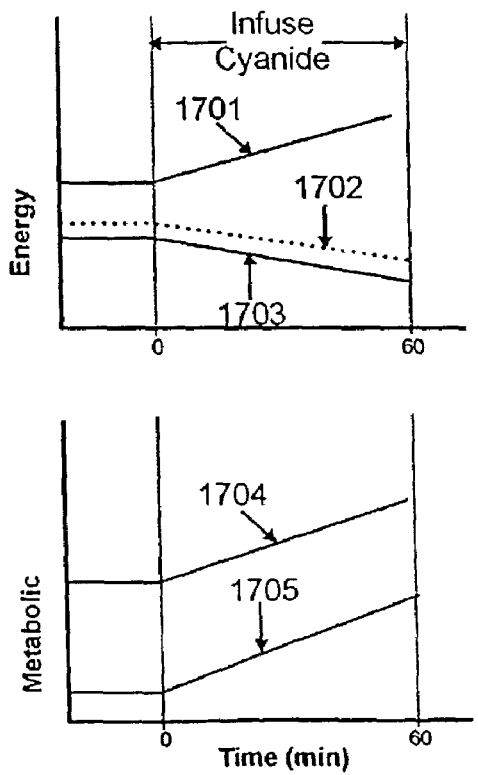

An example of toxin discrimination by simultaneous monitoring of multiple metabolic signals according to the present invention following the exposure of some toxins is shown in FIGS. 17A and 17B. FIGS. 17A and 17B illustrate how the discrimination of different analytes can be realized with a multi-sensor array of the present invention, and how one can deduce which metabolic pathways are targeted by the agent. In FIG. 17a, it shows an example of the physiological signatures (energy and metabolic) produced by the chemical Dinitrophenol (DNP), which uncouples ATPase synthesis from heat production and oxygen consumption. The result is that to perform the same cellular processes, more oxygen, represented by line 1703, is consumed and more heat, represented by line 1701, and carbon dioxide, represented by line 1702, are generated by less efficient systems such as glycolysis. Glucose uptake, represented by line 1704, increases significantly, but lactate release, represented by line 1705, increases only slightly. Thus, the physiological signature of DNP will be a rise of oxygen consumption and heat production. In the case of cyanide in FIG. 17b, the heat production 1711), glucose uptake 1714, and lactate release 1715 increase while $CO_2$ production 1712 and $O_2$ consumption 1715 decrease, respectively.

Generally in response to stress, the increase in heat production is driven by an increase in the metabolic requirements of the cell. This increase may be met by a general increase in oxygen consumption that is driven by an increase in mitochondrial respiration and oxygen consumption. The increase in caloric requirements can be met by a facilitation of glucose entry. The glucose can either enter the glycolytic pathway and be released as lactate or it can be completely oxidized to carbon dioxide and water via mitochondrial respiration. Depending on the site of action of the toxin, and the cell type, one or both pathways may be used. Some toxins (e.g., cyanide) target mitochondrial respiration. Thus, despite adequate oxygen availability, the cell is unable to use oxygen to make ATP. Thus, glycolysis (glucose conversion to lactate) serves a greater role in meeting the energy demands of the cell and the release of carbondioxide is not longer the primary fate of the glucose carbon and instead lactate release increases with glucose uptake. In contrast other agents such as DNP (dinitrophenol) decrease the efficiency of the mitochondrial process such that the oxygen requirements are greater for a given ATPase requirement of the cell. The result is that the cell consumes more oxygen and produces more heat to meet the ATPase demands. This may manifest as a unique signature whereby oxygen consumption and heat production both increase. To meet the increase in energy demands, glucose uptake is increased. In this case as shown in FIG. 17a, there will be a corresponding increase in CO2 production. However, that does not require the use of the inefficient glycolytic pathway to meet the cellular needs and lactate release will increase only slightly. Thus, unique biological signatures can be developed by tracing the time course and amount of glucose uptake and subsequent oxidation and/or conversion to lactate in response to a given toxin.

Figure 18A:
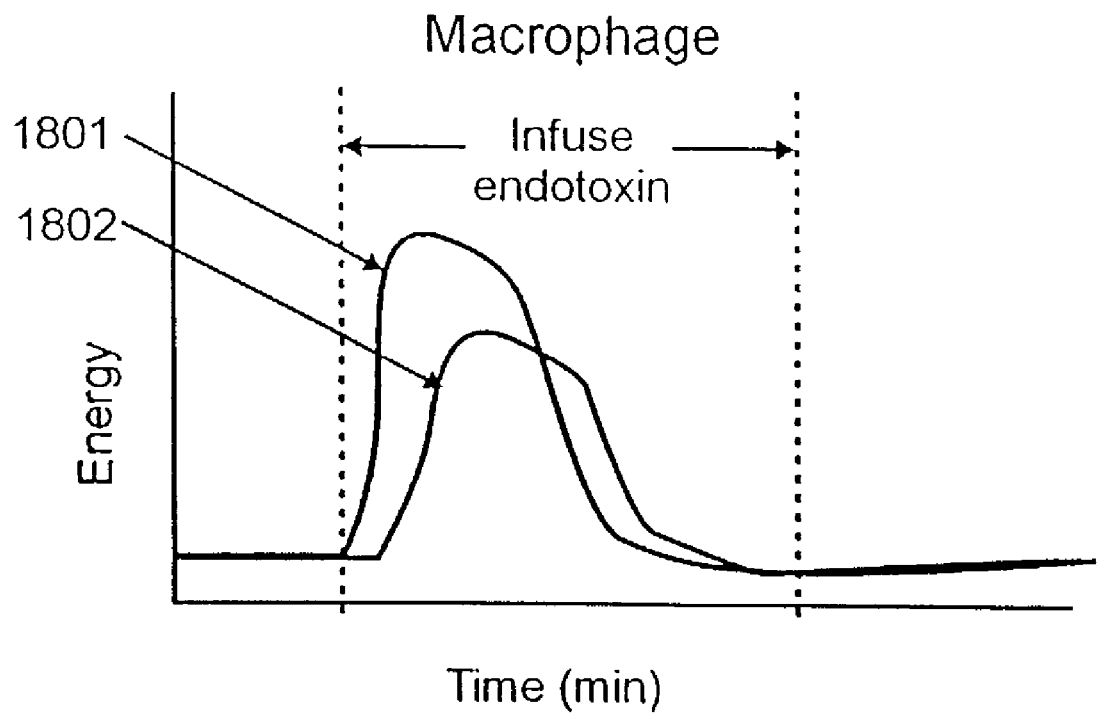
FIG. 18 shows discrimination of toxins/agents by monitoring characteristic temporal response of cellular phenotypes to toxins according to one embodiment of the present invention: A. for Macrophage; and B. for Hepatocyte.
Figure 18B:
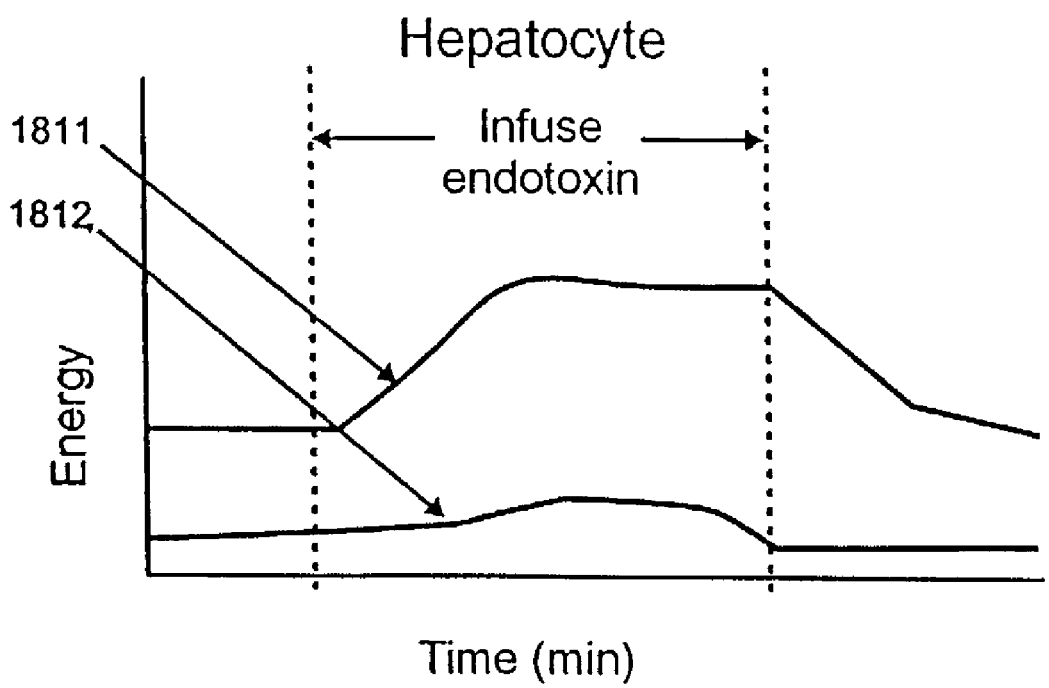

FIGS. 18A and 18B display the discrimination of toxins/agents by monitoring characteristic temporal response of cellular phenotypes to toxins. Since the devices provided by the present invention are small, the temporal response is expected to be measured with millisecond resolution. Different agents such as toxins act on different time scales that will be used for discrimination. As an example shown in FIG. 18A, upon stimulation with endotoxin or phorbol esters, macrophages have an oxidative burst in which oxygen consumption, represented by line 1801, increases rapidly and markedly. Interestingly, this increase is not as dependent upon mitochondrial function as is seen in the liver. In macrophages endotoxin and phorbol esters activate a cytosolic enzyme (NADPH oxidase) that catalyzes the reaction ($NADPH+2O_2 \rightarrow NADP^+ + 2H^+ + 2O_2^-$), Hydrogen peroxide ($H_2O_2$) is produced by dismutation of $O_2$, represented by line 1802. The free radicals generated in turn are cytotoxic due to its rapid conversion to $OH^-$ and other radicals. Thus, the increased consumption of oxygen is less dependent upon a mitochondrial response and is more rapid in onset and greater in magnitude that that of the liver, as shown below, the peak response is within five minutes and is paralleled by a rapid increase in free radical formation. In contrast, energy expenditure in hepatocytes, as shown in FIG. 18B, is increased when challenged by agents, as shown by the increase in $O_2$ consumption 1811. But this is accompanied by only a modest rise in free radical production 1802, primarily mitochondrial in origin. Therefore, the characteristics of the biological signature can vary markedly both in terms time of onset, rate of rise, magnitude, and deactivation rate of the individual metabolic or energy signature.

As displayed in these figures, the energy signature of the activated macrophage and the stimulated hepatocyte can be markedly different. Macrophages have a characteristically rapid increase in oxygen consumption, which wanes despite the presence of the stimulus. In contrast the hepatocyte exhibits a response that is slower in onset and sustained until the removal of the stimulus. The controlled addition of a known amount of endotoxin will result in an increase in hepatic energy consumption to support the very high metabolic activity of the liver. When unknown toxins are administered that uncouple or inhibit this process, for example dinitrophenol or cyanide, the normal energy demanding functions of the liver, such as gluconeognesis, are compromised. The consequent cell specific change in metabolic activity can be monitored and used as a canary to detect toxins.

Figure 19A:
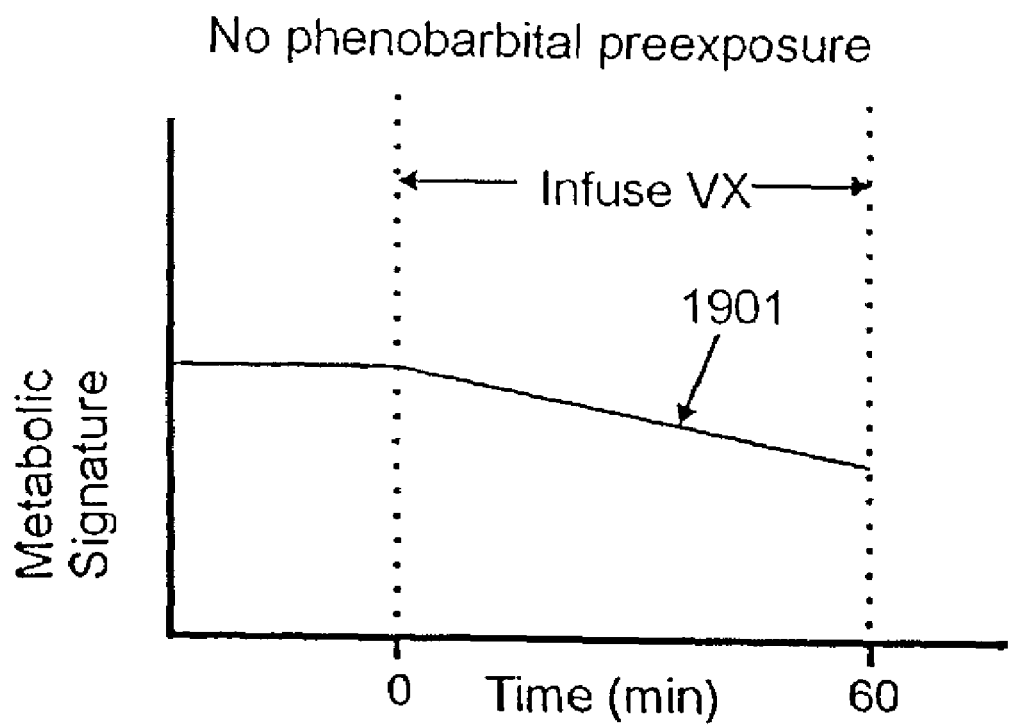
FIG. 19 schematically shows discrimination by characteristic responses in a conditioned environment according to one embodiment of the present invention: A. no phenobarbital preexposure; and B. with phenobarbital preexposure.
Figure 19B:
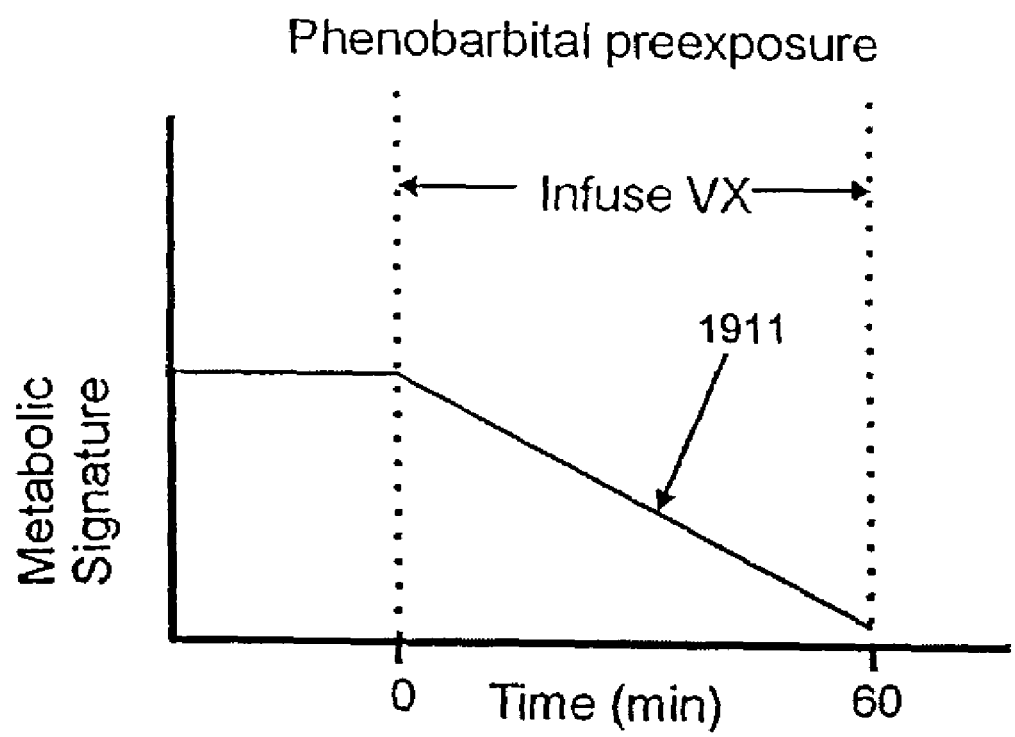
Figure 20:
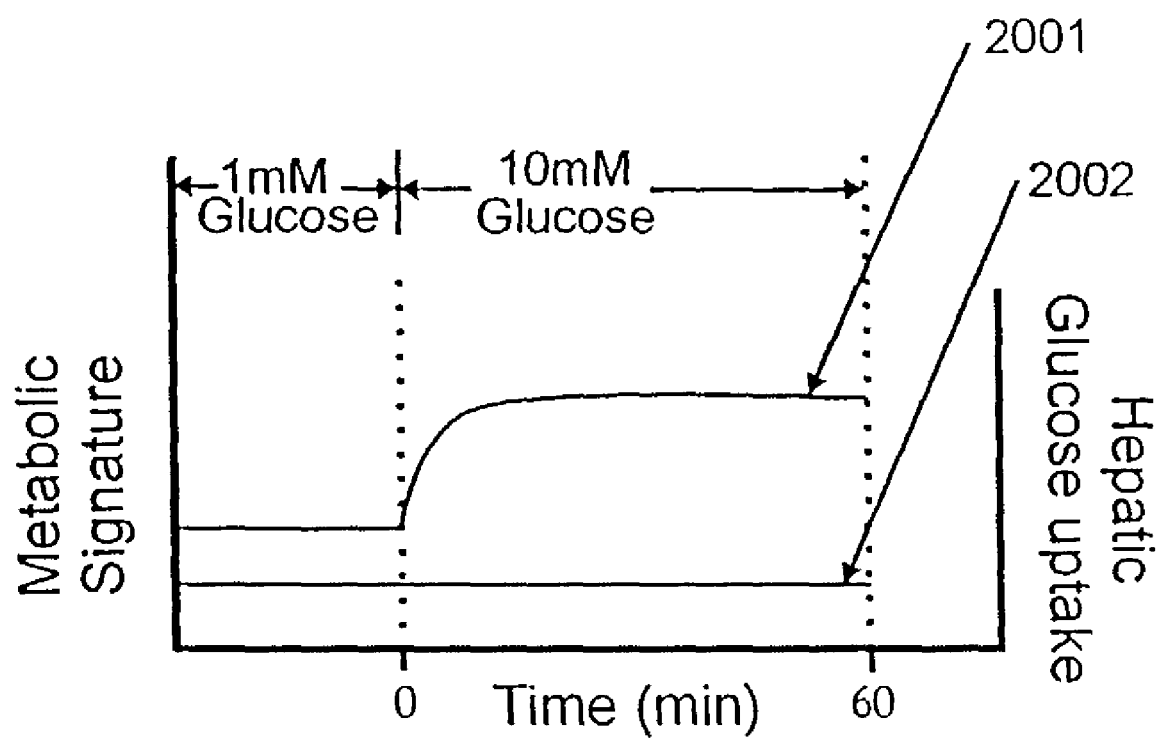
FIG. 20 shows discrimination by characteristic reaction kinetics of metabolic pathways according to one embodiment of the present invention.
Figure 21:
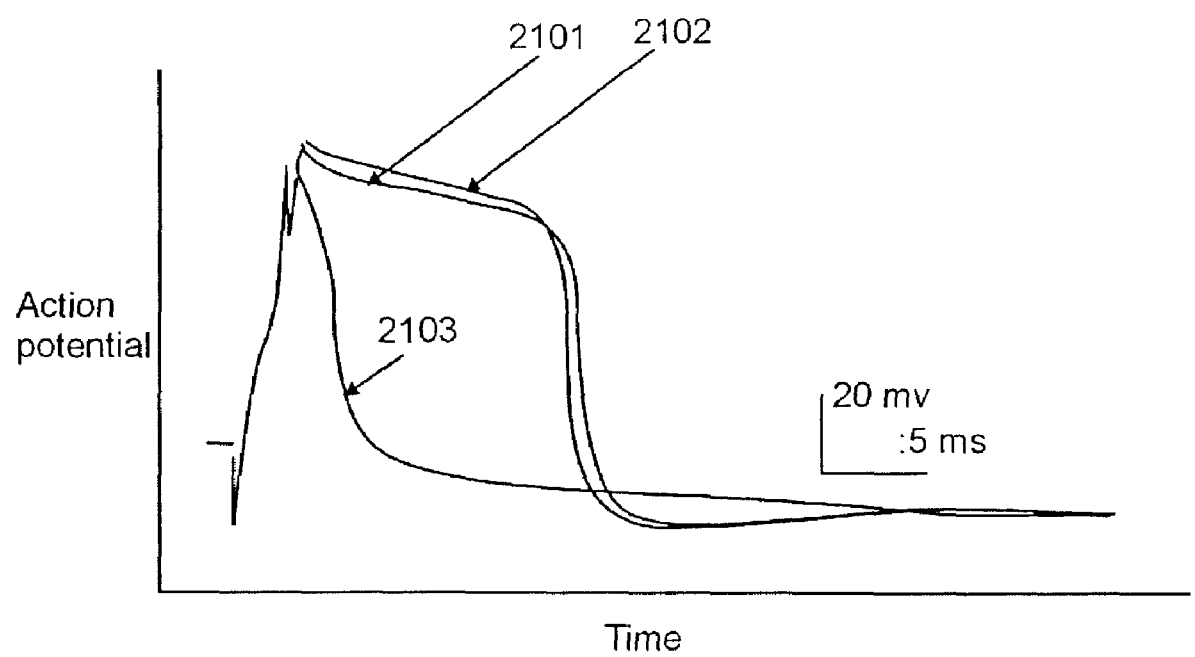
FIG. 21 shows the effect of soman on an action potential of a neuron according to one embodiment of the present invention.

FIGS. 19A and 19B show discrimination by characteristic responses in a conditioned environment. In particular, the difference in lactate release, represented by line 1901, following VX exposure is dependent upon preexposure to phenobarbital, with no preexposure shown in FIG. 19A and preexposure in FIG. 19B, respectively. Preconditioning cells prior to toxin exposure can both serve to amplify a response to a toxin and help in the discrimination between toxins when the cells expose to more than one toxin. Cultured hepatocytes have limited capacity to sustain a gluconeogenic response to regulators of this process. However, prior exposure to dexamethasone markedly improves their response to the normal regulators. By enhancing the baseline gluconeogenic rate, specific inhibitory effects of toxins can readily be detected. Moreover, prior exposure to drugs, which enhance the metabolism of a cell, could be used to discriminate agents. Organophosphates inhibit acetylcholinesterase activity. The data are shown in FIG. 10.

The nerve gas VX and other organophosphates inhibit glycolysis in neuroblastoma cells. However, pre-exposure of neuroblastoma cells to Phenobarbital may enhance the enzyme cytochrome P450, which in turn may result in the cellular conversion of these toxins to a more potent toxin (bioactivation). Thus following bioactivation of hepatocytes with Phenobarbital, the reduction of glycolysis with VX and parathion may be markedly enhanced.

FIG. 20 displays discrimination by characteristic reaction kinetics of metabolic pathways. The metabolic signatures of hepatocytes exposed to a change in glucose concentration in the absence, represented by line 2001, and presence, represented by line 2002, of okadaic acid are shown, respectively.

Additionally, environment may be manipulated to determine where in a given metabolic pathway the toxin is acting. This may be most effective if a toxin takes advantage of a metabolic signaling pathway to exert its action. One important pathway in cell signaling that is affected by a number of toxins is the protein kinase A/cyclic AMP system. This system when activated has profound and well-characterized metabolic responses, which include increases in gluconeogenesis and glycogen breakdown, and inhibition of glycolysis. As one example of pathway modulation, the response of a hepatocyte to an increase in the available glucose will depend upon whether an agent blocks a particular enzyme pathway. Okadaic acid and microcystins inhibit protein phosphatase 1 and 2A activity. Okadaic acid has been shown to regulate cyclic AMP mediated events. Thus in the presence of okadaic acid, an increase in glucose concentration will not increase hepatic glucose uptake.

Other toxins may alter glycogen metabolism as well via their effect on cell signaling pathways. An increase in lactate release that is disproportionate to the increase in glucose uptake, this would suggest an endogenous source of glucose (i.e., glycogen). Increases in lactate release disproportional to the increase in glucose consumption could reflect toxins that either increases cyclic-AMP or intracellular calcium (e.g., organophosphates including the chemical warfare agents Sarin and VX). Increases in cyclic-AMP or calcium will activate hepatic glycogen phosphorylase, which will enhance glycogen breakdown. Since glycogen is a glucose polymer, upon its hydrolysis the cell will release glucose or metabolize the glucose and release it as lactate. By applying specific measurements of intracellular calcium and calcium conductance, for example, one may combine knowledge of metabolic pathways with specific manipulations that allow one to dissect how a specific toxin exerts its action on metabolism.

FIG. 21 shows the shape of the action potential of excitable cells as an integral sensing concept to access the physiological state of the cell. The control action potential of a cardiac cell, represented by line 2101, and the action potential following agent washout, represented by line 2102, are a factor of four longer in duration than the action potential in the presence of Soman, represented by line 2103. Thus, measurement of the shape of the transmembrane action potential can serve as a sensitive but non-specific indicator of the effect of an agent on a cell, and it may even allow discrimination between agents. The action potential can also be used as an initial way to detect the influence of the toxin agent on ion channels and ion pumps.

The effect of Soman on an action potential of a neuron is shown as an example. The course of the action potential depends on the proper function of various ion channels and functionally associated enzymes. Block of individual channels, like sodium channels with TTX, results in an immediate change of the action potential, which is easily detected. Likewise, blocking an associated enzyme, like the Na/K exchanger with Oubain, results in a marked change of the action potential. Blocking the Ca-channel in cardiac tissue with verapamil changes the shape of the action potential dramatically, which could be extracted from the data and being reflected in the action potential duration. For neural cells more so than for cardiac cells, the fitting of a Hodgkin-Huxley-type model to the observed action-potential shape can be used to estimate the conductance variation of key channels.

Thus, among other things, the present invention provides a matrix of biological signatures that can be used to define an orthogonal set of cell lines, assays, and measurements for detecting previously known or unknown toxins, determining mechanisms of toxin activity through real-time biochemistry and autonomous hypothesis generation and testing, and using a bio-silicon circuit to specify and deliver the appropriate antitoxin for cellular-level defense. Additionally, the matrix of biological signatures can be integrated into a field deployable, configurable, and fully automatic device to detect a large number of toxic agents with unsurpassed sensitivity, which does not require the development of specific assays to new toxin threats. Again, this generality arises because the present invention allows measuring the biological impact of toxins rather than the toxins themselves.

Example 2

Nanophyiometer and Bioreactor

In one aspect, the present invention relates to an apparatus for monitoring the status of a cell, more particularly, for screening physiological and biochemical effects of one or more cells on the nanoliter to picoliter scale. Such an apparatus according to the present invention may be termed as a Nanophysiometer, which in no way should limit the scope of the invention.

FIG. 7 schematically shows a first embodiment of a Nanophysiometer according to the present invention. In FIG. 7, device 700 has a sensing volume 704 filled with a solution of media containing a single or multiple cells 701. The solution of media in the volume 704 can be modified or changed using an inflow channel 708 and an outflow channel 707, which are parts of a channel 721 that is in fluid communication with a supply or reservoir of media (not shown). The flow in each of the channels 707, 708 can be controlled by valves 703, individually or in cooperation.

The volume 704 is bounded on one side by a flexible membrane 705 that can be deflected, e.g., by pressurizing a closed volume 715 below the flexible membrane 705 through the channels 710 or 711, which are parts of a channel 723 that is in fluid communication with a supply or reservoir of fluid such as an air pump (not shown). The flow in each of the channels 710, 711 can also be controlled by valves (not shown), individually or in cooperation. Channel 723 is defined by a first substrate 731.

The volume 704 is bounded on the other side by a second substrate 733 having a first surface 735 and a second surface 737. The second surface 737 of the second substrate 733 and the first substrate 731 defines the channel 721. Several sensors 702 are positioned on the second surface 737 of the second substrate 733 to measure the concentration of analytes in the sensing volume 704. The sensors 702 could be thin film electrodes and can be used to measure various analytes in the sensing volume 704 to monitor the status of the cell 701. The sensors 702 are coupled through leads 709 to a sensing unit (not shown), respectively. Note that by deflecting the membrane 705 forces may be applied to the cell 701, in particular when the cell 701 is attached to the membrane 705, so that the response of the cell 701 to the applied force can be detected. Further note that device 700 can be utilized to grow a cell. For instance, a cell can be attached to the membrane 705, and the status of the cell can be monitored by sensors 702.

Figure 12A:
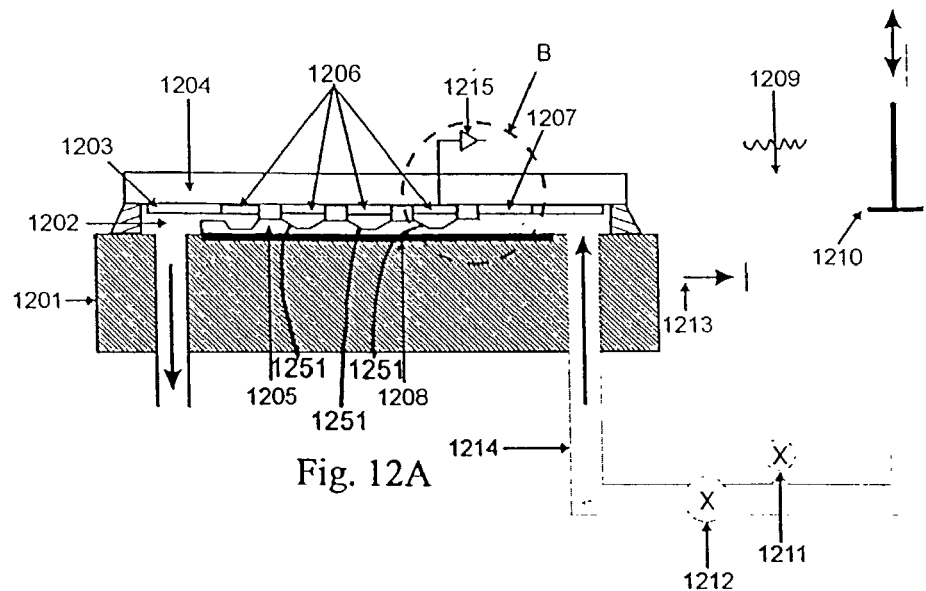
FIG. 12 schematically shows a Nanophysiometer or a device according to one embodiment of the present invention: A. side cross-sectional view along line A-A in FIG. 12B; and B. top view; and C. exploded view of part B in FIG. 12A.
Figure 12B:
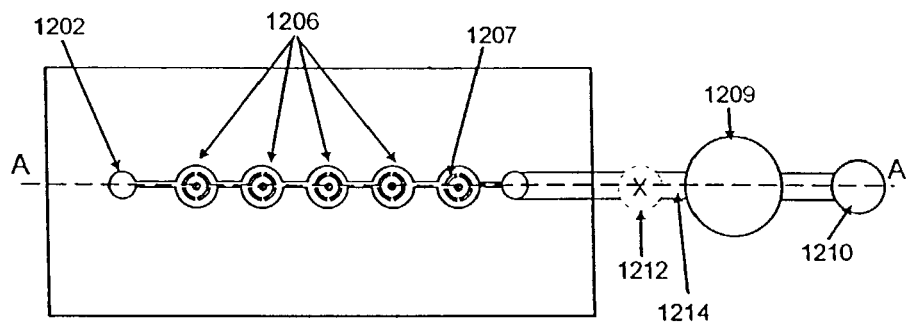
Figure 12C:
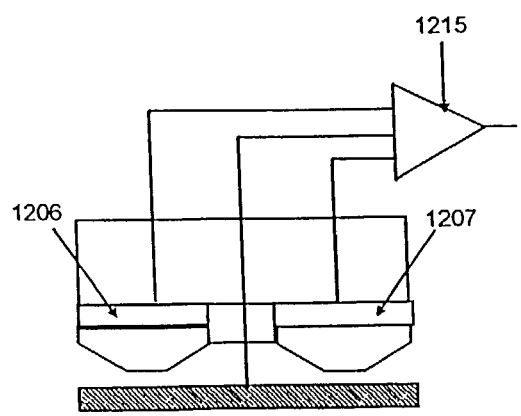

FIG. 12 schematically shows a second embodiment of a Nanophysiometer according to the present invention. In FIG. 12, device 1200 has a system support structure 1201 beneath a microfluidic channel 1202. The microfluidic channel 1202 is formed in a micromachined substrate 1205. A number of wells 1251 are in fluid communication with the microfluidic channel 1202. Epoxy 1203 provides a fluid-tight seal between the support structure 1201, the micromachined substrate 1205, and a cover 1204. Cover 1204 is transparent and supports an array of sensors 1206. Individual electrochemical sensors 1206 include enzyme-activated electrodes, and enzyme electrodes that can determine the extracellular fluidic composition and the consumption and release of metabolic substrate and byproducts when used in combination with silver/silver-chloride reference electrode 1207, gold counter electrode 1208 and an amperometric or potentiometric instrument 1215 that measures and/or applies voltages and/or currents for the combination of electrodes 1206, 1207, 1208. Oxygenated perfusate reservoir 1209, oxygen supply for the perfusate oxygenator, computer-controlled nanoliter syringe pump 1213 and check valves 1211 and 1212 allow the withdrawal by the pump 1210 of oxygenated perfusate 1213, and its subsequent injection through tubing 1214, to the microfluidic channels 1202.

Cells are placed into the wells 1251. Each well has a volume of less than 1 mL and may receive one or more cells to be confined therein. The electrochemical sensors 1206, 1207, 1208 monitor the metabolic state of each cell or cells. The microchannels 1202 with cross-sections on the order of 10 μm×10 μm supply analytes to the cells, remove waste, and allow for the introduction of biological agents into the wells. One to several cells can be placed into each well with a micropipette or through the fluid channels. Among other things, device 1200 has external pumps and valves for automated control of the flow and introduction of the analytes. Moreover, device 1200 has planar electrochemical sensors 1206, and nanoLiter sized volumes 1251 resulting in high sensitivity and fast response times. Additionally, device 1200 has on-chip sealed wells and channels for cell storage, delivery of analytes and biological agents, and removal of waste. Utilization of sensors 1206, 1207, 1208 having different electrochemical characteristics allows for multispectral readout. The transparency of the cover 1204 also makes optical detecting available.

Figure 13A:
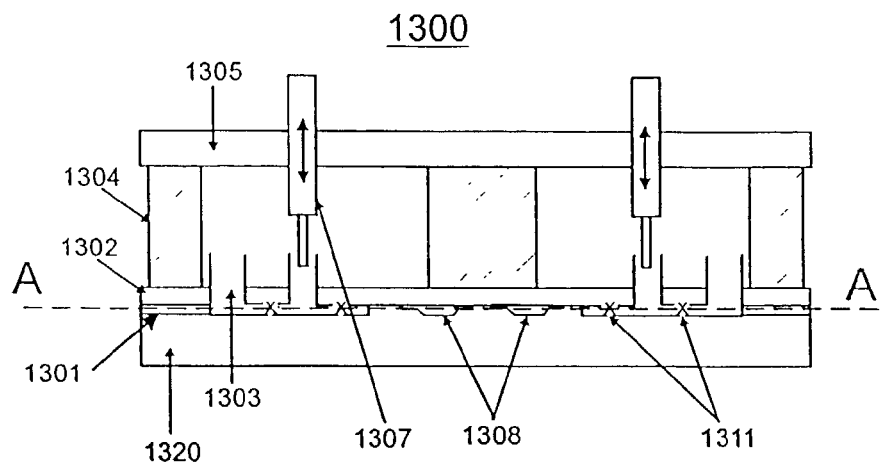
FIG. 13 schematically shows a Nanophysiometer or a device according to another embodiment of the present invention: A. side view; and B. cross-sectional view along line A-A in FIG. 13A; and C. enlargement view of part B in FIG. 13B.
Figure 13B:
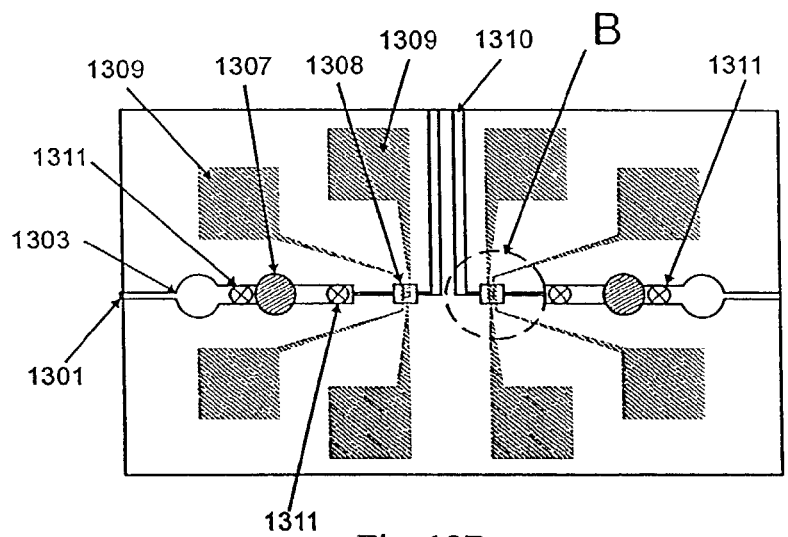
Figure 13C:
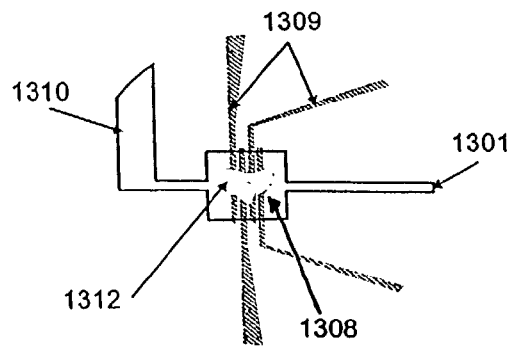

Referring now to FIG. 13, a third embodiment of a Nanophysiometer according to the present invention is shown. In FIG. 13, device 1300 has both external valve actuators and on-chip pumps. Micromachined substrate 1320, which can be formed in silicon, glass, ceramic, plastic, or polymer, defines microfluidic channels 1301, which can be used as oxygen inlet for oxygenating the perfusate interfacing with a cell 1312. An optional cover slip 1302 covers the microfluidic channels 1301. Addressable piezoelectric nanoactuator array 1307 is supported by an actuator platform (or substrate) 1305 and support posts 1304. Check valves 1311 allow the withdrawal of oxygenated perfusate from the reservoir 1303 and its injection into the microfluidic channels 1301 and sample wells 1308 that contain the living cells 1312. The chamber corresponding to each well 1308 is drained by microfluidic line 1310. Sensors in the form of interdigitated microelectrodes 1309 allow the electrochemical determination of analytes in each chamber 1308. Optical detectors (not shown) can also be utilized through the cover 1302, which is at least partially transparent.

Device 1300 shows how external pumps utilized in device 1200 as shown in FIG. 12 can be replaced with on-chip pumps making the device a standalone unit. Device 1300 could be match box sized incorporating, wells, sensors, pumps and actuators to achieve the goal of massively parallel testing. On-chip pumps can be a microscale version of the syringe pumps used in device 1200. Using standard microfluidic technology, each pump will, for example, may have a reservoir covered with a flexible membrane. This membrane will be moved in or out by changing the length of a piezoelectric element. An array of individually addressable piezoelectric filaments can be utilized to provide separate actuation of multiple pumps. This actuator 'bed-of-nails' may also provide valving by pinching closed sections of the channels between the reservoirs.

Figure 26A:
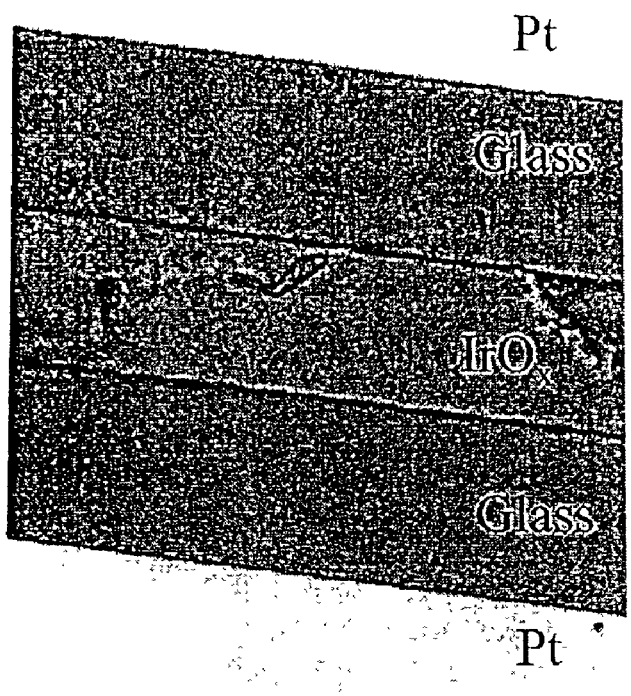
FIG. 26 shows an iridium oxide pH electrode forming on a platinum interdigitated microelectrode array according to one embodiment of the present invention: A. a photomicrograph of the electrode array with platinum, iridium oxide, and platinum microstrips on a glass substrate; B. a pH calibration of the sensor.
Figure 26B:
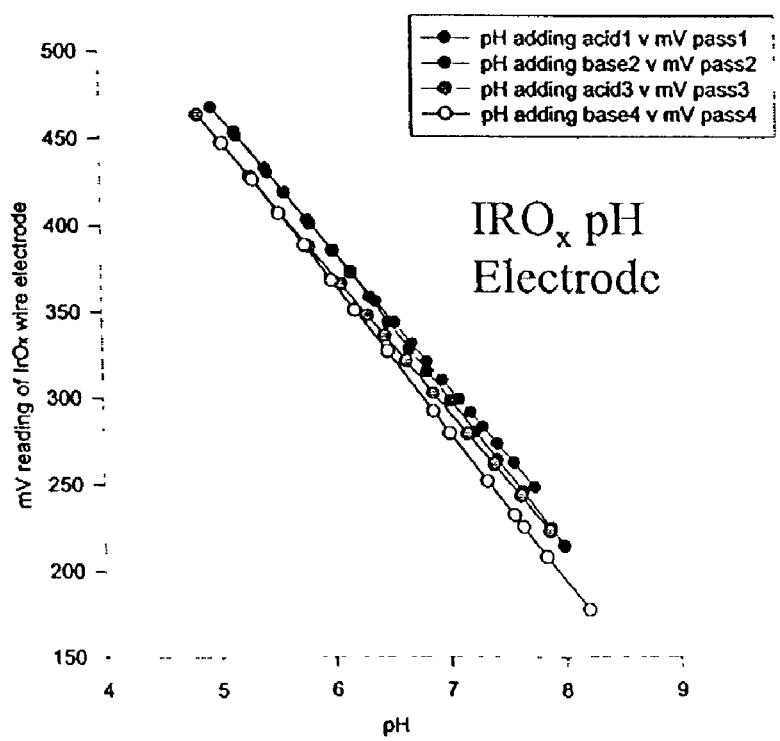

An exemplary electrode can be utilized to practice the present invention including utilization in any embodiment of Nanophysiometer is shown in FIG. 26. FIG. 26A is a photomicrograph of the electrode array with platinum, iridium oxide, and platinum microstrips on a glass substrate. FIG. 26B shows a pH calibration of the sensor. Such an Iridium oxide pH electrode can be used to form on a platinum interdigitated microelectrode array.

Figure 27A:
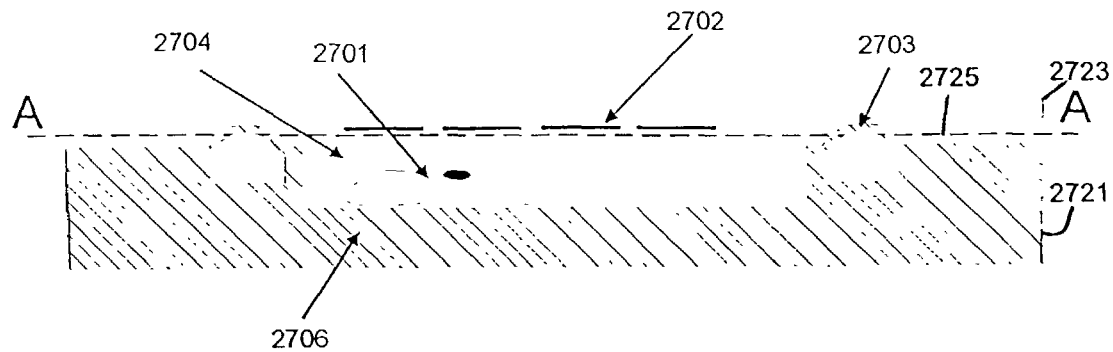
FIG. 27 shows a Nanophysiometer or a device according to one embodiment of the present invention: A. side cross-sectional view; and B. cross-sectional view along line A-A in FIG. 27A.
Figure 27B:
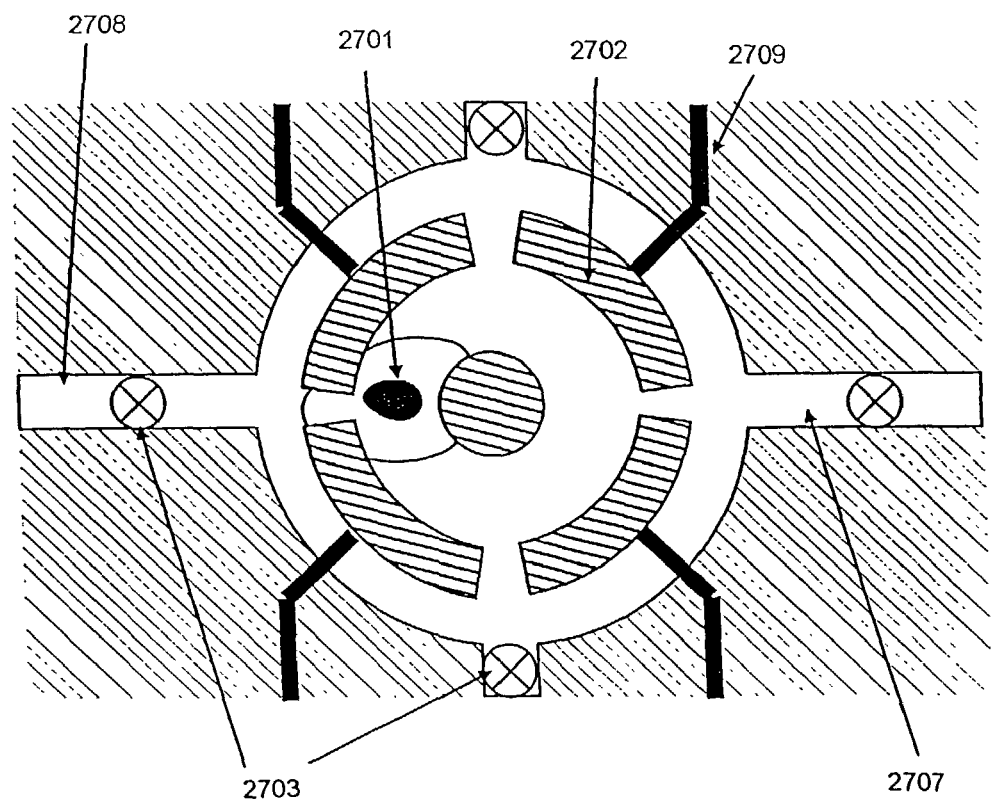

Referring now to FIG. 27, a fourth embodiment of a Nanophysiometer according to the present invention is shown. In FIG. 27, device 2700 has a first substrate 2721 and a second substrate 2723 defining a sensing volume 2704 therebetween. The sensing volume 2704 contains a single or multiple cells 2701 in sufficient close proximity to sensors 2702 designed to monitor the physiological status of the cell or cells 2701 such that any measurement related to the physiological status of the cell or cells 2701 can be made at a time period shorter than a characterization time corresponding to the physiological status of the cell or cells 2701. The sensing volume 2704 is in fluid communication with a channel 2725, which has an inlet portion 2707 and an outlet portion 2708. The liquid media in the sensing volume 2704 can be refreshed or adjusted using the inlet 2707 and outlet 2708, which in turn are controlled by valves 2703, respectively. Measured signals from the sensor(s) 2702 can be read out through a connection 2709 to electronics such as a controller (not shown). Additional channels into the sensing volume 2710 can be used to deliver agents and other analytes to the sensing volume 2704. The second substrate 2723 may be at least partially transparent for optical detecting. The device 2700 can be formed, for example, by fusing a first part containing the sensors and a second part containing the fluidic channel and the valves together.

Figure 28A:
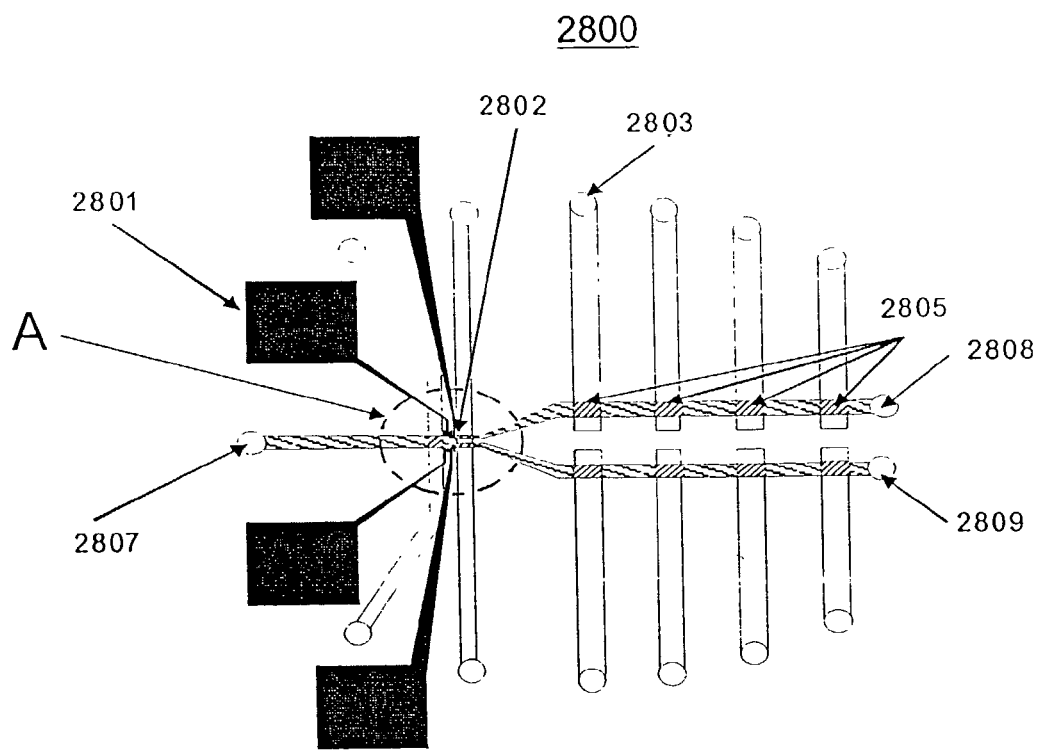
FIG. 28 shows a Nanophysiometer or a device according to another embodiment of the present invention: A. top view; and B. exploded of part A in FIG. 28A; and C. cross-sectional view along line B-B in FIG. 28B.
Figure 28B:
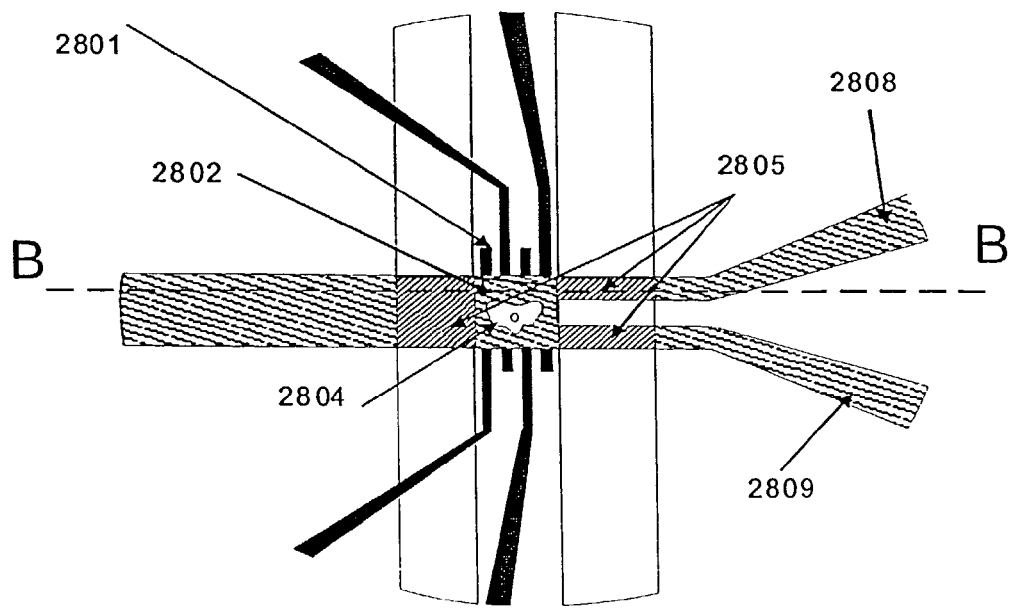
Figure 28C:
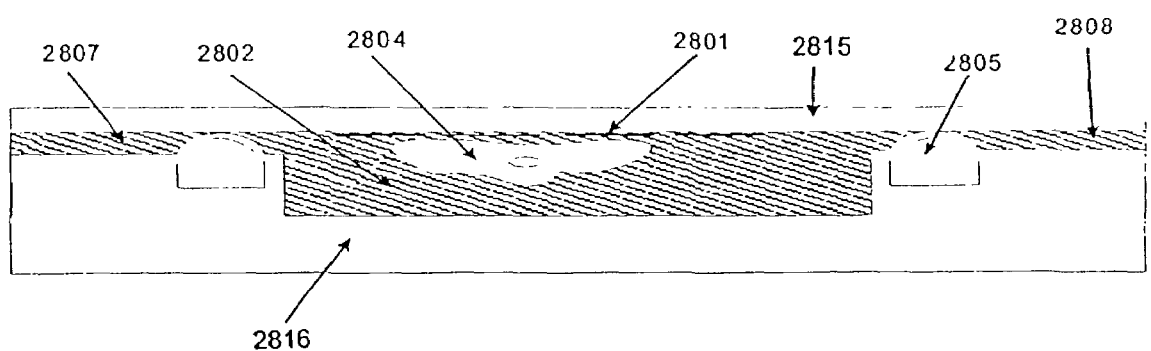

Referring now to FIG. 28, a fifth embodiment of a Nanophysiometer according to the present invention is shown. In FIG. 28, device 2800 has an input channel 2808, an outlet channel 2807 and an additional channel 2809, which may be used as an additional outlet channel or to flush out the contents from a sensing volume 2802 that is in fluid communication with each of channels 2807, 2808, and 2809. The liquid media in the sensing volume 2802 is changed or adjusted either continuously or in a stop flow fashion through actuation of the valves 2805 in the inlet 2808 and outlet channel 2807 by pressurizing the media in the inlet channel 2808, respectively. The valves 2805 are actuated through lines 2803, each being in fluid communication with a supply or reservoir of fluid such as pressured air. The inlet channel 2807 is equipped with a series of valves 2805 which can be actuated to act as a peristaltic pump. The same can be used for the outlet channel 2807. The sensing volume 2802 is equipped with multiple sensors 2801 to monitor the physiological status of a single cell or cells 2804. The sensors 2801 can take various forms. For examples, sensors 2801 can be in the form of functionalized thin film metal electrodes that are positioned in sufficient close proximity to the cell or cells 2804. The surface of each sensor may have a coating that facilitates cell adhesion (not shown). The device 2800 can be formed, for example, by fusing a first part 2815 containing the sensors and a second part 2816 containing the fluidic channel and the valves together.

Figure 29A:
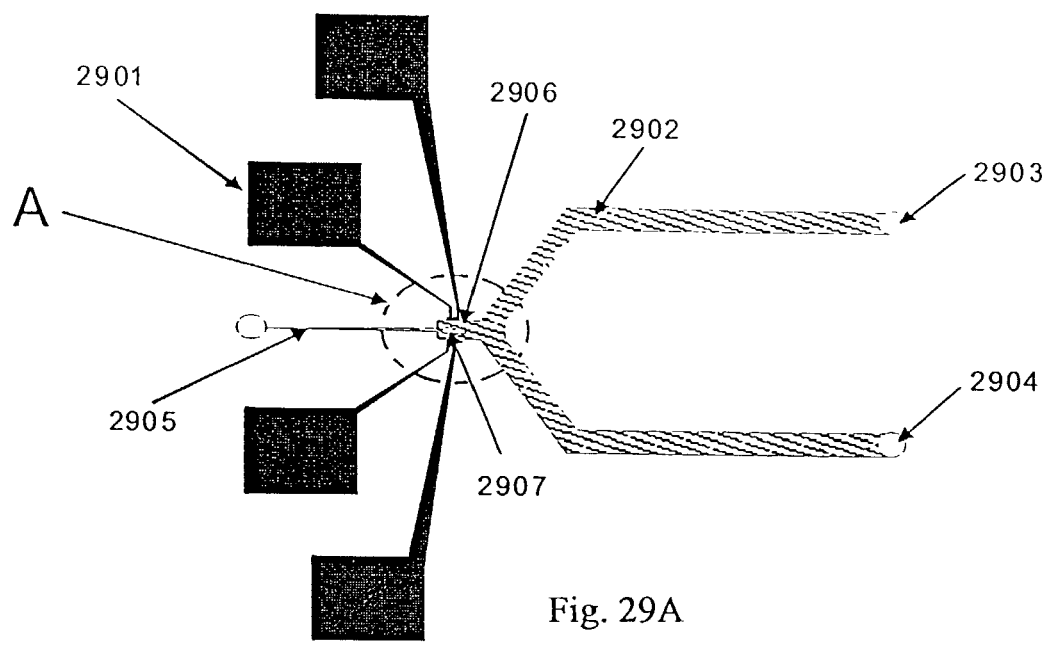
FIG. 29 shows a Nanophysiometer or a device according to yet another embodiment of the present invention: A. top view; and B. exploded of part A in FIG. 29A; and C. cross-sectional view along line B-B in FIG. 29B.
Figure 29B:
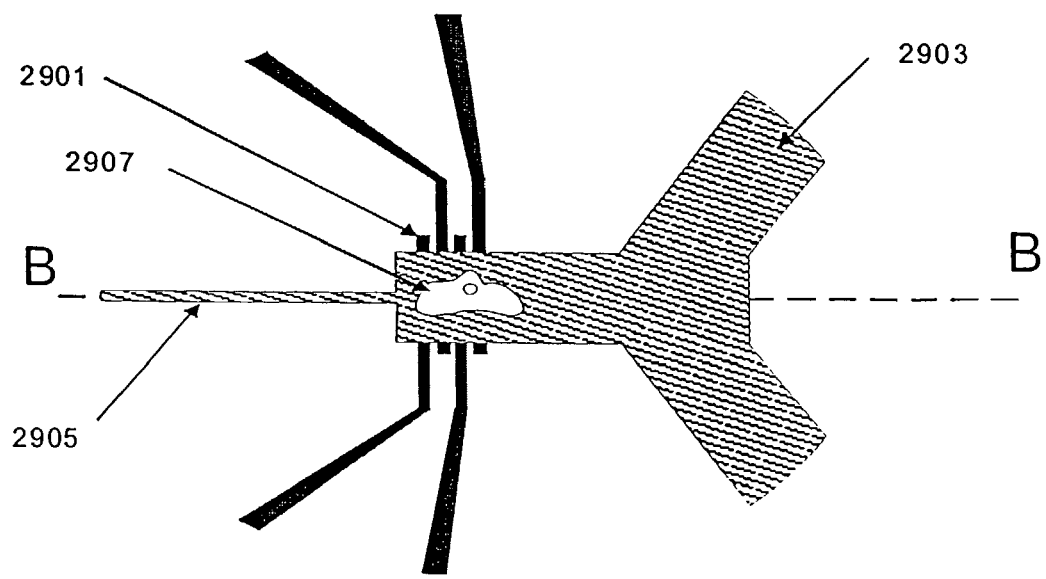
Figure 29C:
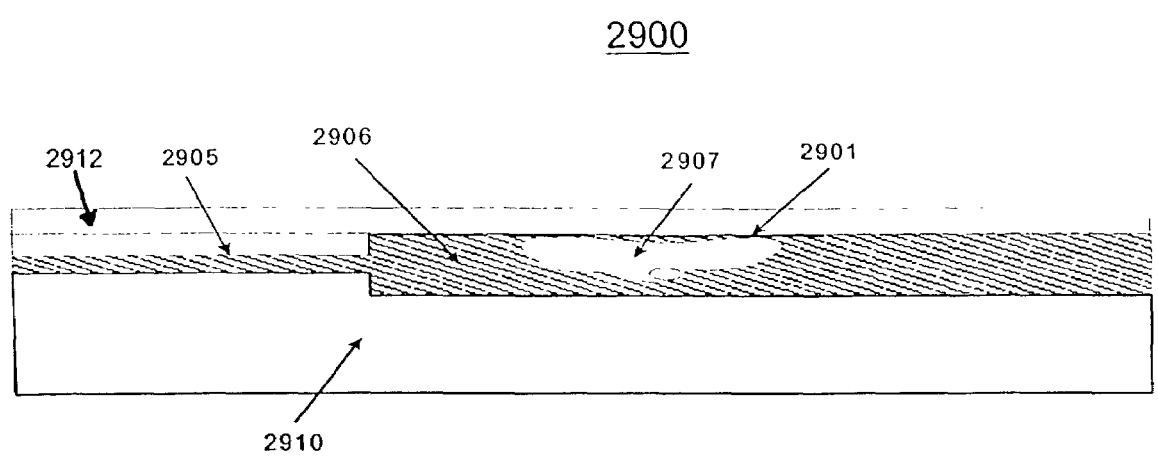

Referring now to FIG. 29, a sixth embodiment of a Nanophysiometer according to the present invention is shown. In FIG. 29, device 2900 has a valveless structure to trap or confine a cell 2907 in the sensing volume 2906 containing liquid media. The cell 2907 is placed in the sensing volume 2906 by flowing the cell 2907 in through an input channel 2903. The sensing volume 2906 is in fluid communication with an output channel 2905, which is optional and has a cross section smaller than that of the input channel 2903. Another channel 2904, which is in fluid communication with the sensing volume 2906, may be used to deliver the cell 2907 to the sensing volume 2904, or to remove the cell 2907 at the end of the measurement. The sensing volume 2906 is adapted such that it is not very much bigger than the size of the cell 2907 so only one or a small number of cells may enter the sensing volume 2906 at one time. In operation, once a cell or cells are placed in the sensing volume 2906 through a loading phase, the media in the channel 2903 is changed to a media corresponding to a measurement phase or maintenance phase. After the measurement phase, the channel 2903 can be pressurized to reverse the flow of the media to eject the cell 2907 from the sensing volume 2906. The media of the sensing volume 2906 can be exchanged or adjusted either by diffusion from the input/output channel where a constant flow is of fresh media for maintenance or by appropriately dimensioning the additional output channel 2905 which leads to a flow away from the sensing volume 2906. Multiple sensors 2901 are positioned in the sensing volume 2906 to monitor the physiological status of a single cell or cells 2907. The sensors 2901 can take various forms. For examples, sensors 2901 can be in the form of functionalized thin film metal electrodes that are positioned in sufficient close proximity to the cell or cells 2907. The surface of each sensor may have a coating that facilitates cell adhesion (not shown). The device 2900 can be formed, for example, by fusing a first part 2912 containing the sensors and a second part 2910 containing the fluidic channel and the valves together.

Figure 30:
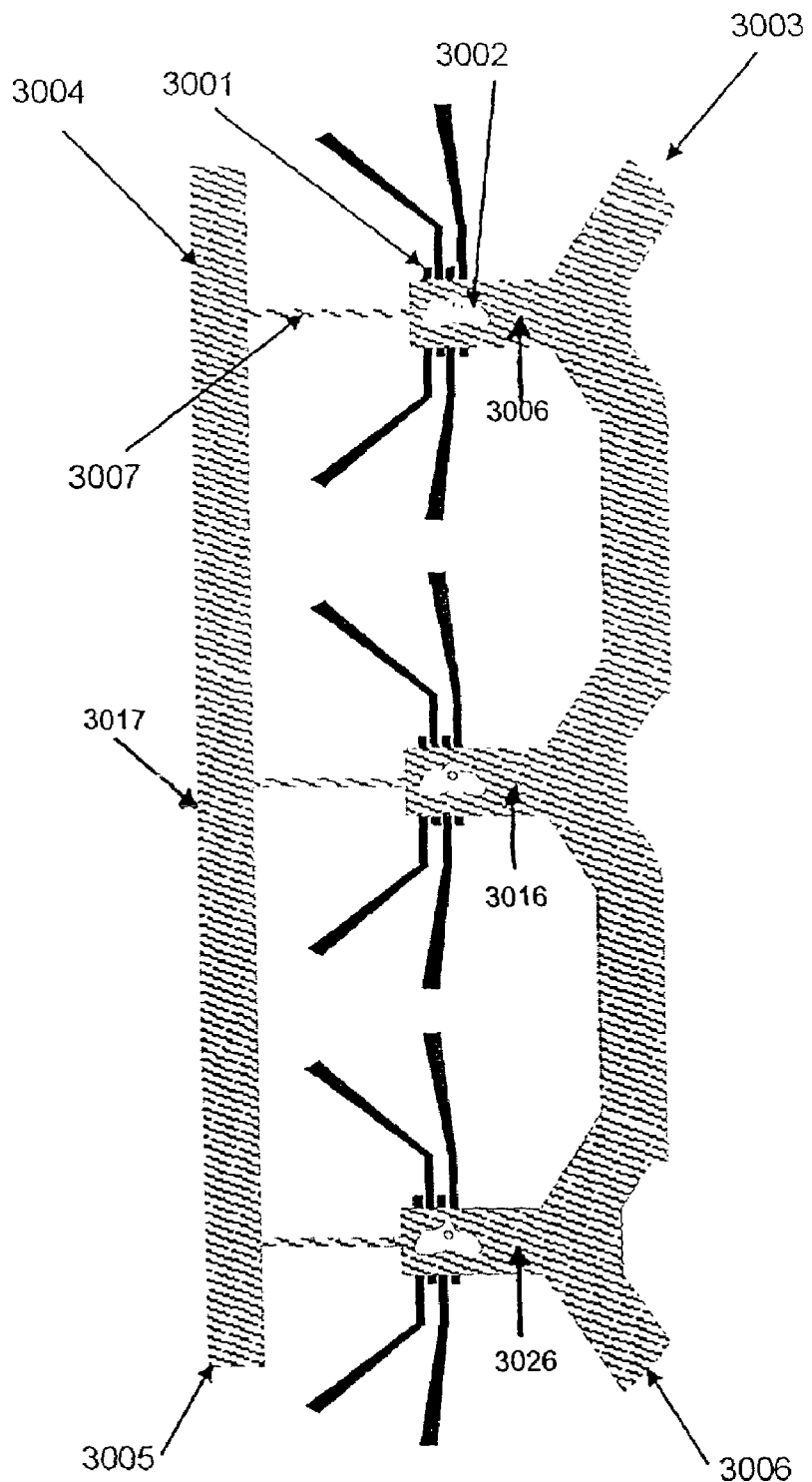
FIG. 30 shows a Nanophysiometer or a device according to a further embodiment of the present invention in a top view.

Referring now to FIG. 30, a seventh embodiment of a Nanophysiometer according to the present invention is shown. In FIG. 30, device 3000 can be considered as a multi-trap version of the valveless nanophysiometer as shown in FIG. 29 and has a plurality of sensing volumes 3006, 3016, 3026 in an array with a common inlet channel 3003 and outlet channel 3006. More sensing volumes can be introduced. The additional channels 3007 lead to a common channel 3017, which also has an inlet channel 3004 and an outlet channel 3005. The sensors 3001 can be read out individually, or in cooperation, from each sensing volume containing one or more cells 3002, respectively.

All the embodiments of a Nanophysiometer according to the present invention shown above can be utilized, among other things, to monitor the status of a cell that consumes or produces energy. The energy consumption or production of the cell includes consumption or secretion of a chemical component by the cell that relates to the metabolic status of the cell, where the chemical component can be any of pH, K, oxygen, lactate, glucose, ascorbate, serotonin, dopamine, ammonia, glutamate, purine, calcium, and sodium. As an example, FIG. 31 shows the utilization of a Nanophysiometer according to the present invention, in particular, according to the embodiment shown in FIG. 28, to measure temporal response of cell or cells to changes in pH and oxygen.

Figure 31A:
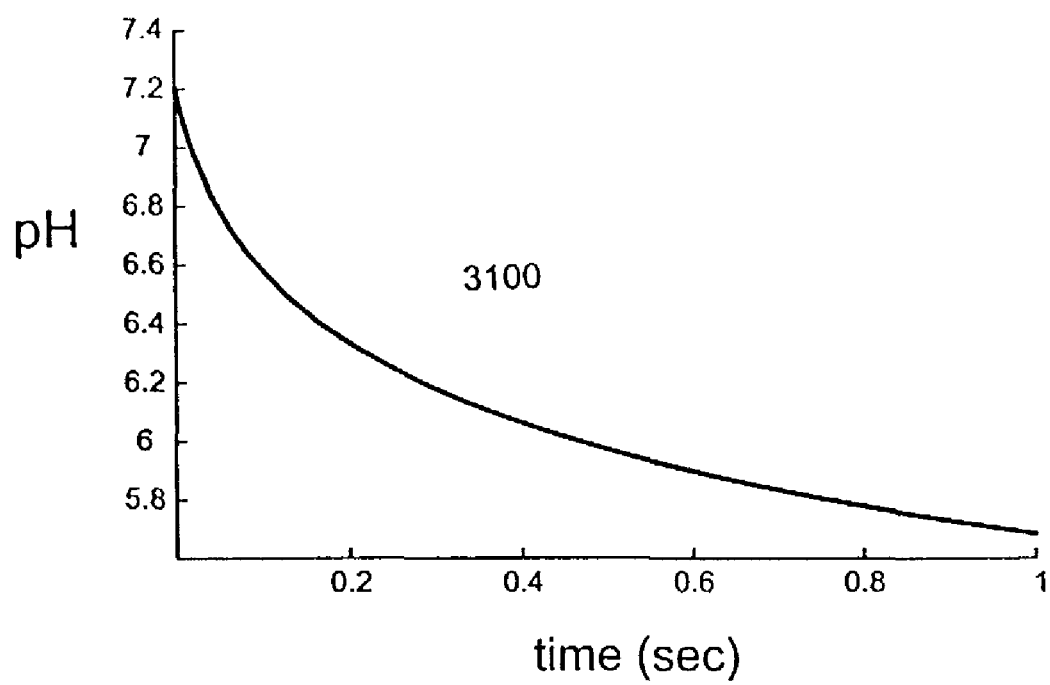
FIG. 31 illustrates the utilization of NanoPhysiometer electrochemical sensors and their temporal response to changes in pH and oxygen according to one embodiment of the present invention: A. the average pH as a function of time in a 100 pL well containing a single cell with no flow; B. same as FIG. 31A, except plotted as a function of logarithmic time to show that the response is constant until the protons have time to diffuse from the cell to the electrode; C. the time taking for the pH to drop by a certain amount; D. the results of the test of the Nanophysiometer with a platinum interdigitated array that senses oxygen; and E. an individually addressable interdigitated microelectrode array.

More specifically, in FIG. 31A, without bounding to any theory, curve 3100 represents average pH as a function of time in a 100 pL well containing a single cell with no flow, based upon the assumptions that the well solution is initially at a pH of 7.2, and at time t=0, the cell begins producing lactate at a constant rate of approximately $6 \times 10^{-10}$ mmol/cell/hr. Thus, for a single cell in the well, there are approximately $2 \times 10^{-13}$ mmol of lactate produced per second. Finally, it is assumed that there is one proton produced for every lactate molecule produced. For a pH close to neutral this is a reasonable estimate, but in reality the ratio of protons to lactate molecules goes down as pH departs from neutral, so this model may overestimate the pH change, which, however, would limit the scope or validity of the present invention.

Figure 31B:
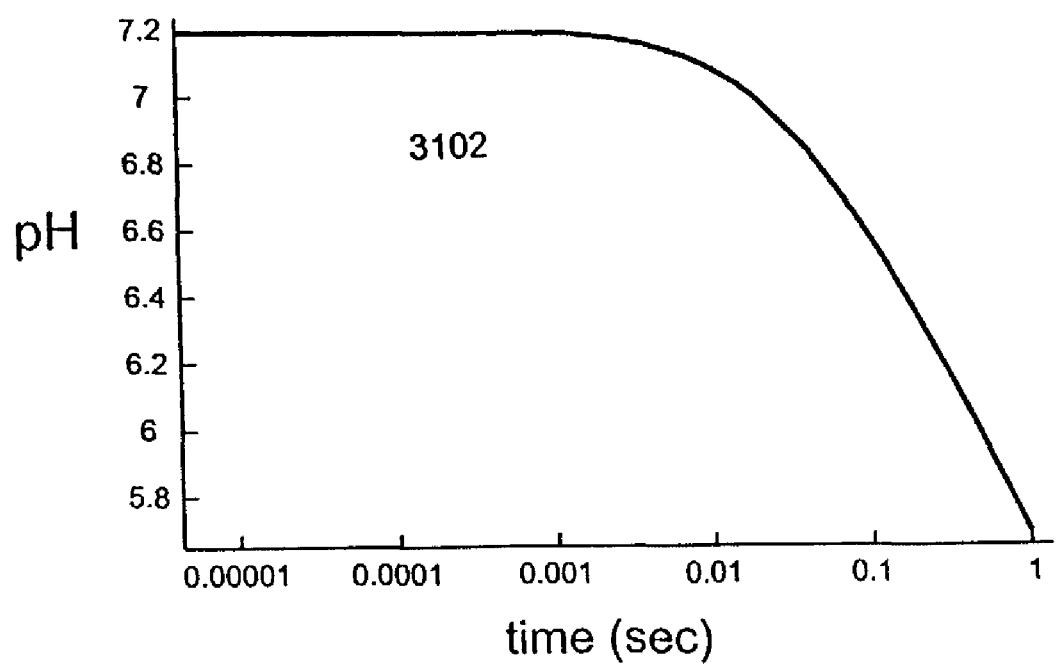

In FIG. 31B, curve 3102 represents the same data as shown in FIG. 31A, except it is plotted as a function of logarithmic time to show that the response is constant until the protons have time to diffuse from the cell to the electrode, which can be characterized by a diffusion time or diffusion constant. A good measurement should be done within a time period that is shorter than the diffusion time.

Figure 31C:
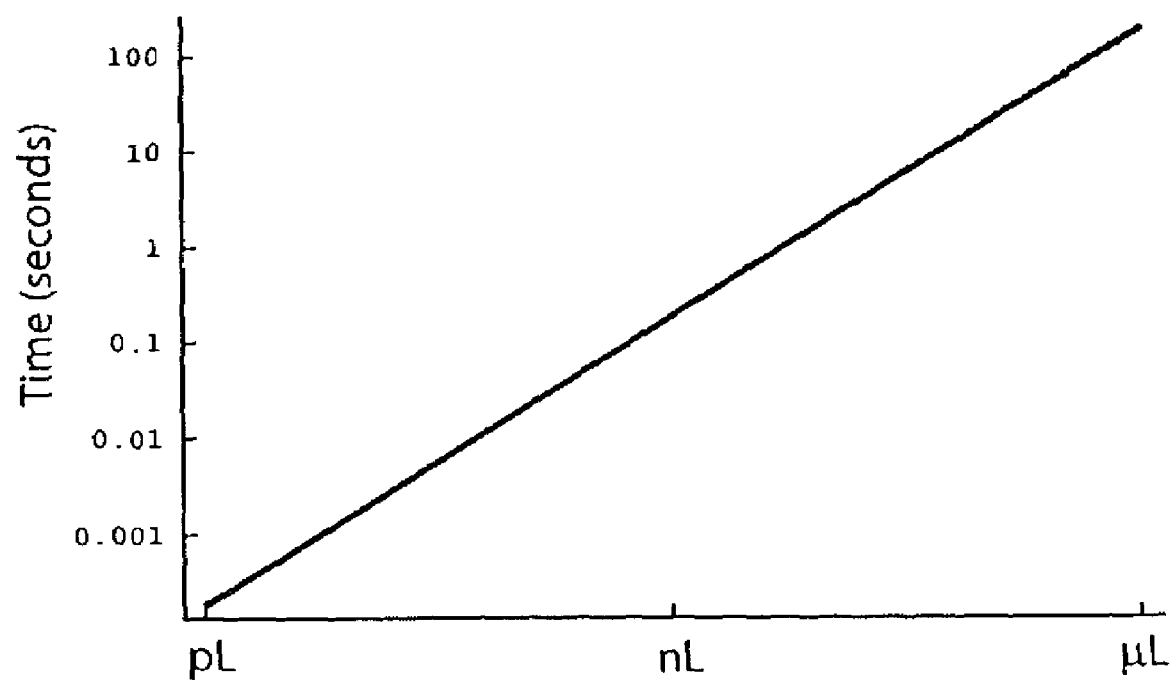

Note that the pH response of a system can be characterized by the time it takes for the pH to drop by a certain amount. For FIG. 31C, the initial pH is 7.2 and the "target" pH is 7.0. Using the model presented in FIGS. 31A and 31B, the time it takes for the pH to drop by 0.2 is a linear function of the system volume, as illustrated in the plot—a pL volume requires about 0.2 msec, whereas a microliter volume takes about 3 minutes.

Table 2.1 gives a list of events and corresponding characterization times for the events to take place. As one can see, some events related to changes in the metabolism of cells happen in a few milliseconds.

TABLE 2.1

| Events | Characterization Time (Seconds) |
| --- | --- |
| 1. Mixing time to homogenize liquid in a large-scale bioreactor (10-100 m$^3$) | $10^4$-$10^8$ |
| 2. 90% liquid volume exchange in a continuous reactor | $10^5$-$10^6$ |
| 3. Oxygen transfer (forced not free diffusion) | $10^2$-$10^3$ |
| 4. Heat transfer (forced convection) | $10^3$-$10^4$ |
| 5. Cell Proliferation, DNA replication | $10^2$-$10^4$ |
| 6. Response to environmental changes (temperature, oxygen) | $10^3$-$10^4$ |
| 7. Messenger RNA synthesis | $10^3$-$10^4$ |
| 8. Translocation of substances into cells (active transport) | $10^1$-$10^3$ |
| 9. Protein synthesis | $10^1$-$10^2$ |
| 10. Allosteric control of enzyme action | $10^0$ |
| 11. Glycolysis | $10^{-1}$-$10^{-2}$ |
| 12. Oxidative phosphorylation in mitochondria | $10^{-2}$ |
| 13. Intracellular quiescent mass & heat transfer (dimension 10-5 μm) | $10^{-5}$-$10^{-3}$ |
| 14. Enzymatic reaction and turnover | $10^{-6}$-$10^{-3}$ |
| 15. Bonding between enzyme & substrate, inhibitor | $10^{-6}$ |
| 16. Receptor-ligand interaction | $10^{-6}$ |

For further comparison, Dn=Diffusion time calculated for Oxygen, where n=25, and lactate n=5, for spherical geometry (indexed as "s") and cubic geometry (indexed as "c"), respectively, is given below:

$$D5 := 5 \cdot 10^{-10} \cdot m^2 \cdot s^{-1}, D25 := 25 \cdot 10^{-10} m^2 \cdot s^{-1}$$

$$1 := 0 \ldots 10, x_l := 10^{-l} \cdot m$$

$$t5_l := \frac{(x_l)^2}{2 \cdot D5} \quad t25_l := \frac{(x_l)^2}{2 \cdot D25}$$

$$Vs_l := \frac{4 \cdot \left(\frac{x_l}{2}\right)^3}{3}; \quad Vc_l := (x_l)^3$$

$$x = \begin{bmatrix} 1 \\ 0.1 \\ 0.01 \\ 1 \cdot 10^{-3} \\ 1 \cdot 10^{-4} \\ 1 \cdot 10^{-5} \\ 1 \cdot 10^{-6} \\ 1 \cdot 10^{-7} \\ 1 \cdot 10^{-8} \\ 1 \cdot 10^{-9} \\ 1 \cdot 10^{-10} \end{bmatrix} m \quad t5 = \begin{bmatrix} 1.10^9 \\ 1.10^7 \\ 1.10^5 \\ 1.10^3 \\ 10 \\ 0.1 \\ 1 \cdot 10^{-3} \\ 1 \cdot 10^{-5} \\ 1 \cdot 10^{-7} \\ 1 \cdot 10^{-9} \\ 1 \cdot 10^{-11} \end{bmatrix} s \quad t25 = \begin{bmatrix} 2 \cdot 10^8 \\ 2 \cdot 10^6 \\ 2 \cdot 10^4 \\ 200 \\ 2 \\ 0.02 \\ 2 \cdot 10^{-4} \\ 2 \cdot 10^{-6} \\ 2 \cdot 10^{-8} \\ 2 \cdot 10^{-10} \\ 2 \cdot 10^{-12} \end{bmatrix} s$$

-continued $$Vs = \begin{bmatrix} 166.667 \\ 0.167 \\ 1.667 \cdot 10^{-4} \\ 1.667 \cdot 10^{-7} \\ 1.667 \cdot 10^{-10} \\ 1.667 \cdot 10^{-13} \\ 0 \\ 0 \\ 0 \\ 0 \\ 0 \end{bmatrix} \text{liter} \quad Vc = \begin{bmatrix} 1 \cdot 10^3 \\ 1 \\ 1 \cdot 10^{-3} \\ 1 \cdot 10^{-6} \\ 1 \cdot 10^{-9} \\ 1 \cdot 10^{-12} \\ 1 \cdot 10^{-15} \\ 0 \\ 0 \\ 0 \\ 0 \end{bmatrix} \text{liter}$$

Oxygen noise 10 micromolar; sensitivity scales with area

Glucose noise 100 micromolar $$tr := \frac{((6.5 \cdot mm))^2}{2D25}$$

Flux at surface; signal-to-noise scales with area:

$$tr = 140.833 \text{ mm}$$

$$F := \frac{I}{n \cdot e \cdot F \cdot A}$$

$(.000100 \text{ m})^3 = 1 \times 10^{-9}$ liter

Oxygen in water at 40° C.

$$D := 0.0000324 \text{ cm}^2 \cdot s^{-1}$$

$$D = 3.24 \times 10^{-9} \frac{m^2}{s}$$

Figure 31D:
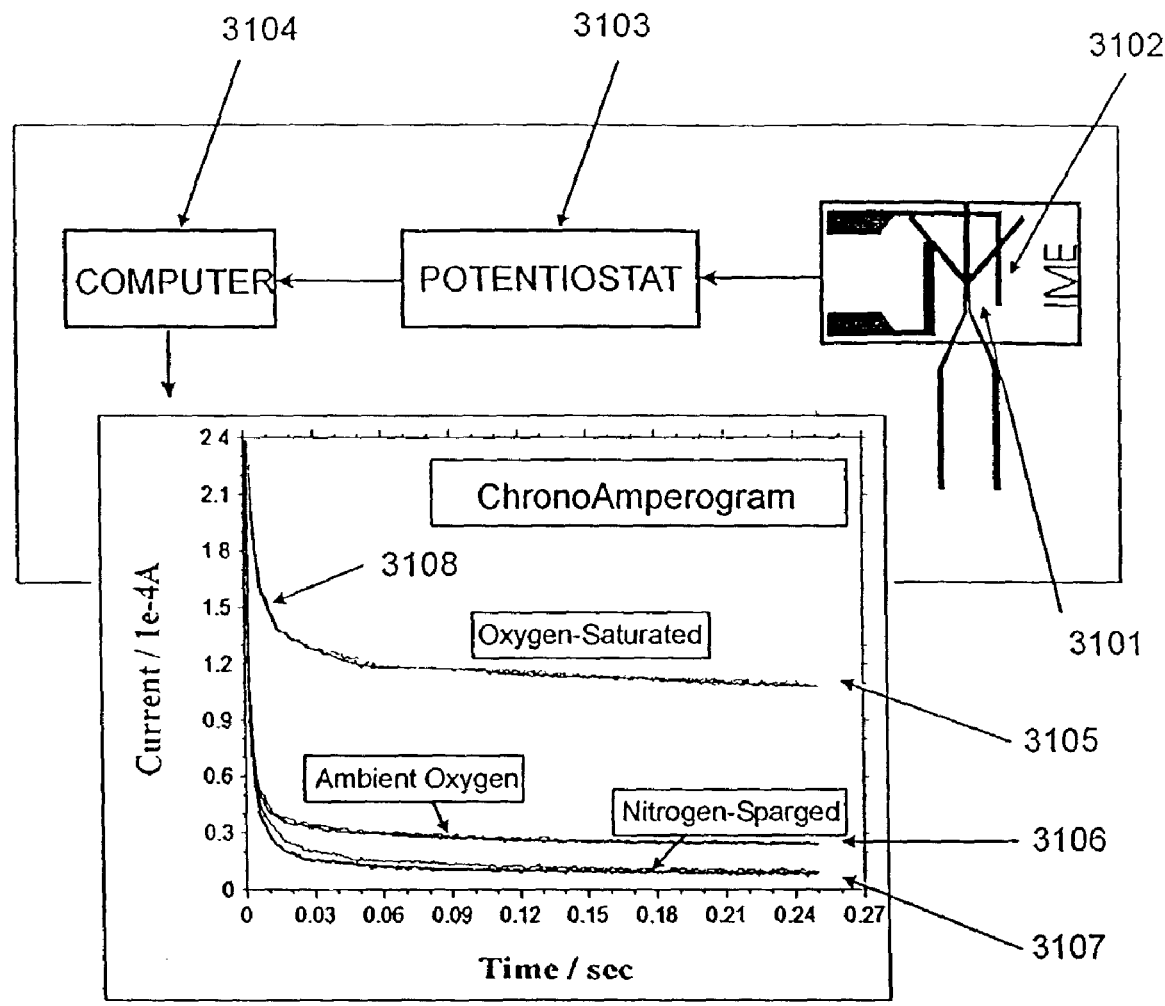
Figure 31:
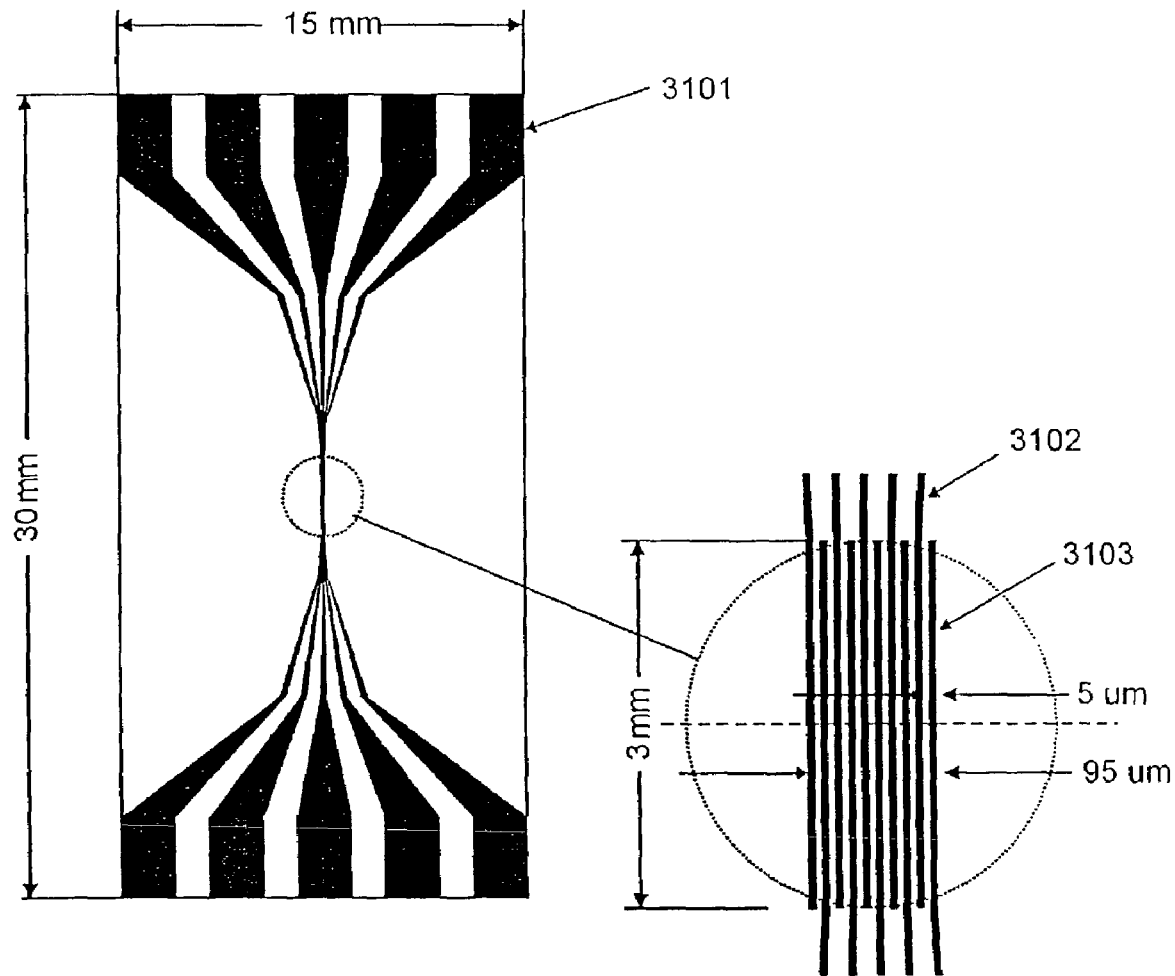

FIG. 31D displays the results of the test of the Nanophysiometer with a platinum interdigitated array that senses oxygen. The microfluidic nanophysiometer 3101 is similar to the one as shown in FIG. 28. The oxygen sensing electrodes 3102 are coupled to a potentiostat 3103 and the computer 3104 that generates plots of the oxygen concentration as a function of time for fluid that is oxygen saturated 3105, perfused with ambient-oxygen 3106, or nitrogen sparged 3107. The rapid response 3108 shows that these electrodes can track oxygen changes that occur in tens of milliseconds, which is possible because, among other advantages, the device(s) of the present invention has sensor(s) positioned sufficiently close to the cell, i.e., at nano-scale dimension. In other words, the small (in term of dimension) is fast (in term of response), and the fast is better (in term of quality of signals, and thus applications).

FIG. 31E displays as an example an individually addressable interdigitated microelectrode array that can be used to practice the present invention. A 2 mm wide pad 3101 of platinum on the glass substrate is coupled to interdigitated microstrip electrodes 3102 and 3103 that are five microns wide and separated by five microns aid thus forming a plurality of fingers. Each of the individual fingers can be coated with silver/silver chloride, gold, iridium oxide, or enzymes to determine what each microstrip may detect.

Example 3

Improved Sensor Head

Figure 11A:
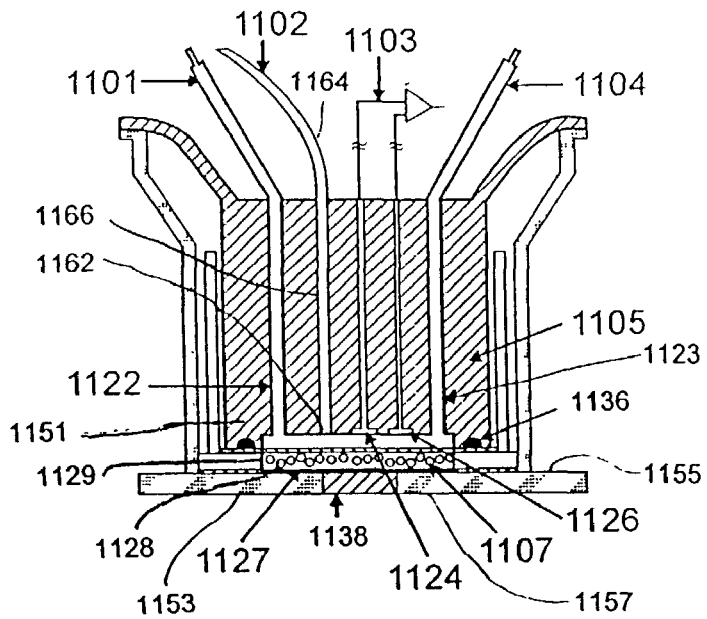
FIG. 11 schematically shows a sensor head for multispectral readout according to one embodiment of the present invention: A. side sectional view; B. bottom view; and C. perspective view.
Figure 11B:
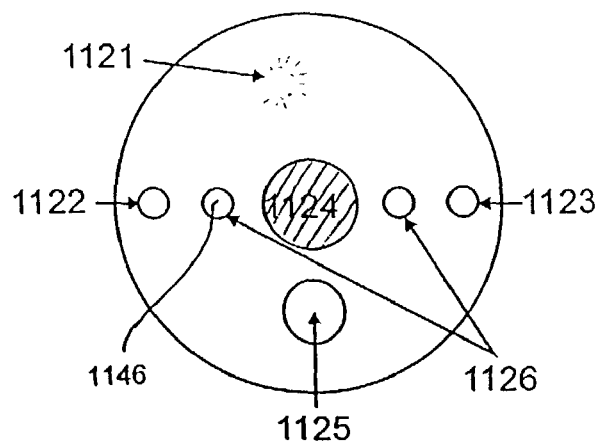
Figure 11C:
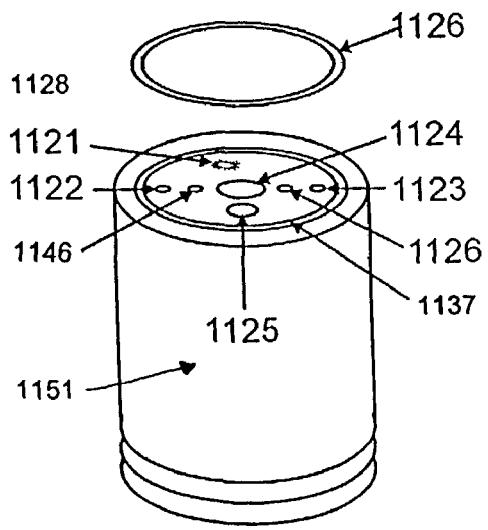

In one aspect, the present invention relates to a device as shown in FIGS. 11(A)-(C) for detecting at least one analyte of interest either produced or consumed by at least one cell or cells 1107, wherein the at least one cell or cells 1107 is placed in a chamber 1128. In one embodiment of the present invention as shown in FIGS. 11(A)-(C), a device or a sensor head 1100 includes a body portion 1151 and a substrate 1153 defining a chamber 1128. The body portion 1151 can be circular, oval, square, or any other geometric shape cross-sectionally. In the embodiment shown, the body portion 1151 has a circular cross section. The substrate 1153 has a first surface 1155 and an opposite, second surface 1157. A membrane 1127 is positioned on the first surface 1155 of the substrate 1153. The membrane 1127 is partially transparent to allow optical signals passing through. For instance, in one embodiment as shown in FIGS. 11(A)-(C), the membrane 1127 comprises a Si/SiN membrane. An insert 1129 that contains the living cells 1107 is placed into the chamber 1128 and is sealed to the body portion 1151 by an O-ring 1136 that fits into a corresponding O-ring groove 1137 formed on the body portion 1151.

An inlet 1101 is in fluid communication with the chamber 1128 through an end portion 1122. Inlet 1101 may also be in fluid communication with one or more reservoirs of mediums (not shown), where each medium may contain a different analyte of interest. The device 1100 also has a first electrode 1124 having a first electrochemical characteristic, and a second electrode 1126 positioned away from the first electrode 1124 and having a second electrochemical characteristic. The device 1100 may further have a reference electrode 1125. In cooperation with the reference electrode 1125, the first electrode 1124 can detect a first analyte of interest either produced or consumed by at least one cell or cells 1107, and the second electrode 1126 can detects second analyte of interest by at least one cell or cells 1107, respectively and simultaneously. Alternatively, in cooperation with the reference electrode 1125, the first electrode 1124 and the second electrode 1126 can detect one analyte of interest either produced or consumed by at least one cell or cells 1107 in the chamber 1128. Analytes of interest can be introduced to the chamber 1128 through the inlet 1101, 1122. An outlet 1104 is in fluid communication with the chamber 1128 through an end portion 1123 for introducing medium away from the chamber 1128.

The device 1100 may utilize an amperemeter electrically coupled to the first electrode 1124 and the second electrode 1126 for detecting a current as a function of the two analytes of interest either produced or consumed by at least one cell or cells 1107 in the chamber 1128. Alternatively, the device 1100 has a potentiostat 1103 electrically coupled to the first electrode 1124 and the second electrode 1126 for detecting a voltage as a function of the two analytes of interest either produced or consumed by at least one cell or cells 1107 in the chamber 1128. Meters such as potentiostat 1103 can be further interfaced to a data acquisition computer so as to save, process and analyze detected signals.

Moreover, the device 1100 may further have additional electrodes, each having a different electrochemical characteristic to one of the first electrode 1124 and the second electrode 1126 and being positioned away from the first and second electrode 1126s. For examples, the device 1100 may have a third electrode 1146 positioned away from the first electrode 1124 and the second electrode 1126. In the embodiment as shown in FIGS. 11(A)-(C), the first electrode 1124 is a gold electrode and the second electrode 1126 and the third electrode 1146 both are a platinum electrode. Moreover, Additionally, the first electrode 1124 has a cross section larger than that of both the second electrode 1126 and the third electrode 1146, which are substantially similar to each other for the embodiment as shown (they are indeed platinum wires). Using the platinum electrodes 1126 and 1146 as a counter electrode, the device 1100 adds the ability to perform electrochemical and spectrochemical analysis within the sensor head 1100. Of course, the first electrode 1124, the second electrode 1126 and the third electrode 1146 each can have different surface film, coating, shape, material modifications to accommodate the needs for detecting one or more desired analytes of interest.

Furthermore, the device 1100 has a fiber-coupled optical system 1102 that has a first end 1162, a second end 1164 and an optical fiber body portion 1166 defined therebetween. The first end 1162 of the optical fiber body portion 1166 reaches in the chamber 1128 capable of detecting an optical signal related to the analytes of interest either produced or consumed by cell or cells 1107. Thus, the fiber-coupled optical system 1102 can monitor fluorescence of the cells by light 1121 emitted into the chamber 1128.

Thus, the device 1100 with the electrodes embedded in a chemically stable epoxy, can measure oxygen, glucose, lactate and oxidation-reduction potential in addition to the pH measurement that is currently available from the membrane 1127 in the bottom of the chamber 1128 and illuminated from below through an optical window 1138, to form a light-addressable potentiometric sensor. The fiber-coupled optical system 1102 can use autofluoresence to measure intracellular NADH/NAD ratios and voltage and calcium-sensitive dyes to determine transmembrane potential and intracellular calcium. The ability of all sensors to function simultaneously allows the specification of a self-consistent set of metabolic fluxes.

Figure 14:
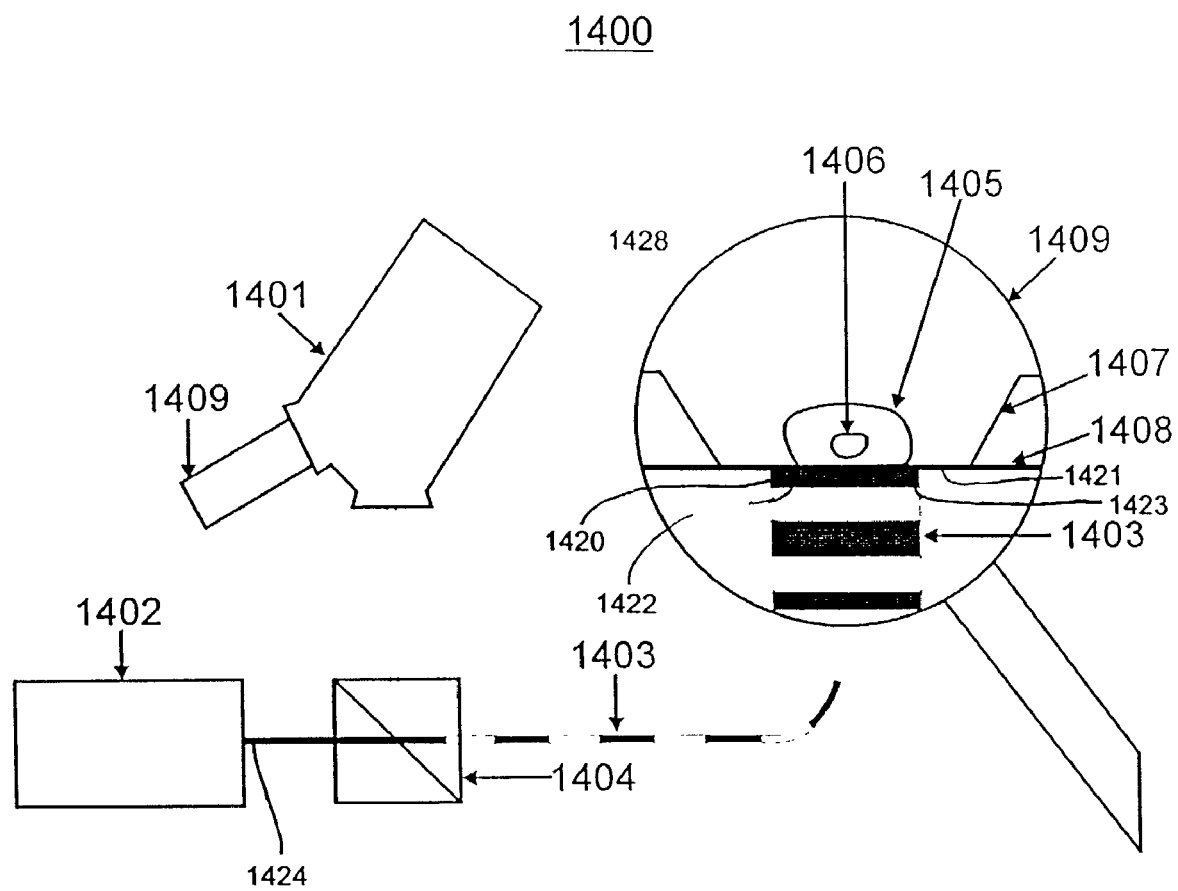
FIG. 14 schematically shows an optical setup for fluorescence measurements associated with a Nanophysiometer according to one embodiment of the present invention.

Moreover, in one embodiment as shown in FIG. 14, the fiber-coupled optical system 1102 can be coupled to an optical detector 1400. The optical detector 1400 has an optional cover slip member 1420 having a first surface 1421 and a second surface 1423, wherein the first surface 1421 of the cover slip 1420 is underneath the chamber 1428 in contact with substrate 1408, and the second surface 1423 of the cover slip 1420 is optically coupled to a first end 1422 of an optical fiber 1403. In one embodiment as shown in FIG. 14, the cover slip member 1420 merges with the first end 1422 of the optical fiber 1403. A light source 1402 optically coupled to a second end 1424 of the optical fiber 1403. A beam splitter 1404 is optically coupled to the optical fiber 1403 and positioned between the light source 1402 and the cover slip 1420 for directing optical signals transmitted through the optical fiber 1403 corresponding to the optical response from a first direction to a second direction. And the optical detector 1400 further has an analyzer 1401 for receiving the optical signals directed by the beam splitter 1404.

In operation, monochometer 1401 selects wavelength of light to be measured by the photodetector 1409. The light source 1402 is coupled to an optical fiber 1403 and the dichroic beamsplitter 1404 that delivers light to the chamber 1428 where a droplet of perfusate 1405 containing at least one cell 1406. The fiber 1403 is coupled through the transparent substrate 1408, which is supported by sidewalls 1407, to obtain the signals regarding the status of the cell 1406.

Note that while the optical detector 1400 is discussed here in connection with a sensor head, the optical detector 1400 can be readily utilized with devices disclosed in other examples of the present invention including the NanoPhysiometer, the well plates, the Microbottles, and the Picocalorimeter.

Additionally, the optical detection method and instrument of the present invention can be combined with any of the sensors disclosed in this specification. The optical detection method and instrument uses an optical fiber technique to illuminate the wells and to extract the fluorescence and luminescence signals. Imaging an entire cell onto a single sensor element offers greatly enhanced signal-to-noise ratios, among other things.

Perhaps with the exception of NADH/NADPH autofluorescence, the optical detection method and instrument may need the introduction of some fluorescent probes into the cell. Some fluorescence dyes do not require direct intracellular access and can be directly incorporated in the sensing platform and read out with the fiber optics system disclosed herein. Optical dyes could be administered and purged through the fluidics channels already incorporated in the cell physiometer.

To enhance the efficiency of wavelength separation, one may use Bragg-filters embedded in the optical fibers. Light indicator can either utilize a photomultiplier or a photodiode.

Example 4

Microbottles

Figure 5A:
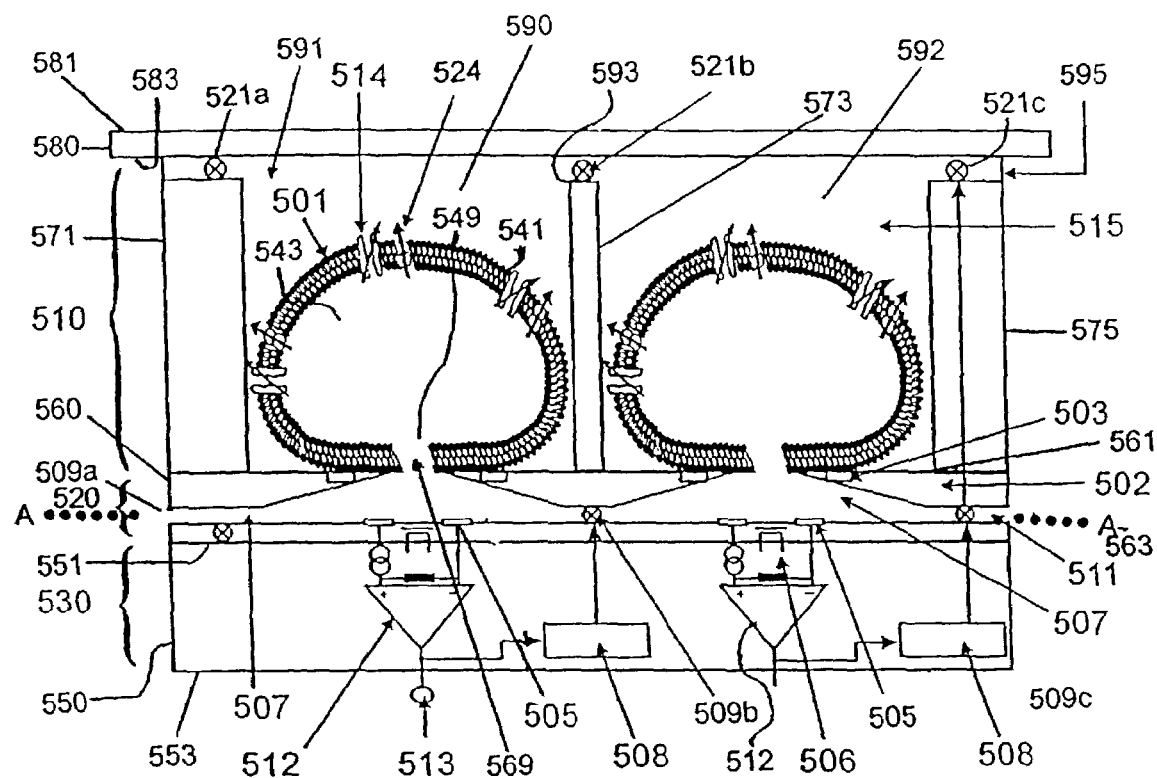
FIG. 5 shows a Microbottle or a device according to yet another embodiment of the present invention: A. side view; B. top view; and C. sectional view along line A-A in FIG. 5A.
Figure 5B:
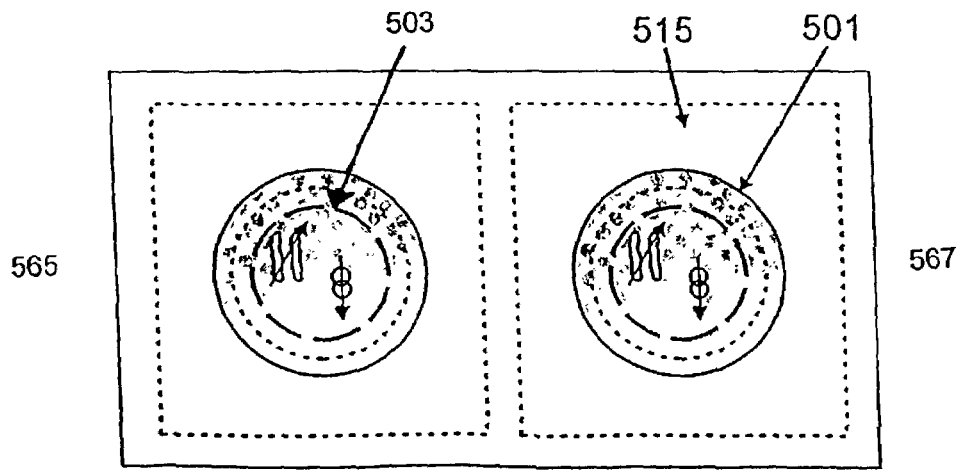
Figure 5C:
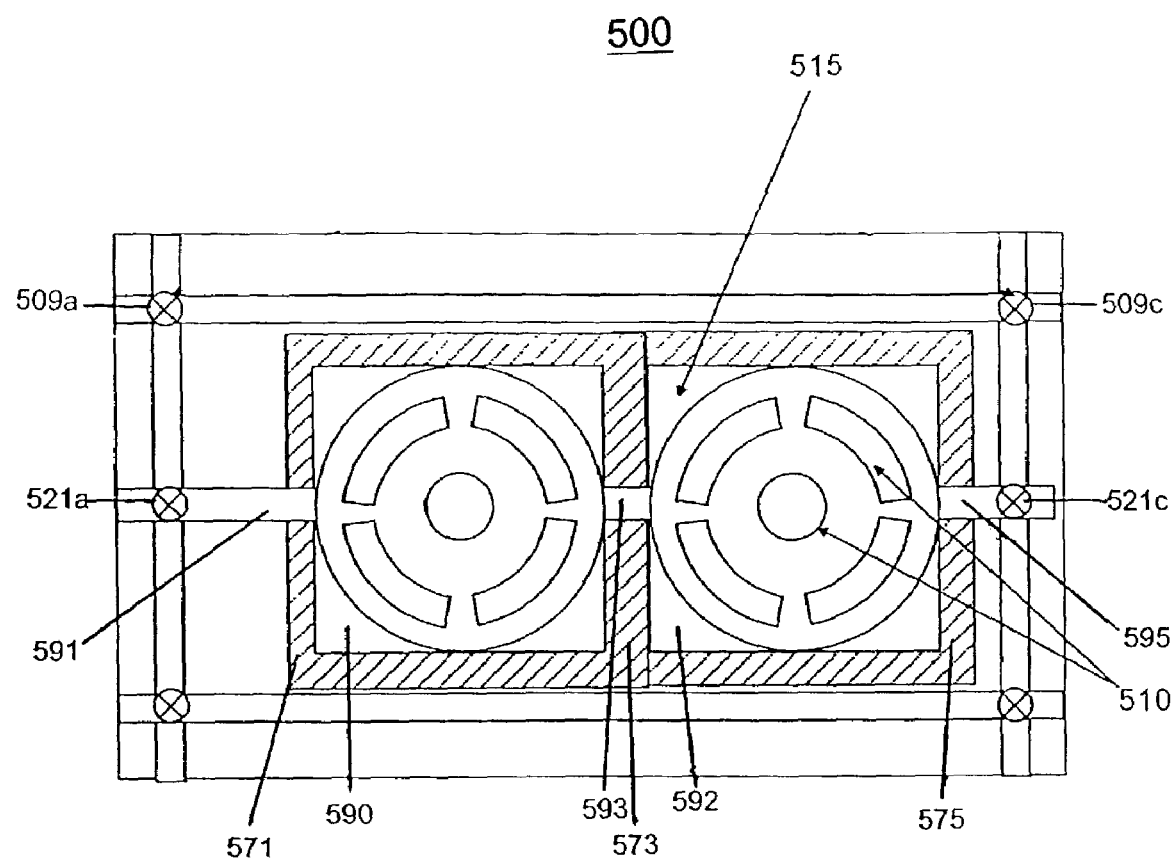
Figure 6A:
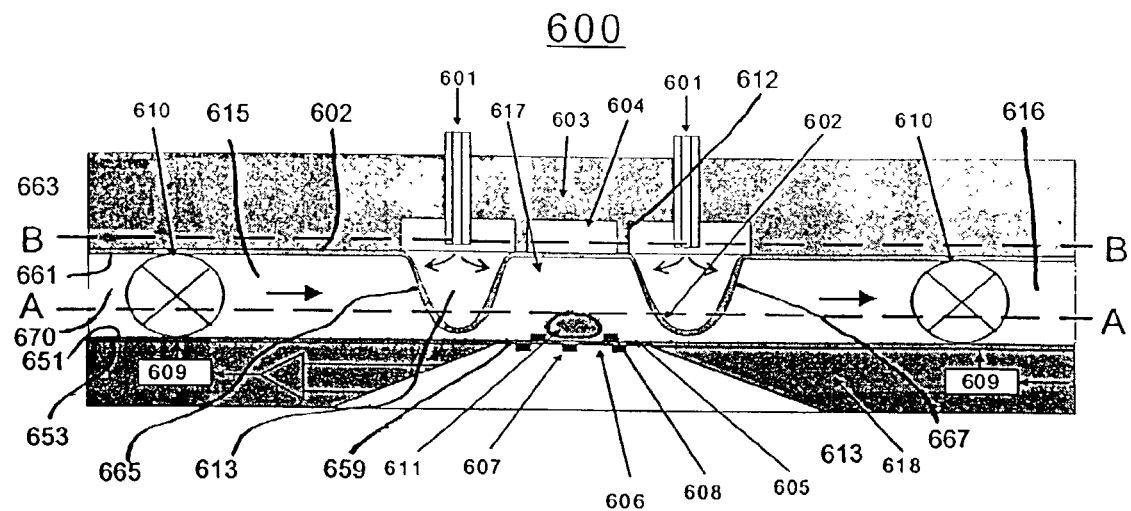
FIG. 6 shows a Picocalorimeter or a device according to one embodiment of the present invention: A. side cross-sectional view along line D-D in FIG. 6C; B. side cross-sectional view along line C-C in FIG. 6C; C. cross-sectional view along line A-A in FIGS. 6A and 6B; and D. cross-sectional view along line B-B in FIGS. 6A and 6B.
Figure 6B:
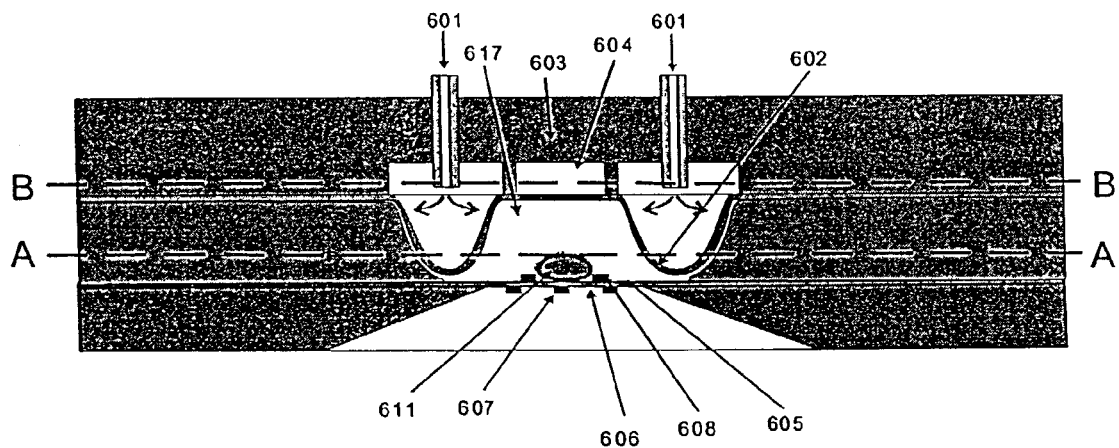
Figure 6C:
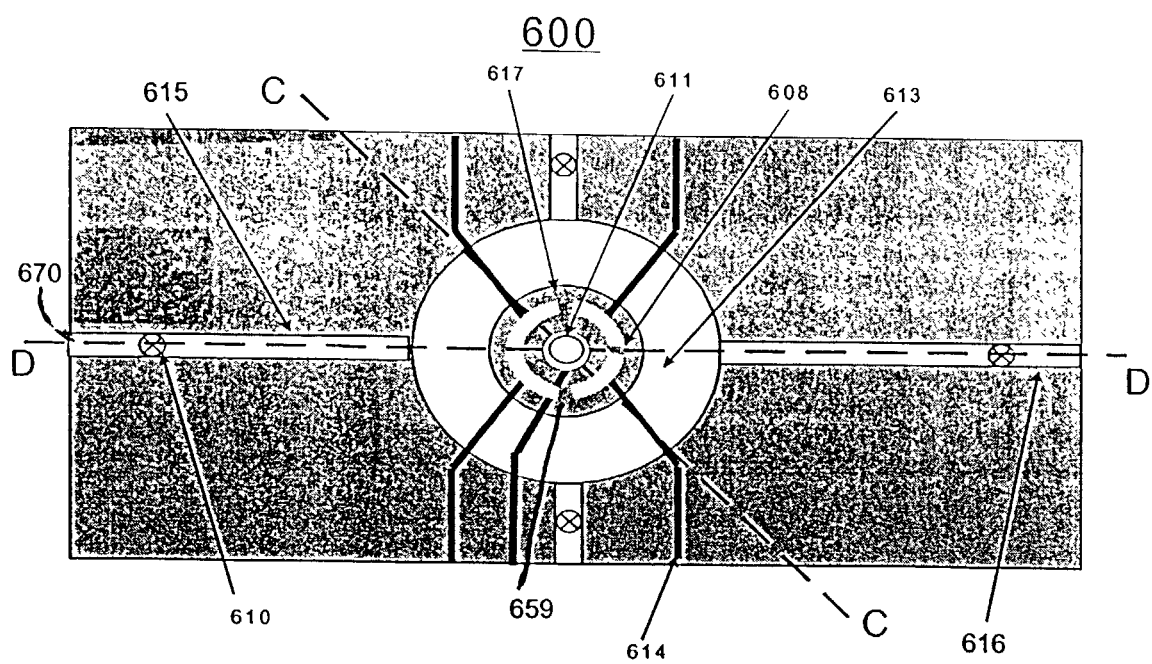
Figure 6D:
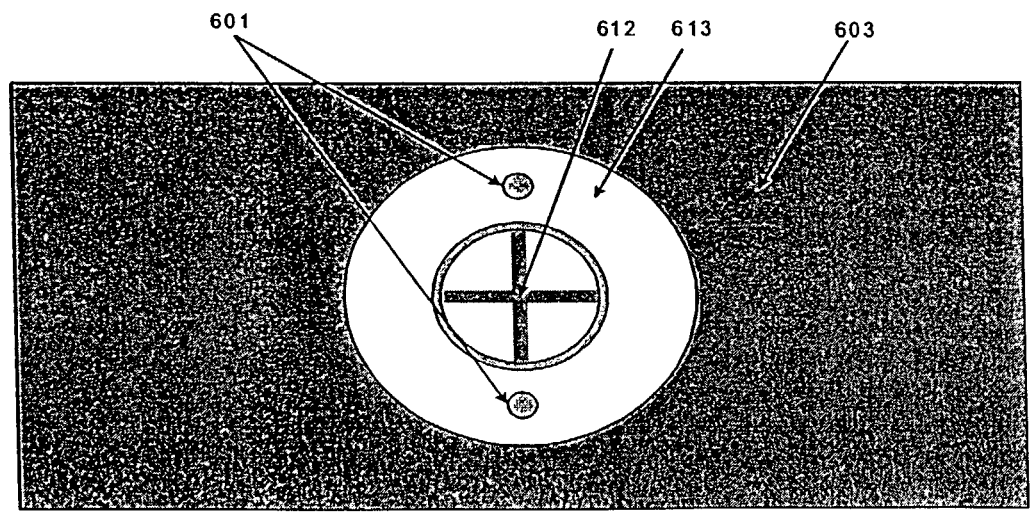
Figure 7A:
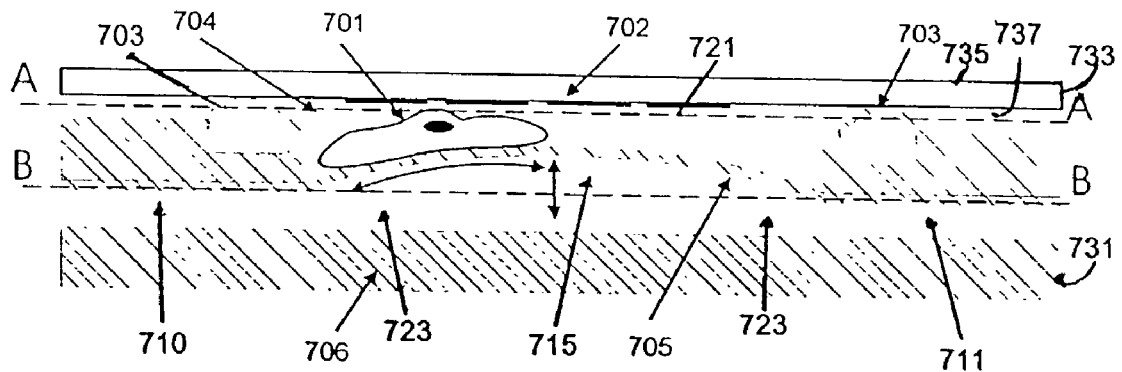
FIG. 7 shows a physiometer or a device according to one embodiment of the present invention: A. side sectional view; B. cross-sectional view along line A-A in FIG. 7A; and C. cross-sectional view along line B-B in FIG. 7B.
Figure 7B:
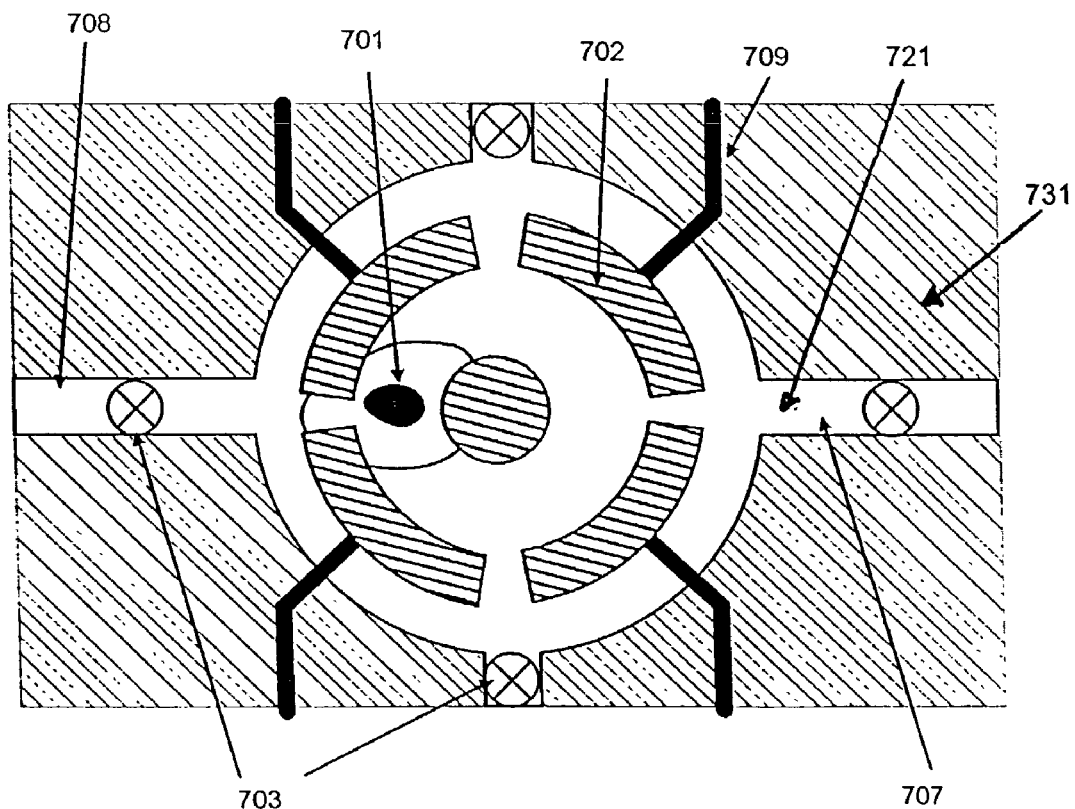
Figure 7C:
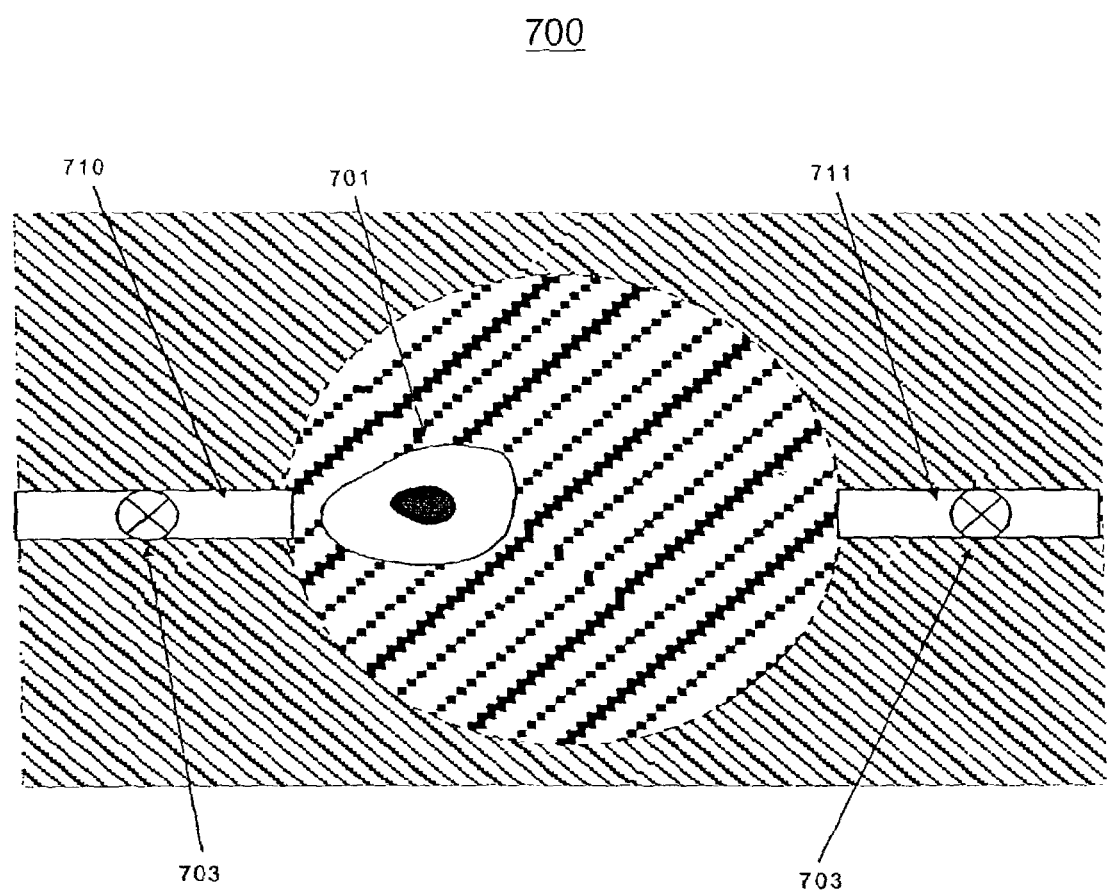

In one aspect, the present invention relates to a device 500 for monitoring status of cell 501 or cells as shown in FIG. 5. In one embodiment as shown in FIG. 5, a device 500 includes a first substrate 550 having a first surface 551 and an opposite second surface 553. The device 500 further has a second substrate 560 supported by the first substrate 550. The second substrate 560 has a first surface 561, an opposite second surface 563, a body portion 502 between the first surface 561 and the second surface 563, a first side surface 565 and an opposite second side surface 567, wherein the body portion 502 defines a first passage 511 between the first side surface 565 and the second side surface 567 and an opening 569 on the first surface 561 of the second substrate 560 and in fluid communication with the first passage 511. Sidewalls 571, 573, 575 are positioned above the first surface 561 of the second substrate 560. The second substrate 560 can be made from semiconductor or insulating materials. In one embodiment, the second substrate 560 is made from silicon.

The device 500 also includes a third substrate 580 having a first surface 581 and an opposite second surface 583. Sensors (not shown) can be added to the second surface 583 of the third substrate 580 having a first surface 581 and an opposite second surface 583 to measure the concentrations of analytes in the extracellular fluid 515 of chamber 590, as can optical sensors 1400 in FIG. 14, to measure intracellular and trans-membrane physiological signatures as discussed above of the cells 501 in chambers 590. The third substrate 580, the sidewalls 571, 573 and the second substrate 560 define a chamber 590 that is in fluid communication with a second passage 591 defined by portions of the sidewall 571 and the third substrate 580. The second passage 591 is in fluid communication with a supply or reservoir of a medium (not shown). As it is shown, optionally, the third substrate 580, the sidewalls 573, 575 and the second substrate 560 define another chamber 592 that is in fluid communication with a third passage 595 defined by portions of the sidewall 575 and the third substrate 580. The third passage 595 is in fluid communication with a supply or reservoir of a medium (not shown). The chambers 590 and 592 are in fluid communication through a passage 593 located therebetween. The device 500 further includes a pair of first controls 509a, 509b positioned inside the first passage 511 for controlling the flow of a medium through the first passage 511 corresponding to chamber 590. Additional first control 509c can be utilized to control the flow of a medium through the first passage 511 corresponding to chamber 592 with or without first control 590b. First controls 509a, 509b, and 509c can work in any pair, in group, or individually. Note that although the device 500 is shown to have a two chamber structure in this embodiment, it can alternatively have a single chamber structure or an N chamber structure, where N is an integer greater than two.

The device 500 further includes at least one sensor 505 positioned in the first passage 511 proximate to the opening 569, wherein a cell 501 is positioned in the chamber 590. In one embodiment, the cell 501 is sealed to the second substrate 560 by at least one gigaohm seal 503. The cell 501 has a membrane 541 forming a substantially enclosed structure and defining an intracellular space 543 therein. The intracellular space 543 of the cell 501 is in fluid communication with the first passage 511 through the opening 569 of the second substrate 560.

The membrane 541 of the cell 501 defines an opening 549 through which the intracellular space 543 of the cell 501 is in fluid communication with the first passage 511 through the opening 569 of the second substrate 560. The device 500 further includes a punching element 506 positioned underneath the opening 569 of the second substrate 560 for making the opening 549 on the membrane 541 of the cell 501. The punching element 560 can be a mechanical device such as a pressure-based suction device (not shown) or an electroporation device such as an electric potential sucking device.

As such formed, the device 500 allows cells with intracellular and extracellular spaces in fluid communication through microfluidic channels such as passages 511, 591, 593, 595.

In one operation mode, when a first medium is introduced into the first passage 511, the intracellular space 543 of the cell 501 is in fluid communication with the first passage 511 with the first medium, the sensor 505 measures the response of the cell 501 to the first medium. The response can be viewed as an intracellular response to the first medium, which may contain agent or agents. The measured signals can be amplified by amplifier 512 to generate an output 513 and/or transmitted to a controller 508 as a feedback, which in turn can control the flow of the first medium through fluid control 509b (and 509a, 509c). The first medium can also be used to provide nutrition to the cell 501 and to maintain the cell 501 at a desired status.

In another operation mode, when a second medium is introduced into the chamber 590 through the second passage 591, at least part of the membrane 541 of the cell 501 is in contact with the second medium in the chamber 590, the sensor 505 measures the response of the cell 501 to the second medium. The response can be viewed as an extracellular response to the second medium, which may contain agent or agents. The measured signals can be amplified by amplifier 512 to generate an output 513 and/or transmitted to a controller 508 as a feedback, which in turn can control the flow of the first medium through fluid control 521a (and 521b). The second medium can also be used to provide nutrition to the cell 501 and to maintain the cell 501 at a desired status.

In yet another operation mode, when a first medium is introduced into the first passage 511 and a second medium is introduced into the chamber 590 through the second passage 591, respectively, the intracellular space 543 of the cell 501 is in fluid communication with the first passage 511 with the first medium and at least part of the membrane of the cell 501 is in contact with the second medium in the chamber 590, the sensor 505 measures the responses of the cell 501 to the first medium and the second medium. From these measurements, the status of the cell 501 can be monitored.

If a plurality of sensors is utilized to practice the present invention, they can be substantially the same. Or, alternatively, at least two of them can be different from each other.

In another application, the device 500 can be utilized to control the physiological status of at least one cell. Normally, a cell controls its physiological status through an internal cellular control mechanism. In one embodiment, the device 500 can be used to provide at least one medium to the cell 501 such that at least part of the membrane of the cell 501 is in contact with the medium to override the internal cellular control mechanism.

In one operation mode, a first medium is supplied into the intracellular space 543 of the cell 501 through the opening 569 in the membrane 541, and a second medium is supplied into the chamber 590 such that at least part of the membrane 541 of the cell 501 is in contact with the second medium. The response of the cell 501 to the second medium is measured, and the composition of the second medium is adjusted based on the response to affect the overriding of the internal cellular control mechanism. Moreover or alternatively, the response of the cell 501 to the first medium is measured, and the composition of the first medium is adjusted based on the response to affect the overriding of the internal cellular control mechanism.

In another operation mode, the concentration of at least one selected component of the medium can be monitored and the composition of the medium can be adjusted based on the monitored concentration of at least one selected component of the medium to affect the overriding of the internal cellular control mechanism.

Still referring to FIG. 5, the device 500 alternatively can be viewed as to have a biolayer 510, a physical layer 520 and an infolayer 530. The biolayer 510 includes chamber 590 that can contain extracellular fluid 515, a living cells 501 with its corresponding transmembrane ion channels and ion-channel complexes 514 and pumps and transporters 515. The intracellular space 543 of the cell 501 through the opening 569 in the membrane 541 is in fluid communication with a fluidic medium 507 that functions as an artificial intracellular medium. The physical layer 520 includes sensing electrodes 505, valves 509a, b, c and other elements such as punching element 506. The Infolayer 530 contains amplifiers 512, reconfigurable digital and analog software programmable digital signal processors 508 and outputs 513. The membrane 514 is sealed to the substrate 502 by the gigaohm seal 503. Microfluidic passages/channels 511 and 509a, b, c allow control of the fluidic contents 507 of the medium and allow intracellular communication between multiple, coupled cells. Valves 521a, b, c allow extracellular communication between cells if needed.

Figure 3A:
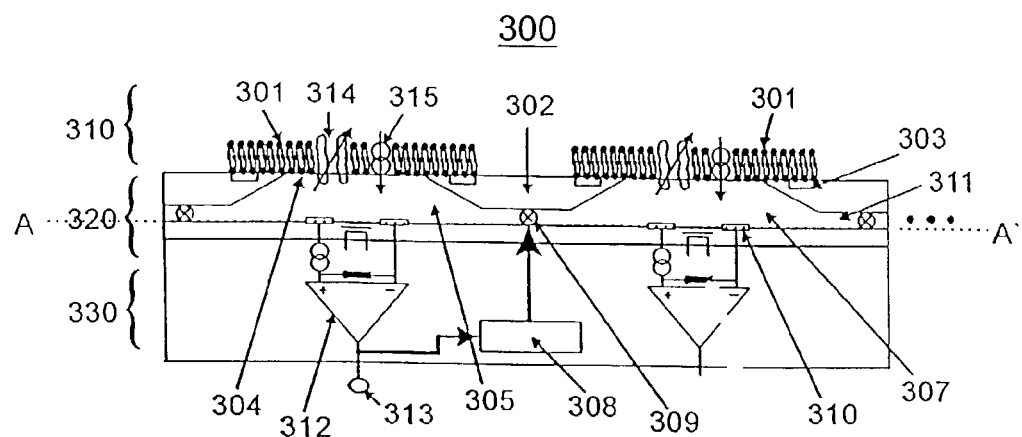
FIG. 3 shows a Microbottle or a device according to one embodiment of the present invention: A. side view; B. top view; and C. sectional view along line A-A in FIG. 3A.
Figure 3B:
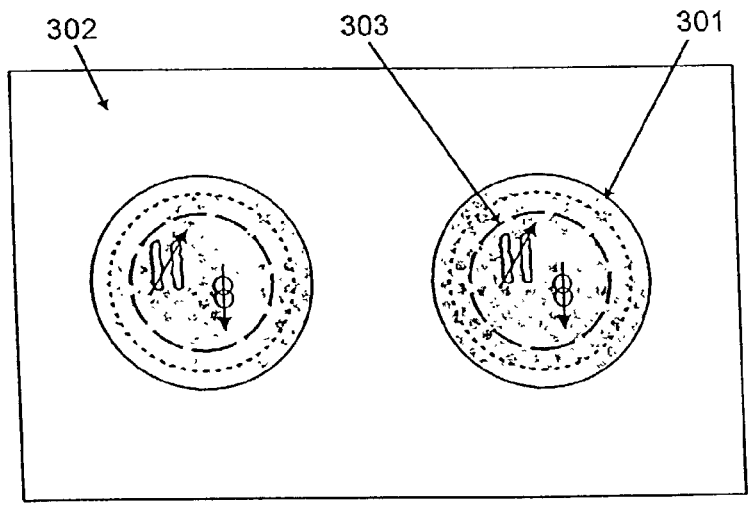
Figure 3C:
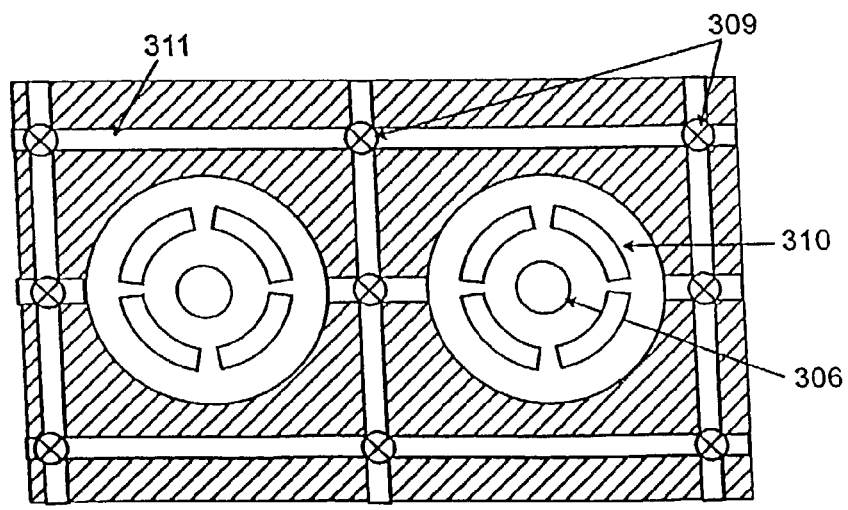

The device 500 according to the present invention may be termed as a "microbottle," which in no way should limit the scope of the present invention. FIGS. 3(A)-(C) shows another embodiment of the microbottle according to the present invention. In FIG. 3, device or microbottle 300 has a biolayer 310, a physical layer 320 and an infolayer 330. The biolayer 310 includes a cellular biological membrane or synthetic lipid membrane 301 containing ion channels or ion-channel/receptor complexes 314 and pumps and transporters 315, such that the inner surface 304 of the membrane 301 is exposed to an fluidic medium 307 that functions as an artificial intracellular medium. The physical layer 320 includes the microbottles, picocalorimeters, microfluidics 305, 307, and sensor/electrodes 310. The infolayer 320 contains amplifiers 312, reconfigurable digital an analog software programmable digital signal processors ("DSPs") 308 and the system output 313. The microbottle 300 has a silicon substrate 302, and the membrane 301 is sealed to the substrate 302 by the gigaohm seal 303. Microfluidic channels 311 and valves 309 allow control of the content of the fluidic contents 307 of the container and allows intracellular communication between multiple, coupled membranes 301.

Figure 4A:
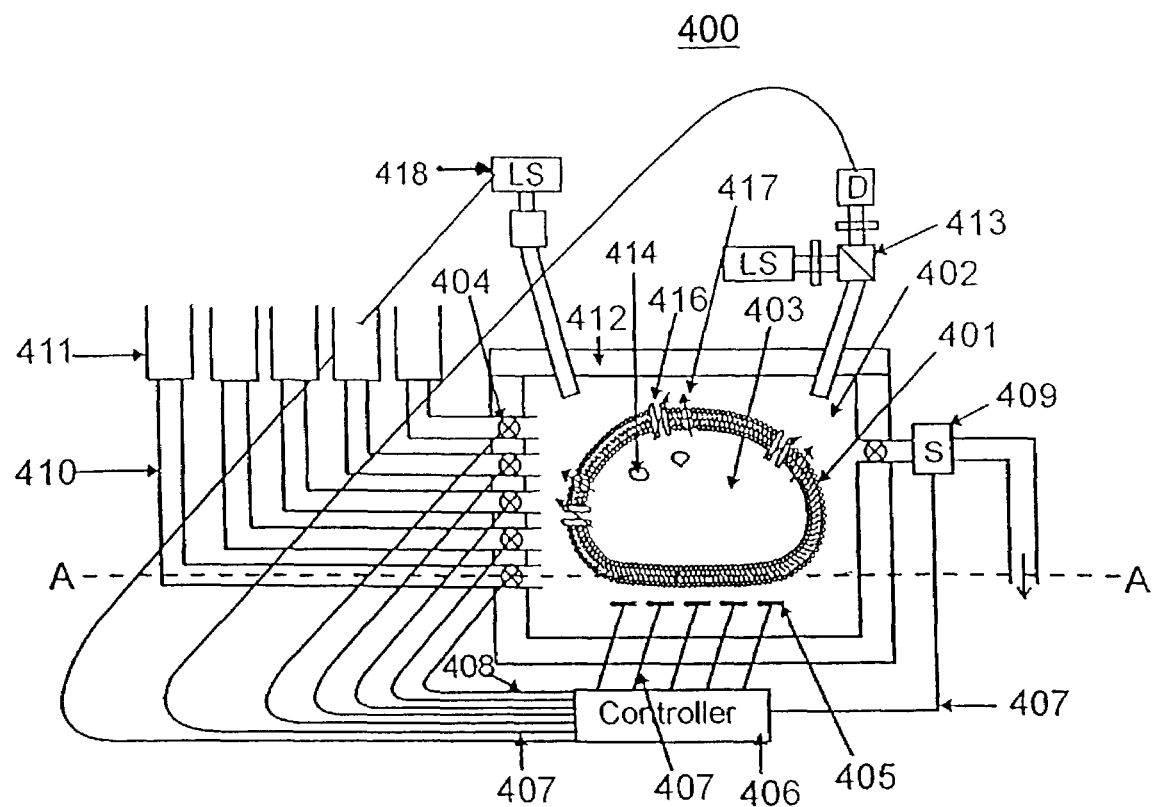
FIG. 4 shows a Microbottle or a device according to another embodiment of the present invention: A. side view; B. top view (with lid removed); and C. sectional view along line A-A in FIG. 4A.
Figure 4B:
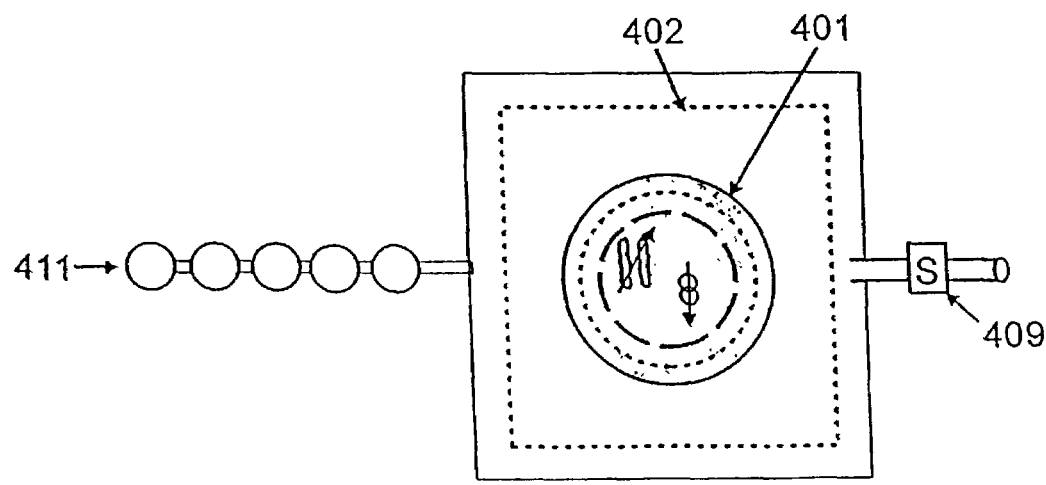
Figure 4C:
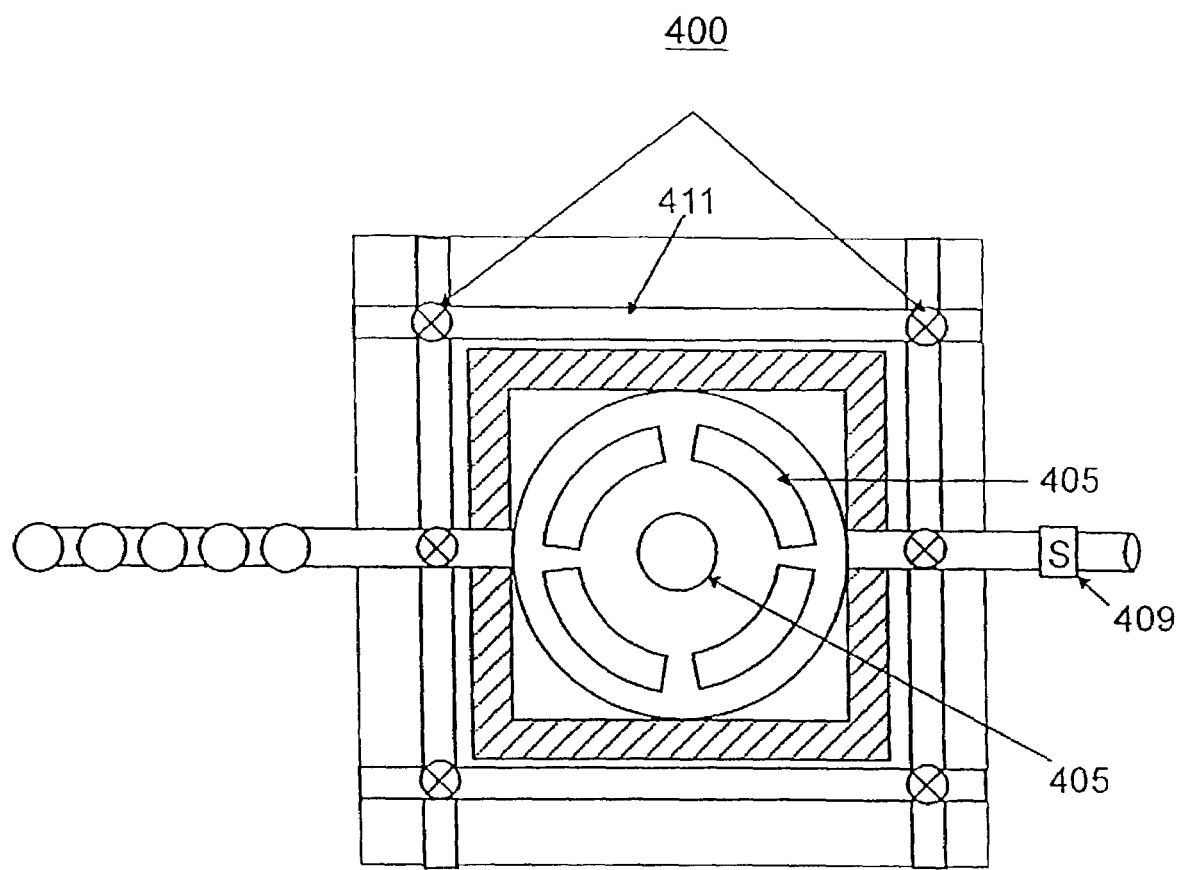

FIG. 4 shows yet another embodiment of the microbottle according to the present invention. In FIG. 4, a living cell 401 is maintained in a chamber 412 whose fluidic contents are maintained by valves 404, which are connected to perfusate reservoirs 411 by microfluidic channels 410. A controller 406 is coupled by sensing leads 407 to sensors 405, 409 and 413 to sense the chemical composition in the extracellular space 402 and the chemical composition and/or state of internal organelles and/or natural or artificial markers 414 in the intracellular space 403. Through control leads 408, the controller 406 then adjusts the valves 404 to maintain the proper extracellular environment and the level of toxin or agents in the reservoirs 411 to which the cell 401 is exposed. The controller 406 can also control the exposure of the cell 401 to light by means of a controlled light source 418 that can be used to alter the conductance of transmembrane ion channels 416 or pumps or transporters 417.

Accordingly, the microbottle provided by the present invention in various embodiments can provide direct interface for measuring and controlling ion concentrations on both sides of a cell or synthetic membrane. The microbottle according to the present invention can be adapted to a variety of applications where the biological element is an active component in the circuit design. The microbottle can be used as a sensing element and allows the release of its content or in case of a cellular cap simulates the cell change cell function. In one embodiment of the present invention, as shown in FIG. 3, the microbottle has a silicon base layer as the focus of the sensing, signal processing and logic, a structural assembly for supporting microfluidics for delivery of ionic species, and a membrane, which is a biologically active element.

As illustrated in FIG. 3, in one embodiment according to the present invention, the microbottle 300 has a layered structure, where each layer can be fabricated individually and assembled in a flip chip manner by conventional bonding techniques. The base layer 310 is a silicon wafer that can be fabricated in conventional CMOS technique containing the sensing elements, actuators, the readout electronic and the logic elements to combine the microbottle in an array structure. The microfluidics layer 330 includes containers/chambers interconnected with channels. The fluids in the channels can be controlled through microvalves and pumps. Each chamber is sealed with an active membrane cap. The membrane could be either biofunctional or biomimetic.

Silicon Base Layer: Microelectronic sensors can be chosen for the measurement of Microbottle input and output parameters. They can be used to control the physiochemical parameters in the silicon container and the environment of hermetically sealed devices. They can also be used to detect changes of the cellular behavior in response to an experimental treatment.

The basic sensor types to monitor the container content of microbottle, among other things, may include microelectrodes, electrochemical sensors, amperimetric sensors, potentiometric sensors, oxygen and other electrochemical sensors and field effects transistors (FET), where the gate electrode is made of or is coated with an electrochemically active material. This material can affect the source/drain current by binding charge from the contents in the microbottle to its surface, creating a voltage drop across the gate insulator. FET-based sensors can be used for different measurement tasks. The addition of special chemical membranes on the gate insulator of a basic-FET allows the realization of ISFETs (Ion sensitive FETs) for different ions ($Ca^{2+}$, $Na^+$, $K^+$, ...) or ENFETs (enzyme sensitive FETs) for other metabolites (glucose, lactose, ...). Typical sensitivities of ISFETs are 50 mV/pH and 30 mV/pNa(pK) for FETs made with $Si_3N_4$ and $Al_2O_3$ gate insulators, respectively. ENFETs for glucose currently have slow response times (3-5 min) and go into saturation. Sensors for the neurotransmitters adrenaline and serotonin incorporate the use of Au nanoparticles they reach sensitivities of $1\times10^{-6}$ M and $6\times10^{-3}$ M, respectively. Typical ISFET sensing gate areas are large, typically 400 μm×20 μm, to maximize their sensitivity.

Microelectrodes can be used to measure potential differences between the inside of the Microbottle and a reference electrode that will be either in a different container or on the other side of the membrane cap. The electrode material is very important in this type of application. Corrosion must be taken into account and avoided in order to make accurate, repeatable measurements. Possible electrode materials include gold and silver (Ag-AgCl). Since FETs and microelectrodes are fabricated using standard microelectronic processes, integrating them with standard CMOS preamplifier and signal processing logic is feasible. While the processes are similar, the materials needed to form the FET gates and the microelectrodes are not standard to CMOS processing. Therefore, careful consideration should be made to the integration of these possibly incompatible materials together in a single "chip". Also proper passivation materials can be utilized to prevent ionic contamination from the cellular solution in CMOS devices. The integration of these specialized sensors with the CMOS circuitry may increase the performance of the Microbottle and enable the coupling of various Microbottles to form programmable multicellular units.

Microfluidics: The micro fluidics layer allows the control of fluids on both sides of the membrane cap. The microfluidics layer can be either anodic or fusion bonded to silicon layer containing sensing and control elements. Some embodiments are shown and disclosed in the specification using liquid PDMS BioMEMS fabrication technology. In one embodiment, alternatively, a microfluidics layer includes channels and silicon containers with submicron holes. The channels and containers are etched into the substrate by Reactive Ion Etching (RIE) of silicon nitride mask and a non-isotropic KOH etch. The silicon nitride mask is typically less than one micron thick and can also be used for membrane structures without additional fabrication steps. The pyramidal container is therefore spanned with a silicon nitride membrane. The submicron hole in the membrane can be fabricated by focused ion beam.

The channels can be connected to tubing leading to external valves and pumps. Active and passive valves can be incorporated as well. A passive valve acts as flow restrictor and includes a metal and a polyamide membrane with holes in different positions. An active valve includes an electrostatic- or pneumatic-deflectable membrane on a segmented hole.

Device Fabrication: The etching of channels and insulation layers, the fabrication of the boron-doped diamond microelectrodes, and the nanoscale machining such as the drilling of the holes for the Microbottle are developed accordingly for the present invention. The oxygen sensor, MEMS microfabrication, thermometer deposition and micromachined infrared detectors are also developed and utilized.

Membrane Cap: In one embodiment, the silicon container is spanned by either a biological membrane harvested from a cell (approximately 10 μm) or by a synthetic membrane assembled on the microfluidics layer. The membrane forms a seal not only acting as chemical barrier but also preventing leakage of currents from the Microbottle electrode to the reference electrode. The resistance is critical for determining the electrical background noise from which the channel currents need to be separated. In a typical patch clamp experiment, where the membrane is attached to a glass pipette the resistance is typically gigaohms. Active elements like voltage sensitive channel are inserted into the membrane cap and are either used as sensors or actuators. The voltage sensitive channels could be switches with an electrode configuration on the rim of the hole.

Synthetic Membrane: One of the common applications of lipid bilayers has been to study ion channel transport characteristics. Several issues are important in the application of bilayers as biosensors. The most critical physical properties are membrane uniformity and membrane stability and the present invention is capable of addressing these issues. Lipid bilayers have been deposited on solid platinum, gold and silicon surfaces. There are several examples of bilayer spanning applications such as across micromachined polyimide 40 μm diameter apertures. The microbottle may be temporarily filled with a support material, while the bilayer is formed. An enzymatic cleavage strategy can be utilized to remove the gels through the fluid channel access ports of the microbottle. The individual molecules forming ion channels can be inserted in artificial lipid bilayers. Far more complex systems, which employ high-gain biological amplification and therefore the detection of single molecules, e.g., hormone receptor systems, may also be employed.

Natural Membrane: The Microbottle according to the present invention allows fluids to be sucked through one of the holes in the silicon container. By sucking and manipulating a cell onto the top of the silicon container the cell membrane can be punched open allowing access to the intracellular space. Natural membrane can be extracted from various different cells by rupturing the cell membrane.

Cellular Cap: The Microbottle of the present invention allows fluids to be sucked through at least one hole in the silicon container. By sucking and manipulating a cell onto the top of the silicon container the cell membrane can be punched open allowing fluidic and electrical access to the intracellular space. The extracellular space can also be monitored through a second fluidics layer encapsulation the cell. The cell is now an active elements; the intra- and extra cellular space is monitored and controlled through the silicon base layer and the microfluidics layers. Such an embodiment is shown in FIG. 5. The immediate spin off this technology is a new measurement technique with unsurpassed possibilities superseding conventional patch clamp techniques. Small pore diameters can only be obtained in glass micropipettes if the cone angle is very small and the pipette resistance correspondingly high, the RC noise generated by this resistance in conjunction with the distributed pipette capacitance limits the bandwidth of voltage recordings dramatically. The long conical shape of the glass micropipette also restricts the selective perfusion of the intracellular space. In contrast, the Microbottles does not impose geometrical constrictions and allows the controlled fabrication of ultra small pores beyond the capabilities of glass pipettes. The low access resistance of the silicon micropipette used with small membrane patches brings the potential of voltage clamping in the megahertz frequency domain. The present invention also allows temporal resolution of a variety of important electrogenic events such as ion-binding reactions and fast conformational changes associated with transport function.

In tiny patches the probability of the appearance of any other charge-translocation processes is reduced in proportion to the patch area. Furthermore the formation of a reliable seal becomes increasingly more difficult as the size of the pipette tip is increased. The wide planar rim of the silicon chip utilized in the present invention is expected to reduce the shunt resistance, leads to a greater stability and a significantly higher success rate in a patch clamp process. In general the stability of those small patches is expected to be enormously high with a seal resistance of several hundred gigaohms allowing long-term recordings. The microbottle would not only simplify and overcome the limitations of patch-clamp techniques but also move towards integrating biologically active components into electronic circuits on silicon wafers.

A plurality of Microbottles of the present invention can be arranged in complex array structures allowing to readout and stimulation of cellular networks. The cellular network would be fabricated with a technique called soft lithography. According to one embodiment of the present invention, in the first step pits and connecting channels are etched into silicon substrates. After etching, the channels and pits are coated with an adhesive protein (polylysine), which promotes cell adhesion and cell growth. After coating, neural or cardiac cells are platted onto the silicon substrate the cells adhere in the pits and form dentrides along the channels connecting to neighboring cells. The chip with the patterned cellular networks is "flip chipped" to the silicon wafer containing the Microbottles. Since the Microbottles probe and control the intracellular space, a well-defined cell-silicon coupling can be realized. Conventional techniques like microelectrode arrays or cell potential FETS (CPFETs) suffer from poor coupling and therefore reduced signal amplitudes. Recordings are generally on the order of 10-200 µV compared to 80 mV in patch clamp techniques.

Example 5

Picocalorimeter and Bioreactor

Figure 2A:
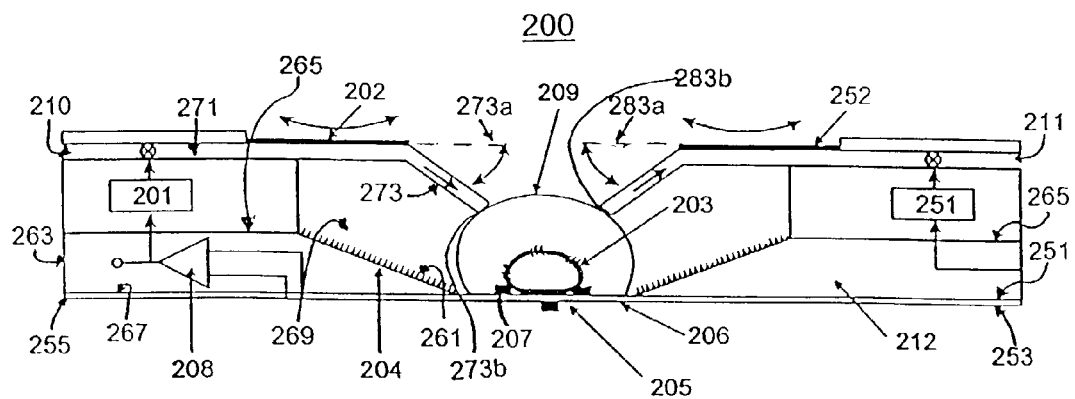
FIG. 2 shows a PicoCalorimeter or a device according to one embodiment of the present invention: A. side view and B. top view.
Figure 2B:
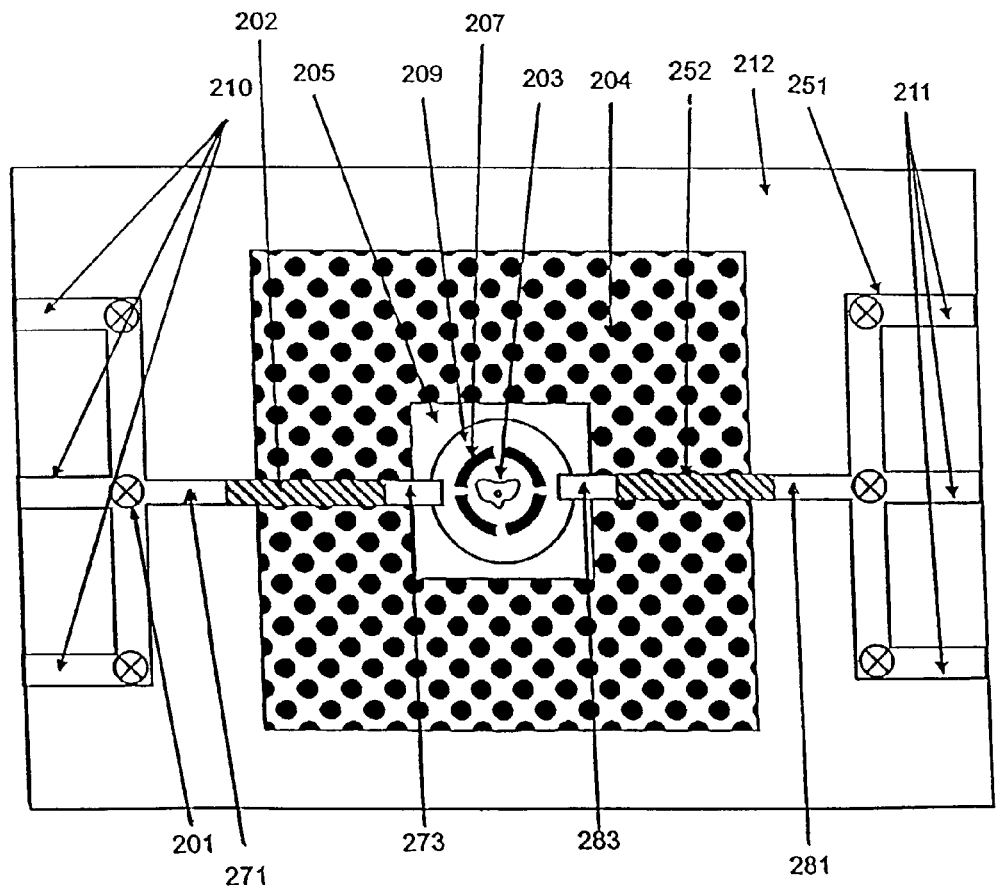

In one aspect, the present invention relates to a device for measuring response of at least one cell 203 to a medium, the response of at least one cell 203 to a medium being characterized by a reaction time. In one embodiment as shown in FIGS. 2A and 2B, a device 200 includes a membrane 206 having a first surface 251, an opposite second surface 253 and edges 255, a side substrate 212 having an inside surface 261, an opposite outside surface 263, a top surface 265 and bottom surface 267, wherein the inside surface 261 of the side substrate 212 and the first surface 251 of the membrane 206 define a sample well 269 in communication with the ambient air and for receiving the at least one cell 203 such that the membrane 206 is underneath the at least one cell 203, a sensor 205 positioned underneath the second surface 253 of the membrane 206, and an inlet 210 in fluid communication with the sample well 269. A medium (not shown) is introduced into the sample well 269 through the inlet 210 to form a droplet 209 that surrounds the cell 203, and the sensor 205 measures the response of the cell 203 to the medium at a time period shorter than the reaction time. The sensor 205 is in contact with the second surface 253 of the membrane 206. The response of the cell 203 to the medium, which may contain at least one agent or stimuli, depends on the characteristic of the cell 203 as well as the properties of the agent such as the type or class of the agent. Therefore, among other things, one application of the device 200, and other device 200s and methods of the present invention, is to detect the agent from the response of the cell 203 to the medium having the agent, which uses the cell 203 as canary.

The device 200 also includes a biocompatible coating layer (not shown) applied to the first surface 251 of the membrane 206. The membrane 206 comprises a material with sufficiently low thermal conductivity to yield a high degree of thermal isolation between the center of the membrane 206 and the edges. For examples, the membrane 206 may comprise a dielectric material. The membrane 206 may also comprise a silicon nitride membrane 206. Moreover, the membrane 206 is at least partially transparent so that the response of the cell 203 can be optically detected through an optical sensor.

The inside surface 261 of the side substrate 212 makes contact with the first surface 251 of the membrane 206 to define the sample well 269, wherein the side substrate 212 is thermally isolated from the membrane 206. A hydrophobic layer 204 can be applied to the inside surface 261 of the side substrate 212.

In one embodiment as best shown in FIG. 2A, the inside surface 261 of the side substrate 212 has a slope defined by an angle α such that cross-sectionally the bottom surface 267 of the side substrate 212 is wider than the top surface 265 of the side substrate 212. The side substrate 212 comprises a material with sufficiently high thermal conductivity such that the side substrate 212 functions as a heat sink for the membrane 206. For examples, the side substrate 212 may comprise a semiconductor material such as silicon.

The sensor 205 can be any type of sensor as defined and discussed above. As an example shown in FIGS. 2A and 2B, the sensor 205 can be a thermal detector.

The device 200 further includes an actuator 202 that is mechanically coupled to the inlet 210. The inlet 210 has a main portion 271 and an end portion 273 in fluid communication with the main portion 271. The end portion 273 is movable between a first position 273a that is distant from the cell 203 and a second position 273b that is proximate to the cell 203. When a medium is to be introduced into the sample well 269, the actuator 202 causes the end portion 273 to move away from the first position 273a to the second position 273b or a position therebetween the first position 273a and the second position 273b for delivering the medium to the sample well 269 to form a droplet 209 to isolate the cell 203. After a medium is introduced into the sample well 269 and droplet 209 is formed, the actuator 202 can cause the end portion 273 to move toward to the first position 273a from the second position 273b or a position therebetween the first position 273a and the second position 273b for keeping the end portion 273 away from the droplet 209 isolating the cell 203.

The device 200 further has a control 201 positioned inside the main portion 271 of the inlet 210 for controlling the flow of the medium. Additional controls 201 can be positioned at branches in fluid communication with main portion 271, as best shown in FIG. 2B, such that the content of the medium can be adjusted as needed.

The device 200 also has an outlet 211 in fluid communication with the sample well 269 for introducing medium away from the sample well 269. An actuator 252 mechanically coupled to the outlet 211. The outlet 211 has a main portion 281 and an end portion 283 in fluid communication with the main portion 281. The end portion 283 is movable between a first position 283b that is proximate to the cell 203 and a second position 283a that is distant from the cell 203. When a medium isto be introduced away from the sample well 269, the actuator 252 causes the end portion 283 to move away from the first position 283b to the second position 283a or a position therebetween the first position 283b and the second position 283a for introducing the medium away from the sample well 269. After a medium is introduced away from the sample well 269, the actuator 252 may cause the end portion 283 to move back to the first position 283b from a position therebetween the first position 283b and the second position 283a. The device 200 further has a control 251 positioned inside the main portion 281 of the outlet 211 for controlling the flow of the medium. Additional controls 251 can be positioned at branches in fluid communication with main portion 281, as best shown in FIG. 2B, such that the content of the medium can be adjusted or controlled as needed.

Thus, a device according to the present invention is shown to be able to measure the energy generation and consumption of a single or multiple cells. In some embodiments, such a device is termed as a Picocalorimeter. As shown in FIGS. 2A and 2B, in operation, device 200 uses a membrane 206 in combination with a sensor 205 to measure measurable quantities related to the status of a single or multiple cells such as the basal energy generated by a cell 203 in a droplet of culture media 209. The droplet of cell culture media is confined on the membrane 206 by a hydrophobic coating 204. The temperature difference between the membrane and the substrate 212 is measured with sensor 205, which can be a differential sensor and may be coupled to additional components such as an amplifier 213 through leads 214. The content of the droplet 209 can be exchanged to maintain cell viability using inlet 210 that can have an optional branch structure formed by a number of inlet lines 217 as shown. The content of the inlet structure can be varies using valves 201, which are driven by controller 208. For analysis of the content in the outflow through outlet structure, the fluid can be switched by valves 251 to have various analyzing structures formed by a number of outlet lines 218. The inlet structure 210 can be positioned by actuator 202 to inject fluid into the droplet and to retract from the droplet 209 to maintain thermal insulation, respectively. The outlet structure 211 can be positioned by actuator 252 to withdraw fluid from the droplet 209 and to retract from the droplet 209 to maintain thermal insulation, respectively. During the measurement interval the inlet and the outlet structure are retracted. Additional electrodes 207 can be used to monitor various metabolites in the droplet 209 in order to detect, for example, metabolic pathway switching. Controller 208 allows the analytes in the media to be changed depending on the status of the metabolic network in order to override internal cellular control.

Moreover, in another embodiment (not shown), MEMS and microfluidic technologies are utilized to provide a flow-through system in which the heat production of a small number of cells may be monitored before and after the cell stream merges with the injected flow of medium containing agent such as toxin. Micropipes can be electrically actuated by piezo bimorphs so that they can be separated from the droplet to thermally insulate the cell on the membrane in the thermal measurement interval. Beside heat generation, oxygen, pH and Redox potential sensors can be integrated on chip as well as advanced readout and control electronics.

Figures 25A, 25B:
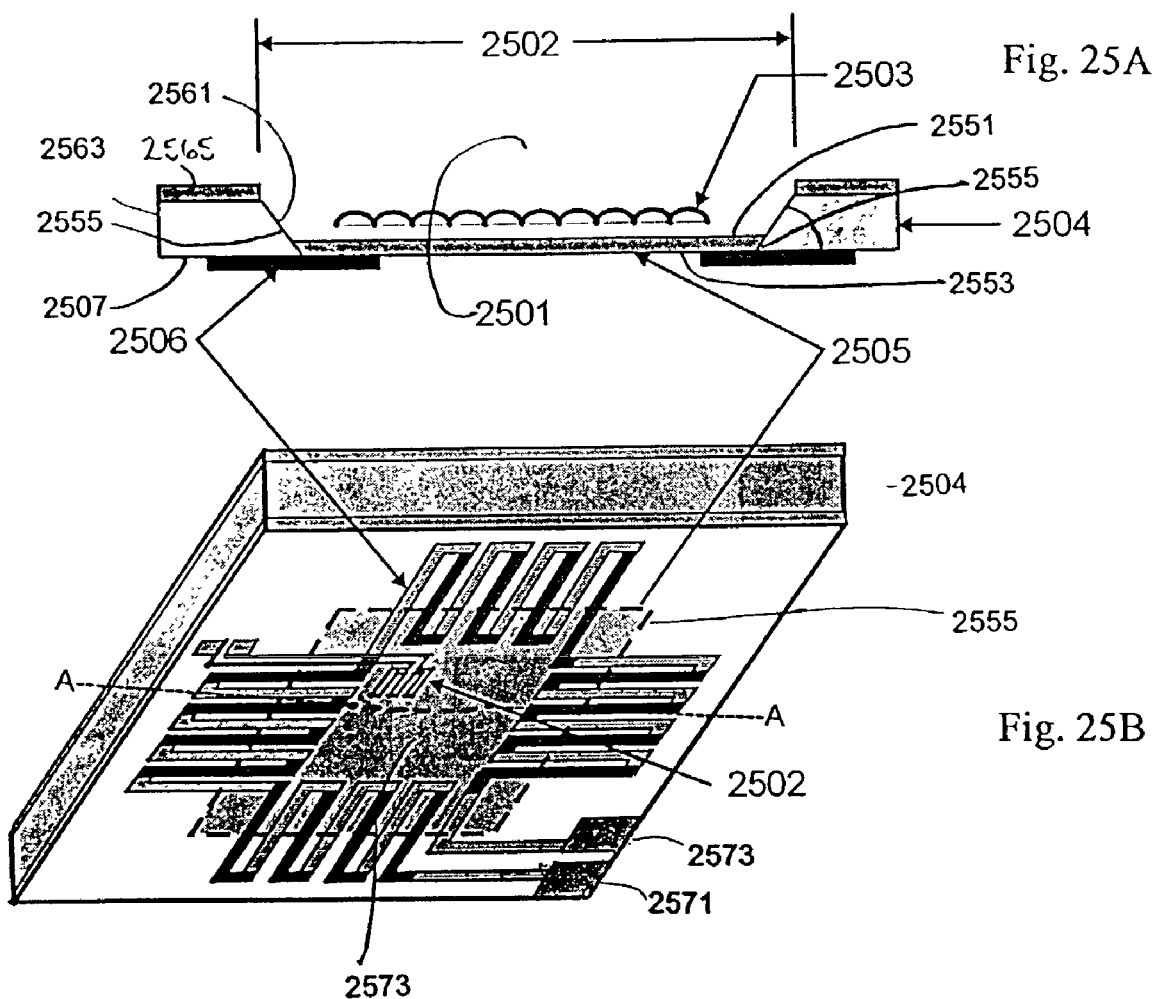
FIG. 25 shows a Picocalorimeter or a device according to another embodiment of the present invention: A. side cross-sectional view along line A-A in FIG. 25B; and B. tilted view from the bottom.

In another aspect, the present invention relates to a device for measuring at least one of cellular physiological activities of at least one cell or cells, where each of the cellular physiological activities can be characterized by a reaction time. In one embodiment as shown in FIGS. 25A and 25B, the device 2500 includes a membrane 2505 having a first surface 2551, an opposite second surface 2553 and edges 2555, a side substrate 2504 thermally isolated from the membrane 2505 and having an inside surface 2561, an opposite outside surface 2563, a top surface 2565 and bottom surface 2567, wherein the inside surface 2561 of the side substrate 2504 cooperates with the first surface 2551 of the membrane 2505 to define a sample well 2501 in communication with the ambient air and for receiving the at least one cell or cells 2503 such that the membrane 2505 is underneath the at least one cell 2503, and a sensor 2506 positioned underneath the second surface 2553 of the membrane 2505 for measuring at least one of cellular physiological activities of the at least one cell 2503. The membrane 2505 and the sensor 2506 are arranged such that at least one of cellular physiological activities of the at least one cell 2503 is measured at a time period shorter than the reaction time. Note that among other things, one advantage of the device 2500 is that it allows operation in air, which makes the utilization of living cells possible and also eliminates many disadvantages related to the requirement of operation in vacuum by the prior art such as cost, inconvenience, low reliability, etc.

As discussed above and below related to the present invention, among other things, it can be done by limiting the dimensions of the device, positioning the sensor(s) proximate to the cell(s), and/or choosing cellular physiological activities to be measured such that quantities related to the status of a cell, being a response to an agent or a cellular physiological activity, can be obtained quickly before a corresponding reaction time such as a diffusion time. Thus, one uniqueaspect of the present invention is that small is faster and better. It will be appreciated, however, that in addition to a reaction time that characterizes a response to an agent or a cellular physiological activity of a cell, other quantities may be considered as well. For examples, in one embodiment, the device 2500 can be utilized to detect signals corresponding to the amount of heat generated by cells as a function of time or intervention. This can either be as a measurement of power, or total energy change. The characteristics of the media that are in fluid communication with the cells include the thermal conductivity and the heat capacity. These may combine to give the response time and response amplitude for the system when cells within the sample well produce heat. Device 2500, like other embodiments of the present invention, allows one to obtain proper signals at proper places within a proper time period.

The device 2500 also may include a biocompatible coating layer (not shown) applied to the first surface 2551 of the membrane 2505 for better housing the cells 2503. The membrane 2505 comprises a material with sufficiently low thermal conductivity to yield a high degree of thermal isolation between the center of the membrane 2505 and the edges 2555. For examples, the membrane 2505 may comprise a dielectric material. The membrane 2505 may also comprise a silicon nitride membrane 2505. Moreover, the membrane 2505 is at least partially transparent so that the response of the cell 2503 can be optically detected. The dimensions of the membrane 2505 can be chosen such that measurements can be performed at a desired time period that is shorter than a corresponding reaction time. For examples, in one embodiment as shown in FIGS. 25A and 25B, the thickness of the membrane 2505 is in the range of 0.1 to 1.5 μm, and the size of the membrane 2505 is in the range of 0.1 to 25 mm$^2$. In a particular example, the thickness of the membrane 2505 is chosen as about 0.6 μm, and the size of the membrane 2505 is chosen as about 1 mm$^2$.

The inside surface 2561 of the side substrate 2504 makes contact with the edges 2555 of the membrane 2505 to define the sample well 2501, wherein the side substrate 2504 is thermally isolated from the membrane 2505. A hydrophobic layer (not shown) can be applied to the inside surface 2561 of the side substrate 2504.

In one embodiment, the inside surface 2561 of the side substrate 2504 has a slope with an angle β such that cross-sectionally the bottom surface 2567 of the side substrate 2504 is wider than the top surface 2565 of the side substrate 2504. The side substrate 2504 comprises a material with sufficiently high thermal conductivity such that the side substrate 2504 functions as a heat sink for the membrane 2505. For examples, the side substrate 2504 may comprise a semiconductor material such as silicon.

Again, the sensor 2506 can be any type of sensor 2506 as defined below. As an example, the sensor 2506 can be a thermal detector. In one embodiment as shown in FIGS. 25A and 25B, the thermal detector 2506 comprises a thermometer, wherein the thermometer comprises a thermopile having a first polarity of junction positioned underneath and in contact with the second surface 2553 of the membrane 2505 and a second polarity of junction thermally coupled to the side substrate 2504. The thermopile includes a series of thermocouples, wherein an emf measured at the leads of the thermopile is proportional to the temperature difference between the membrane 2505 and the side substrate 2504. Alternatively, the thermometer can be a resistive thermometer having a series of resistors electrically coupled to each other. Additionally, other sensor(s) can be utilized to cooperate with the thermal sensor 2506. For instance, an optical sensor (not shown) can be utilized to optically detect the status of the cells 2503 through an at least partially transparent area 2573 of the membrane 2505.

Thus, a Picocalorimeter according to one embodiment of the present invention combines the highly complex and evolved sensing architecture of cellular systems and a new micro-machined silicon transducer device capable of detecting minute heat changes arising from changes in the metabolism of a single cell with a response time of a few milliseconds. The Picocalorimeter, with a sensitivity of 1-50 pW, results in an improvement of more than four orders of magnitude and hence achieve single cell sensitivity. The measured specifications of micromachined calorimeters, and calculated values for optimized shown in the following table.

| Specification | Measured: existing prototype | Calculated: optimized device |
| --- | --- | --- |
| Detector area | 1 mm$^2$ | [0.3 mm]$^2$ |
| Responsivity | 110 volts/watt | 1365 volt/watt |
| Noise | 110 nV/√Hz | 80 nV/√Hz |
| Time constant | 50 msec | 15 msec |
| Minimum detectable power | 1000 picowatt/√Hz | 59 picowatt/√Hz |
| Energy Sensitivity, τ = 10 s | 130 picojoule | 7 picojoule |

The Picocalorimeter can be fabricated by employing micro-machining techniques. As discussed above, a Picocalorimeter includes a silicon nitride (SiN) membrane, thermally insulated from the silicon wafer, and one or more thermometers in the center of the membrane. The thermometer is typically a series of resistors or thermocouples forming a thermopile. The heat quantity evolved or absorbed is equal or proportional to the product between temperature change and the heat capacity of the calorimetric vessel and its contents. Since the membrane dimensions are small and silicon nitride has an extremely low-thermal conductivity and heat capacity, the device is intrinsically sensitive. By minimizing the total thermal conductance, a small quantity of heat transferred to or from the sample results in a large, measurable temperature rise. For the optimized device, about 20 μW of power will raise the Picocalorimeter temperature by 1 K. The mK sensitivity of the thermometer gives pW resolution. This may be achieved by employing micromachining fabrication to produce a rigid membrane only 0.6 μm thick or less.

The contents of the Picocalorimeter can be single or multiple cells grown or placed onto the SiN membrane and a drop of liquid surrounding the cell. Several measurements on membranes have shown a high mechanical stability of the silicon nitride membrane and its ability to support a liquid droplet, and growing cells directly on the membrane. The liquid contains all required nutrients and may be periodically exchanged by two nanoliter injectors (not shown) between measurement intervals. Two nanoliter injectors are mounted on computer-controlled micro-positioners, which can also be used to position the cells on the SiN membrane or to introduce agents that alter the metabolism of the cell. The following table shows the metabolic activity of various cell lines of interest.

| Cell types | Power/heat output | Reference |
| --- | --- | --- |
| Human T-lymphoma cell | 12.2 pW/cell | P. Backman, 1991 |
| Human melanoma cells | 80 pW/cell | M. Gorman-Nordmark et. al 1984 |
| Rat white adipocytes | 40 pW/cell | P. Nilsson-Eble et. al 1985 |
| 3T3 mouse fibroblasts | 17 pW/cell | P. Lonnbro et. al 1990 |
| Rat hepatocytes | 329 pW/cell | L. Nassberger et. al 1986 |
| Human keratinocytes | 40 pW/cell | U. Reichert et. al 1986 |

The metabolically complex liver cell generates 350 pW/cell and may be an ideal sample to demonstrate the applicability of the Picocalorimeter. Such a single liver hepatocyte could be monitored with a 5:1 signal to noise ratio. The sensitivity of the Picocalorimeter can be utilized to measure the dose-response relationship between a beta-adrenergic agonist and heat production in hepatocytes. The effects of Dinitrophenol, which uncouples heat production from oxygen consumption, on heat production can then be examined, which in turn can be used to optimize the Picocalorimeter and determine its sensitivity and the response times to fluctuations in heat production.

The microfluidic components and controls discussed elsewhere in the specification may be adapted, incorporated and enhanced to allow for thermal isolation of each cell environment. The Picocalorimeter with the living cell may be hermetically sealed with a cap to protect the cell environment from contamination. Supply and waste microchannels may connect to micropipettes that can be moved in and out of the liquid drop surrounding the cell. Actuation of the micropipettes can be accomplished by either deflection of piezo bimorphs connected to the micropipettes, or deflection of the sealing membrane by the piezoelectric filament array also used to actuate the pumps and valves.

In yet another aspect, the present invention relates to a device for measuring at least one of cellular physiological activities of at least one cell, where each of the cellular physiological activities can be characterized by a reaction time. In particular, the device can be utilized to measure the energy generation and consumption of a single or multiple cells. In one embodiment as shown in FIGS. 6(A)-(D), a device 600 includes a membrane 606 having a first surface 651, an opposite second surface 653 and a thickness, wherein the membrane 606 has a sensing area 659 for receiving the at least one cell 611 such that the membrane 606 is underneath the at least one cell 611. The device 600 further includes a substrate 602 positioned opposite to the membrane 606 and having an inside surface 661 and an opposite outside surface 663, wherein the inside surface 661 of the substrate 602 cooperates with the first surface 651 of the membrane 606 to define passage 670 therebetween. The substrate 602 has a first flexible portion 665 located at one side of the sensing area 659 of the membrane 606 and a second flexible portion 667 located at another side of the sensing area 659. A sensor 607 is positioned underneath the sensing area 659 of the membrane 606 for measuring at least one of cellular physiological activities of the cell 611. The membrane 606 and the sensor 607 are arranged such that at least one of cellular physiological activities of the cell 611 is measured at a time period shorter than the reaction time.

The device 600 may also include a biocompatible coating layer (not shown) applied to the first surface 651 of the membrane 606. The membrane 606 comprises a material with sufficiently low thermal conductivity to yield a high degree of thermal isolation between the center or sensing area 659 of the membrane 606 and the edges. For examples, the membrane 606 may comprise a dielectric material. The membrane 606 may also comprise a silicon nitride membrane 606. Moreover, the membrane 606 is at least partially transparent so that the status and/or response of the cell 611 can be optically detected. The dimensions of the membrane 606 can be chosen to meet different needs.

The first flexible portion 665 of the substrate 602 has a first diaphragm that is actionable by a force. When a force is applied to the first diaphragm, the first diaphragm moves along the direction of the force. As an example, the first diaphragm can be a PDMS membrane.

The second flexible portion 667 of the substrate 602 has a second diaphragm that is actionable by a force. When a force is applied to the second diaphragm, the second diaphragm moves along the direction of the force. As an example, the second diaphragm can be a PDMS membrane. In the embodiment as shown in FIGS. 6(A)-(D), the substrate 602 is a PDMS membrane.

The first diaphragm and the second diaphragm can be utilized jointly or individually in operation. For examples, when a first force is applied to the first diaphragm towards the outside surface 663 of the substrate 602, the first diaphragm moves along the direction of the force to reach to the first surface 651 of the membrane 606, and when a second force is applied to the second diaphragm towards the outside surface 663 of the substrate 602, the second diaphragm moves along the direction of the force to reach to the first surface 651 of the membrane 606, thereby to form an isolated region therebetween, In the embodiment as shown in FIGS. 6(A)-(D), the first flexible portion 665 and the second flexible portion 667, when pushed by air pressure through inlets 601, form an enclosed measurement volume 617 containing the cell 611 therein and isolating the cell 611 from communication with fluid outside the measurement volume 617. Note that the first diaphragm and the second diaphragm can be separate elements, or integral parts of a ring-shaped diaphragm that substantially encircles the measurement volume 617, as shown in FIG. 6.

Conversely, when at least one of the first force and the second force is withdrawn, a corresponding one of the first diaphragm and the second diaphragm moves away from the first surface 651 of the membrane 606, thereby to allow the isolated region inside measurement volume 617 in fluid communication at least partially with the passage 670.

Thus, as shown in FIGS. 6(A)-(D), device 600 can be utilized to measure the energy generation and consumption of a single or multiple cells. The device 600 uses a first membrane 606 that is sufficiently thin with a sensor 607 to measure the basal energy generated by a cell 611 in a measurement volume 617 thermally isolated from the surrounding using a gas/air filled space bounded by a second membrane 602 that is sufficiently thin. By pressurizing the gas filled chamber 613 through the inlets 601, the chamber 613 can be expanded to isolate the liquid media surrounding the cell 611 in the passage 670 to form a droplet, which has inlet 615 and outlet 616 for supplying a stream of fresh media and draining spend media from the measurement volume 617, respectively. Valves 610 can be utilized to allow the control of the inflow and outflow of the stream through the passage 670. On top of the measurement volume 617, there is a gas filled chamber 604, which is stiffened by bridges 612 or is pressurized to avoid a collapse or deformation of the measurement volume 617 when the membrane 602 is inflated during the measurement cycle. Additional electrodes 608 can be used to monitor various metabolites in the droplet in order to detect, for example, metabolic pathway switching. The electrodes 608 can be coupled through the lead 614 to a sensing unit (not shown). It will be appreciated that means other than pressurized gas can be used to move the first flexible portion 665 and the second flexible portion 667, which could also be any other low-thermal conductivity barrier or object that may be mechanically placed around the cell with a piezoelectric or other mechanical actuator and the like.

Example 6

Signal Extraction and Discrimination

It will be appreciated that practicing the present invention often involves apparatuses or devices that have biological, electronic and microfluidic components interfacing each other and interacting together. To build these devices, a design theory is developed that is supported by an integrated modeling paradigm (language) that allows the modeling, analysis, simulation, and synthesis of these hybrid systems. The information or INFO component of the present invention develops this modeling language, and selects and/or builds analysis and synthesis tools for the present invention. One of them is a Bio-Micro CAD tool that can be used by biologists, biochemists, and diagnosticians to produce biocontrollers.

Currently, there is no integrated effort that would address all of the needs of a bio-silicon hybrid device. Silicon behavioral (analog or digital circuit) simulators exist, and there are efforts for engineering biological processes using (circuit) simulation techniques, but there is no integrated modeling and analysis framework that would combine the two. In one aspect, the present invention provides an integrated bio-silicon-hybrid system design environment to meet the need.

Figure 8:
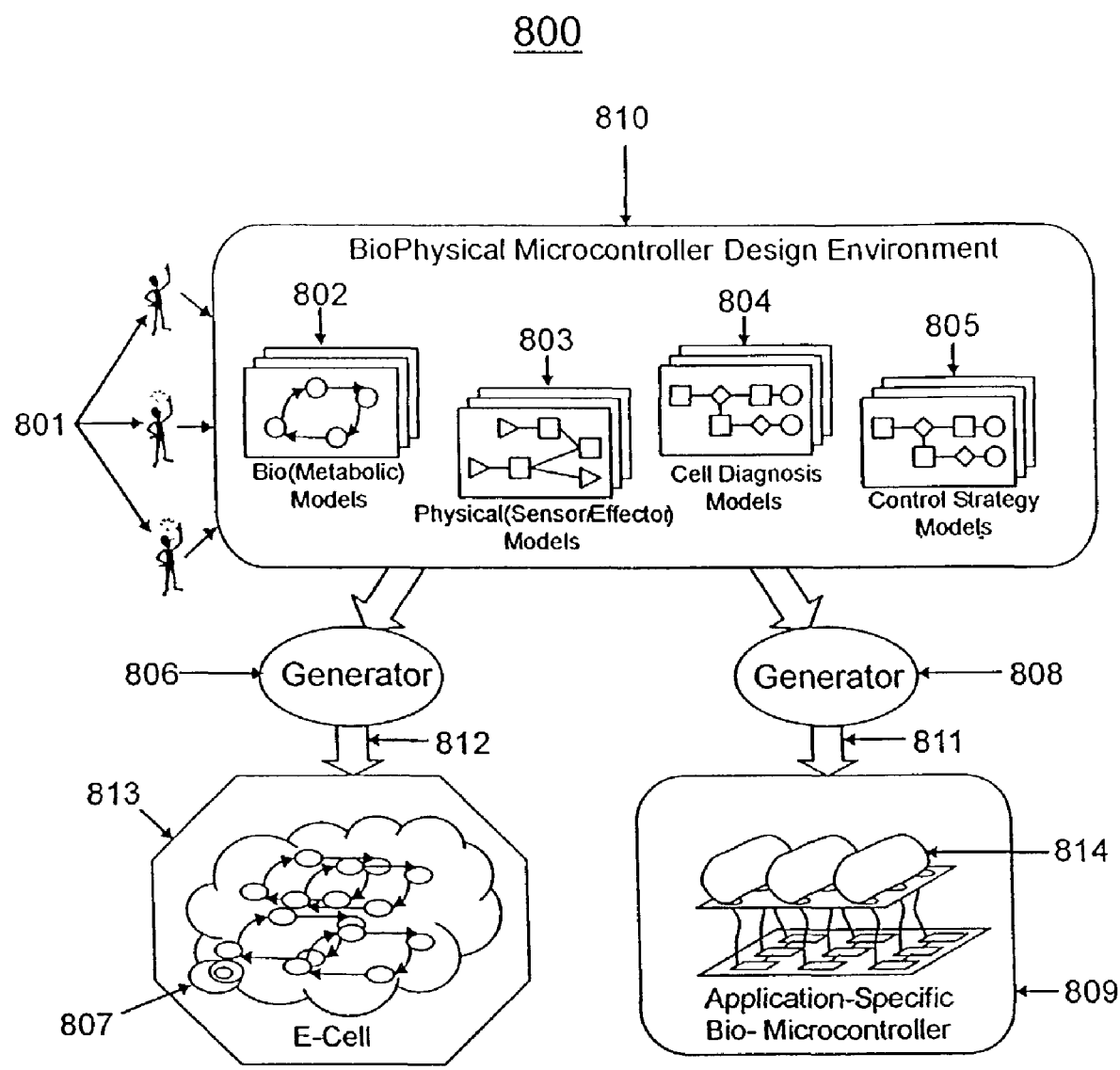
FIG. 8 illustrates an integrated bio-silicon-hybrid system design environment according to one embodiment of the invention.

As schematically shown in FIG. 8, a design environment 800 according to the present invention has multiple customized interfaces 801 communicating with users including microbiologists, hardware/sensor engineers, and diagnostic experts. The design environment 800 has a microcontroller 810 that, among other things, contains models 802-805 operated therein, receives inputs from the interfaces 801 and drives system generators 806, 808. System models include biological models 802 that capture cellular metabolic cycles including cellular products, physical models 803 that capture sensor configurations, digital processors, fluid processing hardware, and other devices on the chip, cell diagnosis models 804 that capture the differential diagnosis procedure including measurement parameters, decision logic based on measured/computed parameters, and physical actions to change cellular environmental parameters, control strategy models 805 that define how to achieve the cellular environmental parameter changes using the hardware defined in the physical models 802. Models can be added, deleted, edited, modified, tested, operated, used, saved, and upgraded, among other things. Moreover, the design environment 800 has one more system generators for various tasks. For examples, system generator 806 creates simulations of the procedures and physical structures as defined by any or any combination of models 801-805 and generates simulation configuration data 812 to drive a biological simulator 813, in which offline simulations execute these models 807, and produce data that can be used to optimize corresponding models 801-805. System generator 808 converts the models 801-805 into executable code 811 that contains the software and hardware configuration information, and runs on the physical device 809 to perform cell diagnostics in the application-specific bio-microcontroller 814 accordingly. More descriptions about what the design environment 800 can do are given below.

In one aspect, the present invention relates to a method for discriminating an agent. To do so, a process for agent classification needs to be defined. In one embodiment, overall agent classification can be implemented in the design environment 800 by successive refinement of diagnostic hypotheses. The steps in this process can be defined using a diagnosis tree having a plurality of branches. At each branch of the tree, a context-sensitive experiment is conducted and data acquired and analyzed. The context is a result of all prior experiments and decisions. At each experiment/assay, the following steps are performed:

Setting assay conditions, including: (a) Selecting the type and quantity of cells to be exposed; (b) Modifying the 'setpoints' of the cell, (e.g., changing pH to make the cell metabolism more sensitive to a particular protein, etc.); (c) applying the unknown agent to the cells with a user-specified profile;

Acquiring data from the sensors, and processing it into "features". Features represent processed information from the raw signal, converting a time sequence of raw A/D sample counts into a small number of parameters. Arbitrarily complex feature extraction algorithms can be defined by connecting software modules from a library of signal analysis functions (e.g., slope, frequency analysis, parametric modeling, etc.) in a Lab View-like environment; and Applying a discrimination function to evaluate the features, dividing into classes of responses. The classification assurance will be assessed and used to select the next branch of the decision tree. Discrimination functions can be implemented to form a library of techniques (Principal Component/Factor Analysis, Statistical Clustering/Maximum Likelihood Estimation, Parametric Model/System Identification, Neural Networks, User-Defined, etc.).

In operation, care should be taken to integrate control and diagnosis to conserve valuable resources (limited number of cells, limited quantity of reagents), and modify cell conditions to enhance sensitivity of the biological systems to improve quality (e.g., to increase probability of detect, to reduce false alarm rate, etc.).

Defining the diagnosis tree is an experiment- and data-intensive, iterative process. As shown in FIG. 8, the design environment 800 is capable of supporting programming of the system by a plurality of users 801. A Model-Integrated Computing ("MIC") approach is utilized to design and implement a Domain-Specific language for agent classification. The MIC approach has proven successful at a wide variety of embedded systems and diagnostic domains.

Figure 22:
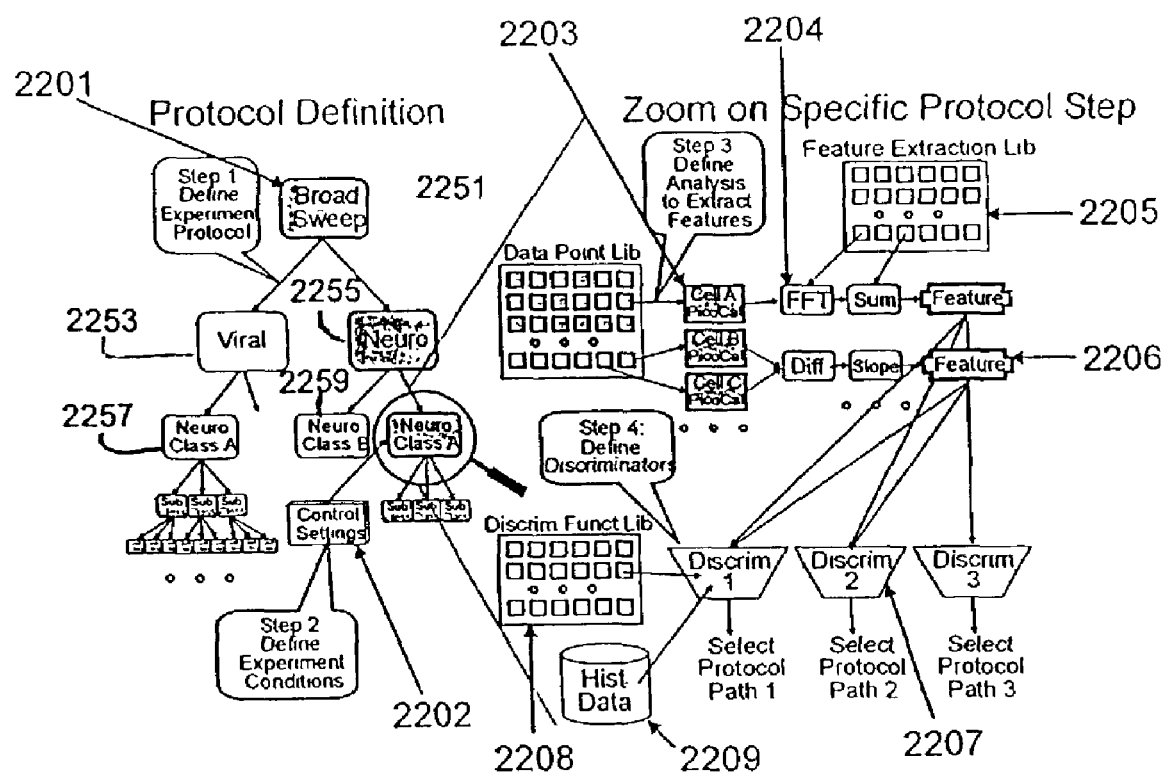
FIG. 22 is a flowchart illustrating a Process to define a differential discrimination process according to one embodiment of the invention.

Discrimination can be achieved in several ways according to the present invention. Referring now to FIG. 22, a differential discrimination process is shown. In step 1, a series of incremental refinement procedures 2201 are defined as a decision tree. Starting with a broad sweep assay, and using the results of a discrimination process, the agent is identified as being either viral or neural. Moreover, classes and subclasses of neural responses are identified by choosing a new assay to further refine decisions, which can be considered as branches and successive branches of the decision tree. Refinement proceeds until sufficient confidence and discrimination is achieved. In Step 2, experimental conditions and control setting parameters 2202, such as cell type and quantity to expose to the unknown agent, cell bath composition, or the like, are defined. In Step 3, the individual entries 2203 in a first database, where is shown as Data Point Library, are used to define a detailed discrimination process that involves specific measurements 2204 such as fast Fourier transforms ("FFT"), summations, differences, and feature extraction, during which a feature extraction algorithm is graphically defined in a second database 2205, where is shown as Feature Extraction Library, that contain common signal processing primitives to produce the resulting feature 2206 that is quantified. At step 4, discrimination functions or discriminators are defined by using several features 2207 to indicate differential diagnostics paths to choose, and/or obtained from a third database 2208, where is shown as Discrimination Functions Library, and a historical data base 2209 that contains common discrimination functions and provides a historical record available for use in discrimination and algorithm verification. As a result, one or more discrimination functions, i.e. classification information about the agent, are generated, which can be used to select the next branch of the diagnosis tree. These discriminators can also be used to discriminate or classify the agent from the measured signals corresponding to the agent. The process can be repeated until the agent is discriminated.

Accordingly, as shown in FIG. 22 and discussed above, one method 2200 for discriminating an agent according to one embodiment of the present invention includes the steps of (a) constructing a decision tree 2251 having a plurality of branches 2253, 2255, each branch corresponding to at least one defined action, wherein each branch includes a plurality of successive branches 2257, 2259, each successive branch corresponding to at least one defined action, (b) providing a conditioned environment 2202 sensitive to the agent, (c) obtaining data from response of the agent to the conditioned environment at 2203, (d) extracting features from the obtained data at 2204, (e) selecting a branch from the decision tree corresponding to the features at 2206, (f) performing on the features at least one defined action corresponding to the branch, and (g) producing a classification of the agent at 2207. Some of the above steps can be iteratively repeated until the agent is discriminated.

In doing so, as shown in FIG. 22, at the start, a decision is made regarding the choice of logic for successive refinement of agent classification, where it can be chosen as logic for classification of a Neuro agent at 2255, or logic for classification of a Viral agent at 2253. The agent may include a chemical agent, a non-chemical agent, a biological agent, or a non-biological agent. Examples of the agent can be found above.

Figure 23:
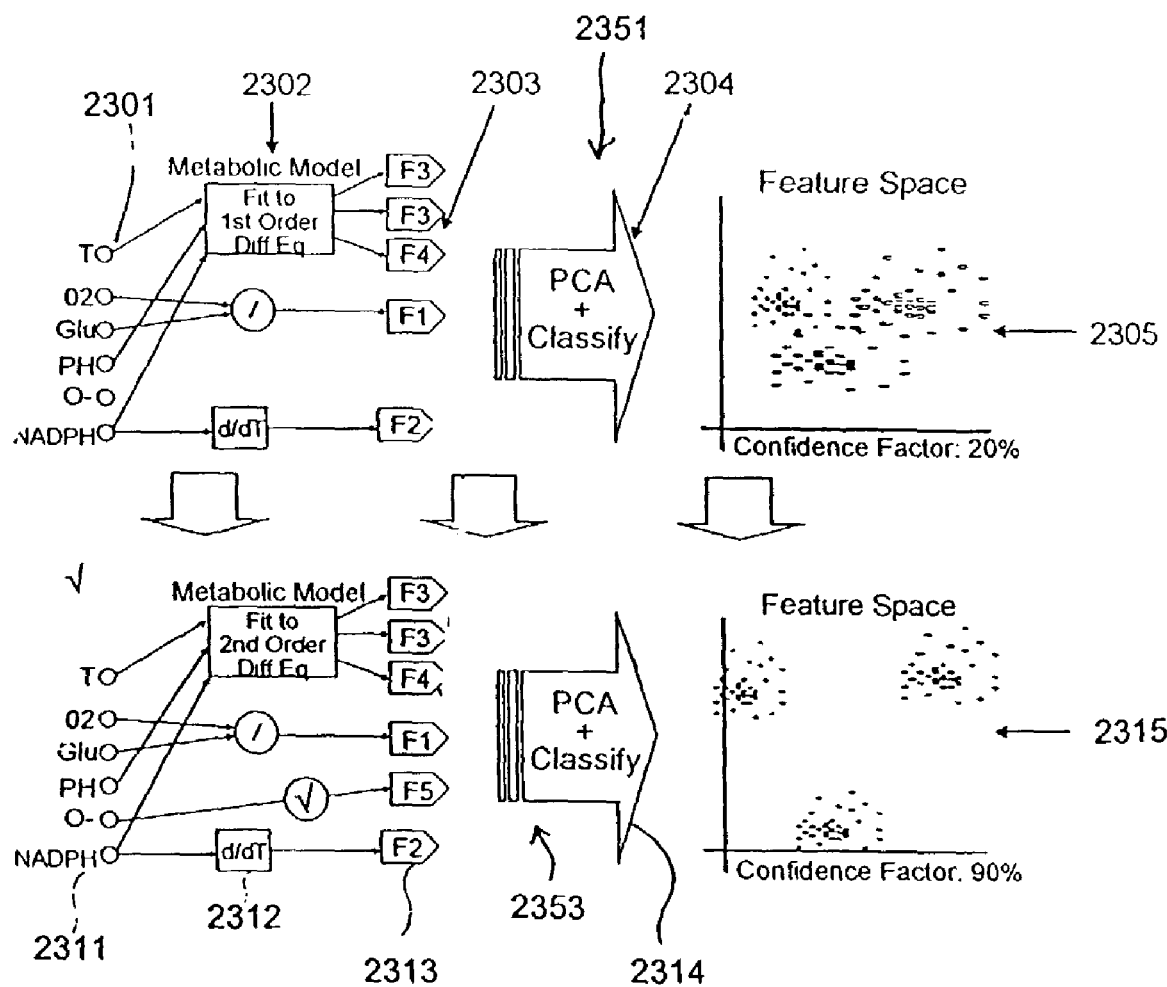
FIG. 23 illustrates two signal classification algorithms s according to one embodiment of the invention.

Different signal classification algorithms can be utilized to classify an agent. In one embodiment as shown in FIG. 23, for the process 2351 shown at the upper half, sets of available measurements 2301, where each measurement represents a parameter related to the status of the agent, for example, the entry of a toxin to a conditioned environment having cells may cause temporal response measured as T, are chosen and used as input data to the feature extraction process 2302 that graphically define algorithms to extract properties from the raw cellular measurements. From these data, feature sets 2303 are computed from solving a set of first order differential equations although second order, or high order differential equations may also be used. Feature sets 2303 are then analyzed at 2304 by classification algorithms including principal component analysis and other linear/nonlinear classifiers to separate the features into a feature space 2305. Space 2305 is an example of a poorly classified decision, where feature distributions overlap to each other, based upon a particular feature extraction process 2302. A similar process 2353 as shown in the lower half of FIG. 23, however, produces a feature space 2306 that represents a good classification of three regions from a different extraction process. One difference is that process 2353 uses a at of second order differential equations at step 2312 as discussed in more detail below.

Indeed, an important phase of signal classification is the initial feature extraction. Feature extraction can take the form of simple mathematical operations on signals (add/subtract, compute slope/area-under-curve) or can incorporate metabolic or other physiological information such as intracellular or intercellular signaling activity via parameter matching to biological models. Design of the feature extraction algorithms is an iterative process as partially shown in FIG. 23. As shown in the upper half of FIG. 23, the initial attempt 2351 selects a set of sensor inputs (temperature, oxygen, pH, etc.). A first-order differential equation model of metabolic pathways is used to extract features from T, pH, and NADPH amongst other algorithms. A Principal-Component-Analysis (PCA)/Cluster separation reveals that the classes are only separable with a 20% confidence level.

In the lower half of FIG. 23, a refinement of the feature extraction shown as process 2353 changes the biological model to 2nd order and adds a new model as a feature (O—). Successive PCA shows that the classes are now separable with a 90% confidence level. Among other things, the feature extraction primitives include (1) Standard mathematical/DSP functions, (2) Model Parameter Identification for 1st, 2nd, and 3rd order rate equations, (3) Mean transit time and Impulse response models, and (4) Kinetics of mass/heat diffusion. In addition, generic 'shells' will be available to perform user-defined analysis.

Classified data are stored in a database for further use. However, when building the experimental classification database in an unsupervised mode, the input to the algorithms are unlabelled examples. Unsupervised classification algorithms are used to discover natural structures in the data and can provide valuable insight into the problem and guide the development of classification system. As described above, the design environment 800 can be used for a wide range of applications. On one end of the spectrum, it can be used to design decision trees that are based entirely on deep physiological knowledge. In this scenario, the number of features at each decision node would be relatively limited and assignment to one class or the other would be made on the goodness of fit between data and model. On the other end of the spectrum it can be used to design classification systems even if very little is known about physiological principles. In this scenario, the number of features would be large, the system provided with labeled examples, and it would simply compute decision boundaries in the feature space.

Figure 24:
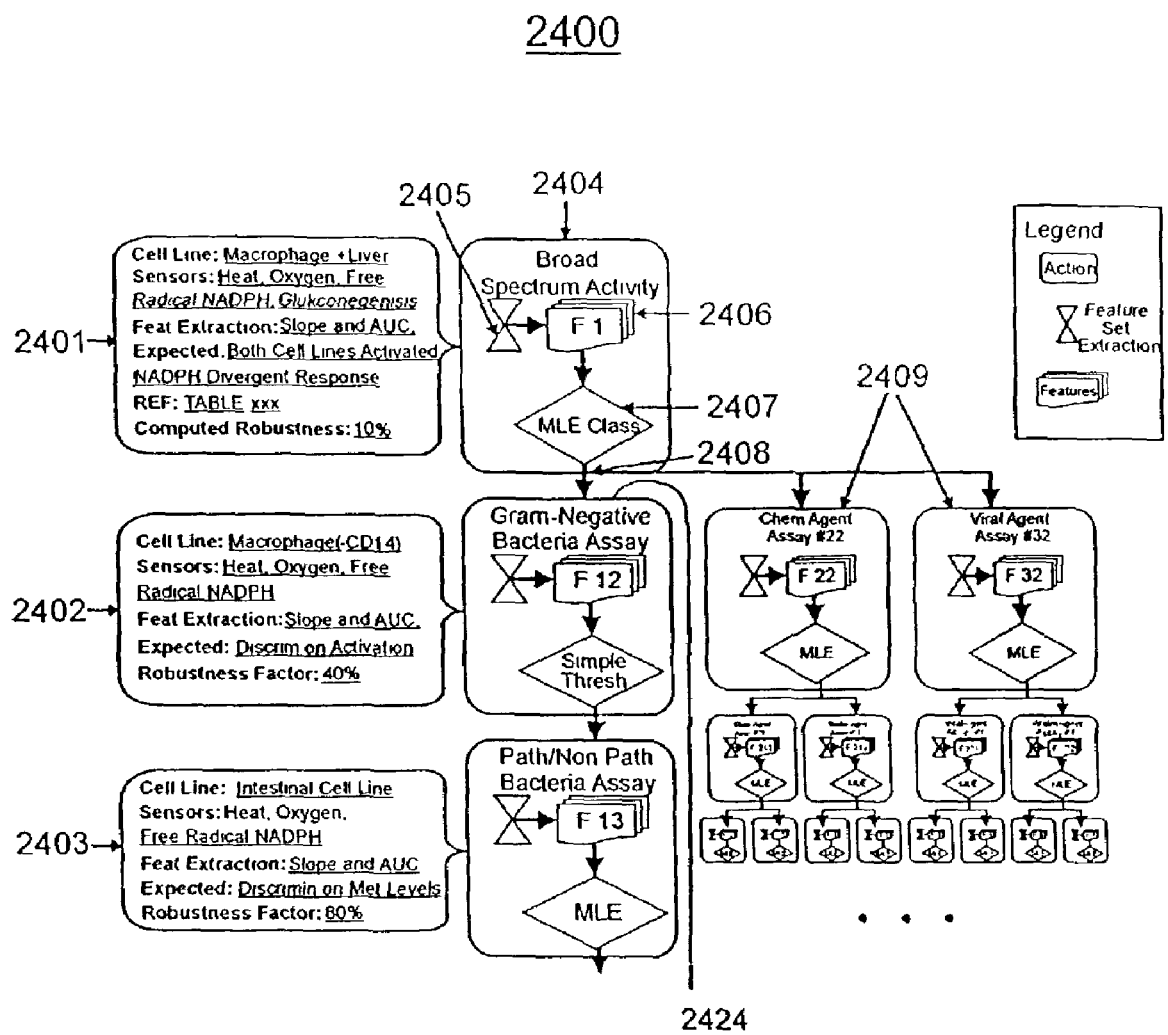
FIG. 24 schematically shows a diagnostics path or process according to one embodiment of the present invention.

FIG. 24 illustrates a diagnostics path to develop an assay according to one embodiment of the present invention. Note that this is illustrative of the definition process and represents a small fraction of a complete diagnostics process. The first step is to have a broad spectrum assay. Robust, relatively insensitive cells from cell lines are used to provide a long-lived activity detector. The broad assay may separate responses into one of several broad classes, discriminated by a Maximum Likelihood Estimator. FIG. 24 further illustrates the next step for Gram-Negative Bacteria. A new set of engineered cell lines is selected for their sensitivity to the presence or absence of CD-14 (i.e., endotoxin receptor), along with instrumentation to measure the anticipated indicators. The expected response is used to define a set of feature extraction algorithms. In this case, a simple threshold serves as a classifier. The third step in the path chooses intestinal cells to determine if a pathogenic enterotoxin is secreted by the gram negative bacteria, a set of sensors, feature extraction algorithms, and a MLE classifier. Note that there may be additional steps to be performed.

Accordingly, as shown in FIG. 24, diagnosis process 2400 proceeds as follows. At step 2401, cell lines, sensors, and analysis metadata are chosen and obtained to provide a broad-spectrum activity assay at 2404. Feature extraction algorithms are utilized at 2405 to define how to convert raw sensor measurements into features at 2406. The features resulting from feature extraction are examined by a classifier method at 2407, which is selected for its ability to discriminate agent classes. Classification results are used to make a decision of which path to proceed at 2408. For examples, a second set of cell lines, sensors, and analysis metadata are chosen and obtained to provide a broad-spectrum activity assay at 2424 and subsequent analysis is repeated to generate new classification results. For poor discriminations, multiple paths can be followed at step 2409. Additional subsequent steps that follow the same procedures, with specific feature extraction and classification methods at 2403 (or more) can be repeated until desired results are obtained, for example, when a desired robustness factor is obtained.

While there has been shown various embodiments of the present invention, it is to be understood that certain changes can be made in the form and arrangement of the elements of the system and steps of the methods to practice the present invention as would be known to one skilled in the art without departing from the underlying scope of the invention as is particularly set forth in the Claims. Furthermore, the embodiments described above are only intended to illustrate the principles of the present invention and are not intended to limit the claims to the disclosed elements.

What is claimed is:

1. A method for monitoring the status of one or more metabolically active cells comprising one or more cell species, comprising the steps of:
   a. confining each cell species of the one or more metabolically active cells in one of a plurality of sensing volumes, wherein each sensing volume is coupled with a plurality of different sensors;
   b. simultaneously measuring two or more analytes of each cell species of the one or more metabolically active cells in each sensing volume at a first time, wherein the simultaneously measuring is done by the recording of the time-course of a plurality of analytes consumed or produced as a result of metabolic activities of the one or more metabolically active cells, and wherein the measurement of each analyte of the one or more metabolically active cells is characterized by a response time;
   c. simultaneously measuring the two or more analytes of each cell species of the one or more metabolically active cells in each sensing volume at a second time, wherein the step of measuring at the first time and the step of measuring at the second time both are performed by the plurality of different sensors coupled to the corresponding sensing volume during the corresponding response time of the two or more analytes being simultaneously measured; and
   d. determining the status of each cell species of the one or more metabolically active cells from the measured two or more analytes of each cell species of the one or more metabolically active cells at the first time and the measured two or more analytes of each cell species of the one or more metabolically active cells at the second time.

2. The method of claim 1, further comprising the step of exposing the one or more metabolically active cells to at least one unknown agent.

3. The method of claim 2, wherein the analyte of each cell species of the one or more metabolically active cells changes when the at least one unknown agent interacts with the corresponding cell species, and wherein the determining step comprises the step of identifying the at least one unknown agent from the changes of the measured two or more analytes of the corresponding cell species at the first time and the measured two or more analytes of the corresponding cell species at the second time.

4. The method of claim 3, wherein the analyte of each cell species of the one or more metabolically active cells comprises a temporal response, wherein the temporal response of each cell species of the one or more metabolically active cells is measured in at least two measurements.

5. The method of claim 3, wherein the determining step further comprises the step of quantifying the at least one unknown agent from the measured two or more analytes of the corresponding cell species at the first time and the measured two or more analytes of the corresponding cell species at the second time.

6. The method of claim 4, wherein the time period between the at least two measurements is within a time period corresponding to the temporal response of each cell species of the one or more metabolically active cells.

7. The method of claim 1, wherein the determining step comprises the step of determining metabolic inactivity of the one or more metabolically active cells.

8. The method of claim 1, further comprising the step of maintaining each cell species of the one or more metabolically active cells in a conditioned environment.

9. The method of claim 8, wherein the maintaining step comprises the step of keeping each cell species of the one or more metabolically active cells in a solution of media.

10. The method of claim 1, wherein the analyte of each cell species of the one or more metabolically active cells includes consumption or secretion of a chemical component by the cell species that relates to the metabolic status of the cell species.

11. The method of claim 10, wherein the chemical component comprises at least one selected from the group consisting of pH, K (potassium), oxygen, lactate, glucose, ascorbate, serotonin, dopamine, ammonia, glutamate, purine, calcium, sodium, NADH (nicotinamide adenine dinucleotide), protons, insulin, NO (nitric oxide) and the derivatives of them.

12. An apparatus for monitoring the status of one or more metabolically active cells comprising one or more cell species, comprising:
   a. means for confining each cell species of the one or more metabolically active cells in one of a plurality of sensing volumes, wherein each sensing volume is coupled with a plurality of different sensors;
   b. means for simultaneously measuring two or more analytes of each cell species of the one or more metabolically active cells in each sensing volume at a first time and a second time, respectively, wherein the simultaneously measuring is done by the recording of the time-course of a plurality of analytes consumed or produced as a result of metabolic activities of the one or more metabolically active cells, and wherein the measurement of each analyte of the one or more metabolically active cells is characterized by a response time, wherein the measuring means is configured and positioned to perform both the measuring by the plurality of different sensors coupled to the corresponding sensing volume at the first time and at the second time during the corresponding response time of the two or more analytes being simultaneously measured; and
   c. means for determining the status of each cell species of the one or more metabolically active cells from the measured two or more analytes of each cell species of the one or more metabolically active cells at the first time and the measured two or more analytes of each cell species of the one or more metabolically active cells at the second time.

13. The apparatus of claim 12, further comprising means in communication with the confining means for exposing the one or more metabolically active cells to an unknown agent.

14. The apparatus of claim 13, wherein the analyte of each cell species of the one or more metabolically active cells changes when the unknown agent interacts with the corresponding cell species, and wherein the determining means comprises means for identifying the unknown agent from the changes of the measured two or more analytes of the corresponding cell species at the first time and the measured two or more analytes of the corresponding cell species at the second time.

15. The apparatus of claim 14, wherein the determining means further comprises means for quantifying the unknown agent from the measured two or more analytes of the corresponding cell species at the first time and the measured two or more analytes of the corresponding cell species at the second time.

16. The apparatus of claim 12, wherein the analyte of each cell species of the one or more metabolically active cells comprises a temporal response, wherein the temporal response of each cell species of the one or more metabolically active cells is measured in at least two measurements.

17. The apparatus of claim 16, wherein the time period between the at least two measurements is within a time period corresponding to the temporal response of each cell species of the one or more metabolically active cells.

18. The apparatus of claim 12, further comprising means for maintaining each cell species of the one or more metabolically active cells in a conditioned environment.

19. The apparatus of claim 18, wherein the maintaining means comprises means for keeping each cell species of the one or more metabolically active cells in a solution of media.

* * * * *